United States Patent [19]
Or et al.

[11] Patent Number: 6,054,435
[45] Date of Patent: Apr. 25, 2000

[54] 6-O-SUBSTITUTED MACROLIDES HAVING ANTIBACTERIAL ACTIVITY

[75] Inventors: Yat Sun Or, Libertyville; Richard F. Clark, Mundelein; Zhenkun Ma, Gurnee; Michael John Rupp, Lake Bluff, all of Ill.

[73] Assignee: Abbott Laboratories, Abbott Park, Ill.

[21] Appl. No.: 09/273,140

[22] Filed: Mar. 19, 1999

[51] Int. Cl.[7] .............................. A61K 31/70; C07H 1/00; C07H 17/08

[52] U.S. Cl. .............................. 514/29; 536/7.2; 536/7.5; 536/18.5

[58] Field of Search ............................ 536/7.2, 7.5, 18.5; 514/29

[56] References Cited

U.S. PATENT DOCUMENTS

| | | | |
|---|---|---|---|
| 5,350,839 | 9/1994 | Asaka et al. | 536/7.4 |
| 5,444,051 | 8/1995 | Agouridas et al. | |
| 5,527,780 | 6/1996 | Agouridas et al. | 514/29 |
| 5,561,118 | 10/1996 | Agouridas et al. | 514/29 |

FOREIGN PATENT DOCUMENTS

| | | |
|---|---|---|
| 0487411 | 5/1992 | European Pat. Off. |
| 0596802 | 5/1994 | European Pat. Off. |
| 0656364 | 6/1995 | European Pat. Off. |
| 0676409 | 10/1995 | European Pat. Off. |
| 0680967 | 11/1995 | European Pat. Off. |
| 2697524 | 5/1994 | France |
| 2738571 | 3/1997 | France |
| 9209614 | 6/1992 | WIPO |
| 9313116 | 7/1993 | WIPO |
| 9313663 | 7/1993 | WIPO |
| 9321199 | 10/1993 | WIPO |
| 9321200 | 10/1993 | WIPO |
| 9710251 | 3/1997 | WIPO |

OTHER PUBLICATIONS

Pestka, et al. (I), "Effect of Erythromycin Analogues on Binding of [$^{14}$C] Erythromycin to *Escherichia coli* Ribosomes," *Antimicrobial Agents and Chemotherapy*, 6(4), 479–488 (Oct. 1974).

Pestka et al. (II), "Correlation of Effects of Erythromycin Analogues on Intact Bacteria and on [$^{14}$C] Erythromycin to *Escherichia coli* Ribosomes," *Antimicrobial Agents and Chemotherapy*, 6(4), 488–491 (Oct. 1974).

Pestka, et al. (III), "Inhibition of [$^{14}$C] Chloramphenicol Binding to *Escherichia coli* Ribosomes by Erythromycin Derivatives," *Antimicrobial Agents and Chemotherapy*, 6(1), 39–45 (Jul. 1974).

Pestka, et al. (IV), "Induction of Erythromycin Resistance in *Staphylococcus aureus* by Erythromycin Derivatives," *Antimicrobial Agents and Chemotherapy*, 9(1), 128–130 (Jan. 1976).

LeMahieu et al., "Glycoside Cleavage Reactions to Erythromycin A. Preparation of Erythromycin A." *J. Medicinal Chem.* 17 (9), 953–956 (Sep. 1974).

*Primary Examiner*—Elli Peselev
*Attorney, Agent, or Firm*—Mona Anand; Dugal Sickert

[57] ABSTRACT

The instant invention provides novel macrolide compounds and compositions useful in treating bacterial infections. Also provided are processes for preparing same.

14 Claims, No Drawings

6-O-SUBSTITUTED MACROLIDES HAVING ANTIBACTERIAL ACTIVITY

TECHNICAL FIELD

This invention relates to novel macrolide compounds having antibacterial activity, to pharmaceutical compositions comprising these compounds, to methods of treating bacterial infections using said compounds, and to methods of making these novel compounds.

BACKGROUND OF THE INVENTION

Erythromycins A through D are represented by the following formula:

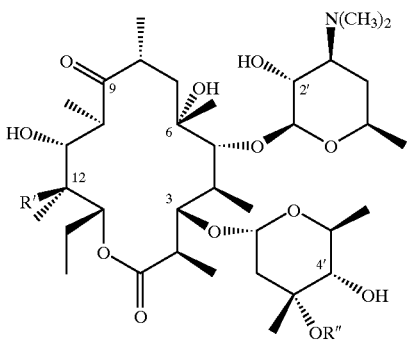

| Erythromycin | R' | R'' |
|---|---|---|
| A | —OH | —CH$_3$ |
| B | —H | —CH$_3$ |
| C | —OH | —H |
| D | —H | —H | and are well-known and potent antibacterial agents. These compounds are used widely to treat and prevent bacterial infection. As with other antibacterial agents, however, bacterial strains having resistance or insufficient susceptibility to erythromycin have been identified. Erythromycin A has only weak activity against Gram-negative bacteria. Therefore, there is a continuing need to identify new macrolide compounds which possess improved antibacterial activity, which have less potential for developing resistance, which possess the desired Gram-negative activity, and/or which possess unexpected selectivity against target microorganisms. Consequently, numerous investigators have prepared chemical derivatives of erythromycin in an attempt to obtain analogs having modified or improved profiles of antibiotic activity.

U.S. Pat. No. 5,444,051 discloses 6-O-substituted-3-oxoerythromycin A derivatives in which the substituents are selected from alkyl, —CONH$_2$, —CONHC(O)alkyl and —CONHSO$_2$alkyl. WO 97/10251, published Mar. 20, 1997, discloses 6-O-methyl 3-descladinose erythromycin derivatives. European Patent Application 596802, published May 11, 1994, discloses bicyclic 6-O-methyl-3-oxoerythromycin A derivatives. WO 92/09614, published Jun. 11, 1992, discloses tricyclic 6-O-methylerythromycin A derivatives.

SUMMARY OF THE INVENTION

The present invention relates to compounds selected from the group consisting of a compound of formula I

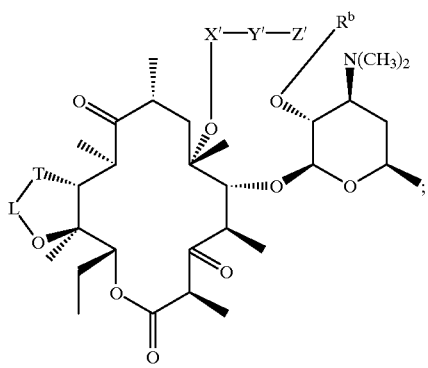

a compound of formula II

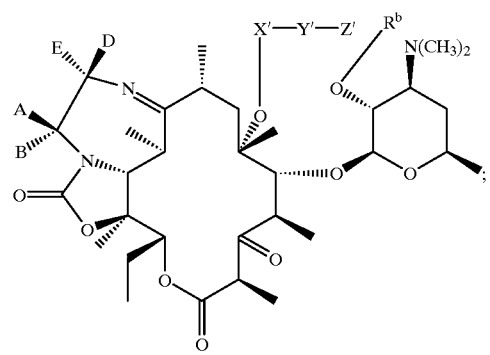

and a compound of formula III

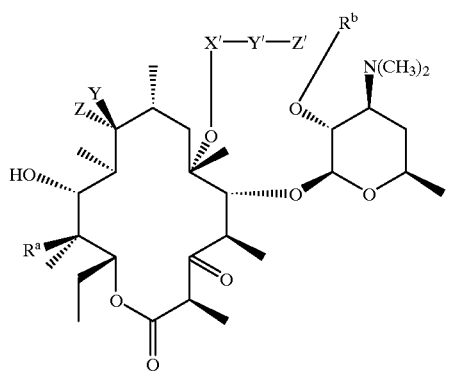

or a pharmaceutically acceptable salt, solvate, ester or prodrug thereof, wherein either:
(a) Y and Z taken together define a group X, and X is selected from the group consisting of
  (1) =O,
  (2) =N—OH,
  (3) =N—O—R$^1$ where R$^1$ is selected from the group consisting of
    (a) unsubstituted C$_1$–C$_{12}$ alkyl,
    (b) C$_1$–C$_{12}$ alkyl substituted with aryl,
    (c) C$_1$–C$_{12}$ alkyl substituted with substituted aryl,
    (d) C$_1$–C$_{12}$ alkyl substituted with heteroaryl,
    (e) C$_1$–C$_{12}$ alkyl substituted with substituted heteroaryl, (f) $C_3$–$C_{12}$ cycloalkyl, and
(g) —Si—($R^2$)($R^3$)($R^4$) wherein $R^2$, $R^3$ and $R^4$ are each independently selected from $C_1$–$C_{12}$ alkyl and aryl; and
(4) =N—O—C($R^5$)($R^6$)—O—$R^1$ where $R^1$ is as previously defined and $R^5$ and $R^6$ are each independently selected from the group consisting of
(a) hydrogen,
(b) unsubstituted $C_1$–$C_{12}$ alkyl,
(c) $C_1$–$C_{12}$ alkyl substituted with aryl,
(d) $C_1$–$C_{12}$ alkyl substituted with substituted aryl,
(e) $C_1$–$C_{12}$ alkyl substituted with heteroaryl, and
(f) $C_1$–$C_{12}$ alkyl substituted with substituted heteroaryl,
or $R^5$ and $R^6$ taken together with the atom to which they are attached form a $C_3$–$C_{12}$ cycloalkyl ring; or
(b) one of Y and Z is hydrogen and the other is selected from the group consisting of
(1) hydrogen,
(2) hydroxy,
(3) protected hydroxy, and
(4) $NR^7R^8$ wherein $R^7$ and $R^8$ are independently selected from hydrogen and $C_1$–$C^6$ alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)—, —N(heteroaryl-$C_1$–$C_6$-alkyl-)—, —N(substituted-heteroaryl-$C_1$–$C_6$-alkyl-)—, and —S— or —S(O)$_n$—, wherein n is 1 or 2;

$R^a$ is hydrogen or hydroxy;
$R^b$ is hydrogen or a hydroxy protecting group;
L is methylene or carbonyl, provided that when L is methylene, T is —O—;
T is selected from the group consisting of —O—, —NH—, and —N(W—$R^d$)—, wherein W is absent or is selected from the group consisting of —O—, —NH—CO—, —N=CH— and —NH—, and $R^d$ is selected from the group consisting of
(1) hydrogen,
(2) $C_1$–$C_6$-alkyl optionally substituted with one or more substituents selected from the group consisting of
(a) aryl,
(b) substituted aryl,
(c) heteroaryl,
(d) substituted heteroaryl,
(e) hydroxy,
(f) $C_1$–$C_6$-alkoxy,
(g) $NR^7R^8$, wherein $R^7$ and $R^8$ are as defined previously, and
(h) —$CH_2$—M—$R^9$,
wherein M is selected from the group consisting of:
(i) —C(O)—NH—,
(ii) —NH—C(O)—,
(iii) —NH—,
(iv) —N=,
(v) —N($CH_3$)—,
(vi) —NH—C(O)—O—
(vii) —NH—C(O)—NH—
(viii) —O—C(O)—NH—
(ix) —O—C(O)—O—
(x) —O—,
(xi) —S(O)$_n$—, wherein n is 0, 1 or 2,
(xii) —C(O)—O—,
(xiii) —O—C(O)—, and
(xiv) —C(O)—; and
wherein $R^9$ is selected from the group consisting of:
(i) $C_1$–$C_6$ alkyl, optionally substituted with a substituent selected from the group consisting of
(aa) aryl,
(bb) substituted aryl,
(cc) heteroaryl, and
(dd) substituted heteroaryl;
(ii) aryl,
(iii) substituted aryl,
(iv) heteroaryl,
(v) substituted heteroaryl, and
(vi) heterocycloalkyl;
(3) $C_3$–$C_7$ cycloalkyl,
(4) aryl,
(5) substituted aryl,
(6) heteroaryl, and
(7) substituted heteroaryl;

X' is selected from the group consisting of $C_1$–$C_{10}$ alkyl, $C_3$–$C_{10}$ alkenyl, and $C_3$–$C_{10}$ alkynyl;
Y' and Z' are independently selected from the group consisting of:
(a) optionally substituted aryl, and
(b) optionally substituted heteroaryl, with the proviso that both Y' and Z' are not both phenyl, and with the further proviso that Y' is not isoxazole when Z' is thiophenyl;
and A, B, D and E are independently selected from the group consisting of:
(a) hydrogen;
(b) $C_1$–$C_6$ alkyl, optionally substituted with one or more substituents selected from the group consisting of:
(i) aryl;
(ii) substituted aryl;
(iii) heteroaryl;
(iv) substituted heteroaryl;
(v) heterocycloalkyl;
(vi) hydroxy;
(vii) $C_1$–$C_6$ alkoxy;
(viii) halogen consisting of Br, Cl, F or I; and
(ix) $NR^7R^8$, wherein $R^7$ and $R^8$ are as previously defined;
(c) $C_3$–$C_7$ cycloalkyl;
(d) aryl;
(e) substituted aryl;
(f) heteroaryl;
(g) substituted heteroaryl;
(h) heterocycloalkyl; and
(i) a group selected from option (b) above further substituted with —M—$R^9$, wherein M and $R^9$ are as previously defined, with the proviso that at least two of A, B. D and E are hydrogen,;
or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$ alkyl-)—, —N(aryl-$C_1$-$C_6$ alkyl-)—, —N(substituted aryl-$C_1$-$C_6$ alkyl-)—, —N(heteroaryl-$C_1$-$C_6$ alkyl-)—, —N(substituted heteroaryl-$C_1$-$C_6$ alkyl-)—, —S— or —S(O)$_n$—, wherein n is 1 or 2, —C(O)—NH, —C(O)—NR$^{12}$—, wherein R$^{12}$ is selected from the group consisting of hydrogen, $C_1$-$C_3$ alkyl, $C_1$-$C_3$ alkyl substituted with aryl, substituted aryl, heteroaryl, or substituted heteroaryl, —NH—C(O)—, and —NR$^{12}$—C(O)—.

The present invention also relates to pharmaceutical compositions containing a pharmaceutically effective amount of a compound of formulae I, II or III as defined above in combination with a pharmaceutically acceptable carrier.

The present invention further relates to processes for preparing compounds of formulae I, II, or III.

The invention still further relates to methods of treating bacterial infections in a host mammal in need of such treatment comprising administering to said mammal a therapeutically effective amount of a compound of formula I, II, or III as defined above.

DETAILED DESCRIPTION OF THE INVENTION

As used throughout the specification and the claims, the following terms have the meanings specified.

The terms "$C_1$-$C_3$ alkyl", "$C_1$-$C_6$ alkyl", and "$C_1$-$C_{12}$ alkyl" as used herein refer to saturated, straight, or branched chain hydrocarbon radicals derived from a hydrocarbon moiety containing between one and three, one and six, and one and twelve carbon atoms, respectively, by removal of a single hydrogen atom. Examples of $C_1$-$C_3$ alkyl radicals include methyl, ethyl, propyl, and isopropyl, examples of $C_1$-$C_6$ alkyl radicals include methyl, ethyl, propyl, isopropyl, n-butyl, tert-butyl, neopentyl, and n-hexyl. Examples of $C_1$-$C_{12}$ alkyl radicals include all the foregoing examples, as well as n-heptyl, n-octyl, n-nonyl, n-decyl, n-undecyl, and n-docecyl.

The term "$C_1$-$C_6$ alkoxy" as used herein refers to an $C_1$-$C_6$ alkyl group, as previously defined, attached to the parent molecular moiety through an oxygen atom. Examples of $C_1$-$C_6$ alkoxy include methoxy, ethoxy, propoxy, isopropoxy, n-butoxy, tert-butoxy, neopentoxy and n-hexoxy.

The term "$C_3$-$C_{12}$ alkenyl", denotes a monovalent or divalent group derived from a hydrocarbon moiety containing from two to twelve carbon atoms and having at least one carbon-carbon double bond by the removal of a single hydrogen atom. Alkenyl groups include propenyl, butenyl, 1-methyl-2-buten-1-yl, and the like.

The term "$C_3$-$C_{12}$ alkynyl" as used herein refers to a monovalent or divalent group derived from a hydrocarbon containing from two to twelve carbon atoms and having at least one carbon-carbon triple bond by the removal of a single hydrogen atom. Representative alkynyl groups include 2-propynyl (propargyl), 1-propynyl, and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "C1–C3-alkylamino" as used herein refers to one or two C1–C3-alkyl groups, as previously defined, attached to the parent molecular moiety through a nitrogen atom. Examples of C1–C3-alkylamino include methylamino, dimethylamino, ethylamino, diethylamino, and propylamino.

The term "oxo" denotes a group wherein two hydrogen atoms on a single carbon atom in an alkyl group as defined above are replaced with a single oxygen atom (for example, a carbonyl group).

The term "aprotic solvent" as used herein refers to a solvent that is relatively inert to proton activity, for example, not acting as a proton-donor. Examples include hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al., Vol. II, in the *Techniques of Chemistry Series*, John Wiley & Sons, N.Y., 1986.

The term "aryl" as used herein refers to a mono- or bicyclic carbocyclic ring system having one or two aromatic rings including phenyl, naphthyl, tetrahydronaphthyl, indanyl, indenyl, and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "C3–C12-cycloalkyl", denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptyl, and bicyclo[2.2.2]octyl.

The terms "halo" and "halogen" as used herein refer to an atom selected from fluorine, chlorine, bromine and iodine.

The term "alkylamino" refers to a group having the structure —NHR', wherein R' is alkyl, as previously defined. Examples of alkylamino include methylamino, ethylamino, iso-propylamino, and the like.

The term "dialkylamino" refers to a group having the structure —NR'R" wherein R' and R" are independently selected from alkyl, as previously defined. Additionally, R' and R" taken together may optionally be —(CH2)k— where k is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "alkoxycarbonyl" represents an ester group, for example, an alkoxy group, attached to the parent molecular moiety through a carbonyl group such as methoxycarbonyl, ethoxycarbonyl, and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —CO2H.

The term "carboxamide" as used herein refers to a group of formula —CONHR'R" wherein R' and R" are independently selected from hydrogen or alkyl, or R' and R" taken together may optionally be —(CH2)k—, where k is an integer from 2 to 6.

The term "heteroaryl", as used herein, refers to a cyclic aromatic radical having from five to ten ring atoms of which one ring atom is selected from S, O and N; one, two, or three ring atoms may be additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, tetrazolyl, thiophenyl, furanyl, quinolinyl, isoquinolinyl, and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Specific heterocycloalkyl rings include 3-methylpiperidine, 4-(diphenylmethyl)piperazine, 4-(2-(bis-(2-propenyl)amino)ethyl)piperazine, 4-(2-(diethylamino)ethyl)piperazine, 4-(2-chlorophenyl)piperazine, 4-(3,4-dimethoxyphenyl)piperazine, 4-(4-nitrophenyl)piperazine, 4-(4-trifluoromethylphenyl)piperazine, 4-hydroxy-4-phenylpiperidine, 4-hydroxypyrrolidine, 4-methylpiperazine, 4-phenylpiperazine, 4-piperidinylpiperazine, 4-((2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, triazole, and the like.

The term "heteroarylalkyl" as used herein, refers to a heteroaryl group as defined above attached to the parent molecular moiety through an alkylene group wherein the alkylene group is of one to four carbon atoms.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, Greene and Wuts, *Protective Groups in Organic Synthesis*, 2nd edition, John Wiley & Sons, New York (1991). Examples of hydroxy-protecting groups include methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reactions during synthetic procedures and to be selectively removable. The use of ketone-protecting groups is well known in the art for protecting groups against undesirable reactions during a synthetic procedure and many such protecting groups are known. See, for examples, Greene and Wuts, *Protective Groups in Organic Synthesis*, 2nd edition, John Wiley & Sons, New York (1991). Examples of ketone-protecting groups include ketals, oximes, O-substituted oximes for example O-benzyl oxime, O-phenylthiomethyl oxime, 1-isopropoxycyclohexyl oxime, and the like.

The term "protected-hydroxy" refers to a hydroxy group protected with a hydroxy protecting group, as defined above, including benzoyl, acetyl, trimethylsilyl, triethylsilyl, methoxymethyl groups, for example.

The term "substituted aryl" as used herein refers to an aryl group as defined herein substituted by independent replacement of one, two or three of the hydrogen atoms thereon with Cl, Br, F, I, OH, CN, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group. Substituted aryl groups also include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, CN, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereoorientations or an individual isomer of assigned or unassigned orientation may be present.

Preferred for the practice of the instant invention are those compounds of formulae I, II, and III wherein X', Y', and Z' combine to form a group R, and R is selected from the group consisting of —(CH$_2$)—C≡C—(5-(2-pyridyl)-2-thienyl),
—(CH$_2$)—C≡C—(5-(3-pyridyl)-2-thienyl),
—(CH$_2$)—C≡C—(5-(4-pyridyl)-2-thienyl),
—(CH$_2$)—C≡C—(5-(5-pyrimidinyl)-2-thienyl),
—(CH$_2$)—C≡C—(5-(2-pyrimidinyl)-2-thienyl),
—(CH$_2$)—C≡C—(5-(2-pyrazinyl)-2-thienyl),
—(CH$_2$)—C≡C—(5-(5-cyano-3-pyridyl)-2-thienyl),
—(CH$_2$)—C≡C—(5-(5-carboxamido-3-pyridyl)-2-thienyl), —(CH₂)—C≡C—(5-(5-ethoxycarbonyl-3-pyridyl)-2-thienyl),
—(CH₂)—C≡C—(5-(5-N,N-dimethylcarboxamido-3-pyridyl)-2-thienyl),
—(CH₂)—C≡C—(5-(5-N',N'-dimethylhydrazidocarbonyl-3-pyridyl)-2-thienyl),
—(CH₂)—C≡C—(5-(phenyl)-2-thienyl),
—(CH₂)—C≡C—(5-(3-methoxyphenyl)-2-thienyl),
—(CH₂)—C≡C—(5-(3-fluorophenyl)-2-thienyl),
—(CH₂)—C≡C—(5-(3-chlorophenyl)-2-thienyl),
—(CH₂)—C≡C—(5-(3,5-dichlorophenyl)-2-thienyl),
—(CH₂)—C≡C—(5-(3-methylphenyl)-2-thienyl),
—(CH₂)—C≡C—(5-(3-trifluoromethylphenyl)-2-thienyl),
—(CH₂)—C≡C—(5-(3-acetamidophenyl)-2-thienyl),
—(CH₂)—C≡C—(5-(3-nitrophenyl)-2-thienyl),
—(CH₂)—C≡C—(5-(4-fluorophenyl)-2-thienyl),
—(CH₂)—C≡C—(5-(2-furanyl)-2-thienyl),
—(CH₂)—C≡C—(4-(5-formyl-2-furanyl)phenyl),
—(CH₂)—C≡C—(4-(5-formyl-2-furanyl)phenyl),
—(CH₂)—C≡C—(4-(5-formyl-2-furanyl)phenyl),
—(CH₂)—C≡C—(2,2'-bisthienyl),
—(CH₂)—C≡C—(2-(5-chloro-2-thienyl)thienyl),
—(CH₂)—C≡C—(2, 3'-bis(thienyl)),
—(CH₂)—C≡C—(5-(2-thiazolyl)-2-thienyl),
—(CH₂)—C≡C—(5-(5-thiazolyl)-2-thienyl),
—(CH₂)—C≡C—(5-(4-thiazolyl)-2-thienyl),
—(CH₂)—C≡C—(5-(2-methyl-5-thiazoyl)-2-thienyl),
—(CH₂)—C≡C—(5-(1-methyl-2-imidazolyl)-2-thienyl),
—(CH₂)—C≡C—(5-(2-quinoxalinyl)-2-thienyl),
—(CH₂)—C≡C—(5-(2-benzothiophenyl)-2-thienyl),
—(CH₂)—C≡C—(5-(2-pyridyl)-2-thienyl),
—(CH₂)—C≡C—(5-(2-benzothiophenyl)-2-thienyl),
—C(H)═CH—(5-(1H-imidazol-1-yl)-3-pyridyl),
—C(H)═CH—(3-(2-furanyl)-6-quinolinyl),
—C(H)═CH—(5-(2-thienyl)-3-pyridyl),
—C(H)═CH—(5-phenyl-3-pyridyl),
—C(H)═CH—(5-(2-pyridyl)-3-pyridyl),
—C(H)═CH—(5-(3-quinolinyl)-3-pyridyl),
—C(H)═CH—(5-(5-pyrimidinyl)-3-pyridyl),
—C(H)═CH—(5-(3-pyridyl)-3-pyridyl),
—C(H) ═CH—(5-(4-isoquinolinyl)-3-pyridyl),
—C(H)═CH—(5-(3-thienyl)-3-pyridyl),
—C(H)═CH—(5-(2-furyl)-3-pyridyl),
—C(H)═CH—(5-(2-(1,3-thiazolyl))-3-pyridyl),
—C(H)═CH—(5-(2-(trimethylsilyl)-1,3-thiazol-5-yl)-3-pyridyl),
—C(H)═CH—(5-(1,3-thiazolyl)-3-pyridyl)
—C(H)═CH—(5-(2-amino-(1,3-thiazol-5-yl))-2-thienyl),
—C(H)═CH—(5-(2-amino-(1,3-thiazol-5-yl))-2-thienyl),
—C(H)═CH—(5-(3-pyridyl)-2-(1,3-thiazolyl)),
—C(H)═CH—(2-(3-pyridyl)-5-(1,3-thiazolyl)),
—C(H)═CH—(2-(5-bromo-1,3-thiazol-2-yl)-5-(1,3-thiazolyl)),
—C(H)═CH—(2-(5-bromo-(1,3-thiazol-2-yl))-5-(1,3-thiazolyl)),
—C(H)═CH—(2-(5-bromo-1,3-thiazol-2-yl)-5-(1,3-thiazolyl)),
—C(H)═CH—(2-(2-thienyl)-5-thiazolyl),
—C(H)═CH—(2-(2-pyrazinyl)-5-(1,3-thiazolyl)),
—C(H)═CH—(2-(5-pyrimidinyl)-5-(1,3-thiazolyl)),
—C(H)═CH—(2-(5-(1,3-thiazol-5-yl)-5-(1,3-thiazolyl)),
—C(H)═CH—(5-(2-pyrimidinyl)-2-thienyl),
—C(H)═CH—(5-(2-pyrazinyl)-2-thienyl),
—C(H)═CH—(5-(2-(1,3-thiazolyl)-2-thienyl),
—C(H)═CH—(5-(4-pyrimidinyl)-2-thienyl),
—C(H)═CH—(4-(3-pyridyl)-2-(1,3-thiazolyl)),
—C(H)═CH—(4-(3-pyridyl)-2-(1,3-thiazolyl)),
—C(H)═CH—(4-(3-pyridyl)-2-(1,3-thiazolyl)),
—C(H)═CH—(4-(2-thienyl)-2-(1,3-thiazolyl)),
—C(H)═CH—(5-(3-pyridyl)-2-thienyl),
—C(H)═CH—(5-(2-pyrazinyl)-2-thienyl),
—C(H)═CH—(5-(5-pyrimidinyl)-2-thienyl),
—C(H)═CH—(5-(3,4-dichlorophenyl)-2-thienyl),
—C(H)═CH—(5-(3-fluorophenyl)-2-thienyl),
—C(H)═CH—(5-(5-(1,3-thiazoyl))-2-thienyl),
—C(H)═CH—(2,2'-bisthienyl),
—C(H)═CH—(5-(2-pyridyl)-2-thienyl),
—C(H)═CH—(5-(3-thienyl)-2-thienyl), and
—C(H)═CH—(5-(2-furanyl)-2-thienyl).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977). The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987.

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1, demonstrate the antibacterial activity of the compounds of the invention.

TABLE 1

MIC's of Selected Compounds

| Microorganism | Organism code | Ery. A standard |
|---|---|---|
| *Staphylococcus aureus* ATCC 6538P | AA | 0.2 |
| *Staphylococcus aureus* A5177 | BB | 3.1 |
| *Staphylococcus aureus* A-5278 | CC | >100 |
| *Staphylococcus aureus* CMX 642A | DD | 0.39 |
| *Staphylococcus aureus* NCTC10649M | EE | 0.39 |
| *Staphylococcus aureus* CMX 553 | FF | 0.39 |
| *Staphylococcus aureus* 1775 | GG | >100 |
| *Staphylococcus epidermidis* 3519 | HH | 0.39 |
| *Enterococcus faecium* ATCC 8043 | II | 0.05 |
| *Streptococcus bovis* A-5169 | JJ | 0.02 |
| *Streptococcus agalactiae* CMX 508 | KK | 0.05 |
| *Streptococcus pyogenes* EES61 | LL | 0.05 |
| *Streptococcus pyogenes* 930 | MM | >100 |
| *Streptococcus pyogenes* PIU 2548 | NN | 6.2 |
| *Micrococcus luteus* ATCC 9341 | OO | 0.05 |
| *Micrococcus luteus* ATCC 4698 | PP | 0.2 |
| *Escherichia coli* JUHL | QQ | >100 |
| *Escherichia coli* SS | RR | 0.78 |
| *Escherichia coli* DC-2 | SS | >100 |
| *Candida albicans* CCH 442 | TT | >100 |
| *Mycobacterium smegmatis* ATCC 114 | UU | 3.1 |
| *Nocardia Asteroides* ATCC9970 | VV | 0.1 |
| *Haemophilis Influenzae* DILL AMP R | WW | 4 |
| *Streptococcus Pneumonia* ATCC6303 | XX | 0.06 |
| *Streptococcus Pneumonia* GYR 1171 | YY | 0.06 |
| *Streptococcus Pneumonia* 5979 | ZZ | >128 |
| *Streptococcus Pneumonia* 5649 | ZZA | 16 |

| Organism code | Example 1 | Example 2 | Example 3 | Example 4 | Example 5 |
|---|---|---|---|---|---|
| AA | 0.05 | 0.05 | 0.05 | 0.1 | 0.02 |
| BB | 0.05 | 0.05 | 0.05 | 0.1 | 0.05 |
| CC | >100 | >100 | >100 | >100 | >100 |
| DD | 0.05 | 0.05 | 0.1 | 0.1 | 0.05 |
| EE | 0.1 | 0.05 | | 0.1 | 0.05 |
| FF | 0.05 | 0.05 | | 0.1 | 0.02 |
| GG | >100 | >100 | | >100 | >100 |
| HH | 0.1 | 0.05 | >100 | 0.1 | 0.05 |
| II | 0.05 | 0.05 | | 0.02 | 0.02 |
| JJ | 0.01 | <=0.005 | <=0.05 | <=0.005 | <=0.005 |
| KK | 0.02 | <=0.005 | <=0.05 | 0.01 | 0.01 |
| LL | 0.02 | 0.01 | <=0.05 | 0.01 | <=0.005 |
| MM | 12.5 | 3.1 | 6.2 | 12.5 | 25 |
| NN | 0.1 | 0.1 | 0.1 | 0.1 | 0.1 |
| OO | 0.02 | <=0.005 | | 0.01 | 0.01 |
| PP | 0.1 | 0.1 | 0.05 | 0.05 | 0.1 |
| QQ | 12.5 | 25 | 100 | 50 | 25 |
| RR | 0.1 | 0.1 | 0.2 | 0.39 | 0.1 |
| SS | 6.2 | 25 | | 50 | 25 |
| TT | >100 | >100 | >100 | >100 | >100 |
| UU | 0.2 | 0.2 | .039 | 0.78 | 0.78 |
| VV | 0.02 | 0.05 | 0.01 | 0.02 | 0.01 |
| WW | 2 | 2 | 2 | 2 | 2 |
| XX | 0.03 | 0.03 | <=0.004 | 0.03 | 0.03 |
| YY | 0.03 | 0.03 | <=0.004 | 0.03 | 0.03 |
| ZZ | 0.25 | 0.25 | 2 | 2 | 0.5 |
| ZZA | 0.25 | 0.12 | 0.125 | 0.5 | 0.25 |

| Organism Code | Example 6 | Example 7 | Example 8 | Example 9 | Example 10 |
|---|---|---|---|---|---|
| AA | 0.05 | 0.05 | 0.05 | 0.1 | 0.1 |
| BB | 0.05 | 0.1 | 0.05 | 0.1 | 0.1 |
| CC | 50 | >100 | >100 | >100 | >100 |
| DD | 0.05 | | 0.05 | 0.1 | 0.1 |
| BB | 0.1 | 0.1 | 0.02 | 0.2 | 0.2 |
| FF | 0.05 | | 0.02 | 0.1 | 0.05 |
| GG | 50 | >100 | >100 | >100 | >100 |
| HH | 0.05 | 0.1 | 0.05 | 0.1 | 0.2 |
| II | 0.02 | | 0.02 | 0.05 | 0.1 |
| JJ | <=0.005 | <=0.005 | <=0.005 | 0.02 | =0.005 |
| KK | 0.01 | <=0.005 | 0.01 | 0.02 | 0.01 |
| LL | 0.02 | 0.02 | <=0.005 | 0.02 | 0.01 |
| MM | 3.1 | 6.2 | 0.2 | 0.2 | 50 |
| NN | 0.1 | 0.2 | 0.1 | 0.2 | 0.2 |
| OO | 0.01 | | <=0.005 | 0.02 | 0.01 |
| PP | 0.1 | 0.2 | 0.05 | 0.1 | 0.2 |
| QQ | 25 | >100 | 50 | 50 | >100 |
| RR | 0.2 | 0.78 | 0.2 | 0.78 | 0.78 |

TABLE 1-continued

MIC's of Selected Compounds

| Organism Code | Example 6 | Example 7 | Example 8 | Example 9 | Example 10 |
|---|---|---|---|---|---|
| SS | 25 | >100 | 50 | >100 | |
| TT | 6.2 | >100 | >100 | >100 | >100 |
| UU | 0.39 | 3.1 | 0.78 | 6.2 | 1.56 |
| VV | 0.01 | <=0.005 | 0.01 | 0.1 | 0.1 |
| WW | 1 | 2 | 4 | 2 | 8 |
| XX | 0.015 | 0.015 | <=0.004 | <=0.004 | 0.03 |
| YY | 0.015 | 0.015 | <=0.004 | <=0.004 | 0.03 |
| ZZ | 0.25 | 2 | 0.25 | 0.03 | 4 |
| ZZA | 0.25 | 0.25 | <=0.004 | 0.25 | 0.5 |

| Organism Code | Example 11 | Example 12 | Example 13 | Example 14 | Example 15 |
|---|---|---|---|---|---|
| AA | 0.1 | 0.39 | 0.39 | 0.1 | 0.1 |
| BB | 0.2 | 0.39 | 0.39 | 0.1 | 0.1 |
| CC | >100 | >100 | >100 | >100 | 50 |
| DD | | | 0.39 | 0.1 | 0.2 |
| EE | 0.2 | 0.39 | 0.78 | 0.1 | 0.2 |
| FF | | | 0.39 | 0.1 | 0.1 |
| GG | >100 | >100 | >100 | 50 | 50 |
| HH | 0.2 | 0.39 | 0.78 | 0.1 | 0.2 |
| II | 0.39 | 0.02 | 0.05 | | |
| JJ | 0.01 | 0.05 | 0.05 | <=0.005 | 0.05 |
| KK | 0.05 | 0.05 | 0.1 | 0.01 | 0.05 |
| LL | 0.02 | 0.05 | 0.02 | 0.01 | 0.05 |
| MM | >100 | 50 | 100 | 1.56 | 3.1 |
| NN | 0.39 | 0.78 | 0.39 | 0.1 | 0.2 |
| OO | | | 0.05 | 0.01 | 0.05 |
| PP | 0.2 | 0.39 | 0.2 | 0.02 | 0.1 |
| QQ | >100 | >100 | >100 | >100 | >100 |
| RR | 0.78 | 0.78 | 3.1 | 0.39 | 0.39 |
| SS | | | >100 | >100 | >100 |
| TT | >100 | >100 | >100 | >100 | >100 |
| UU | >12.5 | 6.2 | 1.56 | 0.2 | 0.39 |
| VV | 0.2 | 0.2 | 0.78 | 0.1 | 0.2 |
| WW | 16 | 16 | 32 | 2 | 2 |
| XX | 0.03 | 0.03 | 0.25 | 0.03 | 0.015 |
| YY | 0.03 | 0.03 | 0.25 | 0.03 | 0.015 |
| ZZ | 128 | 1 | 4 | 1 | 0.25 |
| ZZA | 1 | 1 | 2 | 0.25 | 0.25 |

| Organism Code | Example 16 | Example 17 | Example 18 | Example 19 | Example 20 |
|---|---|---|---|---|---|
| AA | 0.1 | 0.39 | 0.1 | 0.39 | 0.1 |
| BB | 0.2 | 0.78 | 0.1 | 0.39 | 0.05 |
| CC | 25 | 12.5 | 25 | 25 | >100 |
| DD | 0.2 | 0.78 | 0.1 | 0.39 | 0.1 |
| EE | 0.2 | 1.56 | 0.2 | 0.39 | 0.1 |
| FF | 0.2 | 0.78 | 0.1 | 0.39 | 0.1 |
| GG | 12.5 | 12.5 | 12.5 | 12.5 | >100 |
| HH | 0.2 | 0.78 | 0.2 | 0.39 | 0.1 |
| II | 0.1 | 0.78 | 0.1 | 0.39 | 0.05 |
| JJ | 0.02 | 0.2 | 0.01 | 0.05 | <=0.005 |
| KK | 0.02 | 0.2 | 0.02 | 0.05 | <=0.005 |
| LL | 0.1 | 0.39 | 0.02 | 0.1 | 0.02 |
| MM | | 3.1 | 1.56 | 3.1 | 6.2 |
| NN | 0.2 | 0.39 | 0.2 | 0.39 | 0.2 |
| OO | 0.02 | 0.39 | 0.02 | 0.2 | 0.02 |
| PP | 0.2 | 0.78 | 0.2 | 0.39 | 0.1 |
| QQ | >100 | >100 | >100 | >100 | >100 |
| RR | 0.39 | 12.5 | 0.78 | 3.1 | 0.2 |
| SS | >100 | >100 | >100 | >100 | 100 |
| TT | >100 | >100 | >100 | >100 | >100 |
| UU | 0.2 | 0.78 | 0.1 | 0.39 | 1.56 |
| VV | 0.2 | 0.78 | 0.1 | 0.39 | 0.1 |
| WW | 4 | 8 | 2 | 4 | 4 |
| XX | 0.03 | 0.125 | 0.06 | 0.125 | 0.15 |
| YY | 0.03 | 0.125 | 0.03 | 0.125 | 0.015 |
| ZZ | 2 | 1 | 2 | 4 | 0.5 |
| ZZA | 0.25 | 1 | 0.5 | 1 | 0.25 |

| Organism Code | Example 21 | Example 22 | Example 23 | Example 24 | Example 25 |
|---|---|---|---|---|---|
| AA | 0.1 | 3.1 | 0.05 | 0.39 | 0.2 |
| BB | 0.05 | 3.1 | 0.05 | 0.39 | 0.1 |
| CC | >100 | >100 | >100 | >100 | 25 |
| DD | 0.05 | 3.1 | 0.05 | 0.39 | 0.2 |
| EE | 0.1 | 3.1 | 0.05 | 0.39 | 0.2 |
| FF | 0.05 | 3.1 | 0.05 | 0.39 | 0.1 |
| GG | 100 | >100 | >100 | >100 | 25 |
| HH | 0.2 | 3.1 | 0.05 | 0.39 | 0.1 |
| II | 0.05 | 0.78 | 0.02 | 0.2 | 0.1 |
| JJ | 0.02 | 0.39 | 0.01 | 0.1 | 0.1 |
| KK | 0.02 | 0.39 | <=0.005 | 0.1 | 0.1 |
| LL | 0.02 | 0.39 | 0.1 | 0.1 | 0.005 |
| MM | 0.78 | >100 | 6.2 | 25 | 1.56 |
| NN | 0.2 | 3.1 | 0.1 | 0.78 | 0.2 |
| OO | 0.02 | 0.39 | 0.01 | 0.02 | 0.05 |
| PP | 0.05 | 3.1 | 0.05 | 0.39 | 0.2 |
| QQ | >100 | >100 | 50 | >100 | 100 |
| RR | 0.2 | 25 | 0.39 | 1.56 | 0.2 |
| SS | >100 | >100 | 50 | >100 | >100 |
| TT | >100 | >100 | >100 | >100 | 12.5 |
| UU | 0.2 | 1.56 | 0.78 | 3.1 | 0.39 |
| VV | 0.2 | 0.78 | 0.02 | 0.1 | 0.39 |
| WW | 8 | 64 | 2 | 8 | 2 |
| XX | 0.03 | 1 | 0.03 | 0.03 | <=0.004 |
| YY | 0.03 | 1 | 0.03 | 0.03 | <=0.004 |
| ZZ | 2 | 4 | 8 | 2 | 0.25 |
| ZZA | 0.5 | 4 | 0.25 | 0.25 | 0.125 |

| Organism Code | Example 26 | Example 27 | Example 28 | Example 29 | Example 30 |
|---|---|---|---|---|---|
| AA | 0.2 | 0.05 | 0.05 | 0.05 | 0.02 |
| BB | 0.2 | 0.05 | 0.05 | 0.05 | 0.02 |
| CC | 12.5 | 100 | >100 | >100 | >100 |
| DD | 0.2 | 0.05 | 0.05 | 0.05 | |
| EE | 0.2 | 0.05 | 0.1 | 0.02 | 0.05 |
| FF | 0.2 | 0.05 | 0.05 | 0.02 | |
| GG | 12.5 | 5o | >100 | >100 | >100 |
| HH | 0.2 | 0.05 | 0.05 | 0.05 | 0.05 |
| II | 0.1 | 0.01 | 0.05 | 0.01 | |
| JJ | 0.05 | <=0.005 | <=0.005 | <=0.005 | <=0.005 |
| KK | <=0.005 | <=0.005 | 0.02 | 0.01 | 0.02 |
| LL | 0.02 | <=0.005 | <=0.005 | 0.01 | 0.02 |
| MM | 3.1 | 6.2 | 12.5 | 3.1 | 6.2 |
| NN | 0.2 | 0.1 | 0.1 | 0.05 | 0.1 |
| OO | 0.05 | <=0.005 | 0.01 | <=0.005 | |
| PP | 0.2 | 0.05 | 0.1 | 0.05 | 0.1 |
| QQ | >100 | 100 | 25 | 25 | 12.5 |
| RR | 1.56 | 0.2 | 0.1 | 0.1 | 0.1 |
| SS | >100 | 100 | 12.5 | 50 | |
| TT | >100 | >100 | >100 | >100 | >100 |
| UU | 0.39 | 0.2 | 0.2 | 0.39 | 0.39 |
| VV | 0.1 | 0.01 | 0.05 | <=0.005 | 0.01 |
| WW | 4 | 2 | 2 | 2 | 2 |
| XX | 0.03 | 0.015 | 0.03 | <=0.004 | <=0.004 |
| YY | 0.03 | 0.015 | 0.03 | <=0.004 | <=0.004 |
| ZZ | 0.5 | 4 | 1 | 1 | 1 |
| ZZA | 0.25 | 0.25 | 0.25 | 0.25 | 0.25 |

| Organism Code | Example 31 | Example 32 | Example 33 | Example 34 | Example 35 |
|---|---|---|---|---|---|
| AA | 0.1 | 0.05 | 0.2 | 0.39 | 0.05 |
| BB | 0.2 | 0.05 | 0.2 | 0.2 | 0.1 |
| CC | >100 | >100 | 25 | 50 | >100 |
| DD | 0.2 | 0.05 | 0.2 | 0.39 | |
| EE | 0.2 | 0.1 | 0.39 | 0.2 | 0.2 |
| FF | 0.1 | 0.05 | 0.2 | 0.2 | |
| GG | >100 | >100 | 50 | 12.5 | >100 |
| HH | 0.2 | 0.1 | 0.2 | 0.39 | 0.1 |
| II | 0.05 | 0.02 | 0.05 | 0.2 | |
| JJ | 0.05 | <=0.005 | 0.01 | 0.02 | 0.01 |
| KK | 0.02 | 0.01 | 0.01 | 0.02 | 0.05 |
| LL | 0.02 | 0.01 | 0.02 | 0.02 | 0.02 |
| MM | 12.5 | 12.5 | 0.39 | 1.56 | 6.2 |

TABLE 1-continued

MIC's of Selected Compounds

| Organism Code | | | | | |
|---|---|---|---|---|---|
| NN | 0.2 | 0.39 | 0.2 | 0.39 | 0.2 |
| OO | 0.02 | 0.01 | 0.05 | 0.02 | |
| PP | 0.2 | 0.05 | 0.05 | 0.2 | 0.2 |
| QQ | 100 | 50 | >100 | >100 | 25 |
| RR | 0.2 | 0.2 | 0.78 | 1.56 | 0.39 |
| SS | 100 | >100 | >100 | >100 | |
| TT | >100 | >100 | >100 | >100 | >100 |
| UU | 0.2 | 1.56 | 0.2 | 0.39 | 0.2 |
| VV | 0.05 | 0.01 | 0.1 | 0.39 | 0.02 |
| WW | 2 | 2 | 4 | 16 | 4 |
| XX | <=0.004 | 0.03 | 0.03 | 0.25 | <=0.004 |
| YY | <=0.004 | 0.03 | 0.03 | 0.25 | <=0.004 |
| ZZ | 16 | 0.25 | 0.25 | 8 | 4 |
| ZZA | 0.25 | 0.25 | 0.25 | 2 | 0.25 |

| Organism Code | Example 36 | Example 37 | Example 38 | Example 39 | Example 40 |
|---|---|---|---|---|---|
| AA | 0.05 | 0.1 | 0.2 | 0.2 | 0.1 |
| BB | 0.05 | 0.1 | 0.2 | 0.2 | 0.2 |
| CC | >100 | >100 | 100 | >100 | >100 |
| DD | | 0.1 | 0.2 | 0.2 | 0.2 |
| BE | 0.1 | 0.2 | 0.2 | 0.2 | 0.2 |
| FF | | 0.1 | 0.2 | 0.2 | 0.2 |
| GG | >100 | >100 | 100 | >100 | >100 |
| HH | 0.1 | 0.1 | 0.2 | 0.2 | 0.2 |
| II | | 0.05 | 0.05 | 0.1 | 0.05 |
| JJ | <=0.005 | 0.01 | <=0.005 | 0.01 | 0.02 |
| KK | <=0.005 | 0.02 | 0.02 | 0.01 | 0.02 |
| LL | 0.01 | 0.02 | 0.02 | 0.01 | 0.02 |
| MM | 50 | 25 | 3.1 | 6.2 | 50 |
| NN | 0.39 | 0.39 | 0.2 | 0.2 | 0.1 |
| OO | | 0.01 | 0.05 | 0.02 | 0.02 |
| PP | 0.1 | 0.2 | 0.2 | 0.2 | 0.2 |
| QQ | 25 | 50 | 100 | >100 | 100 |
| RR | 0.2 | 0.39 | 0.78 | 0.78 | 0.39 |
| SS | | 50 | >100 | >100 | 50 |
| TT | >100 | >100 | >100 | >100 | >100 |
| UU | 1.56 | 3.1 | 0.39 | 0.39 | 0.39 |
| VV | 0.01 | 0.1 | 0.05 | 0.1 | 0.1 |
| WW | 2 | 4 | 2 | 4 | 4 |
| XX | 0.015 | <=0.004 | 0.03 | 0.06 | 0.015 |
| YY | 0.015 | <=0.004 | 0.03 | 0.03 | 0.015 |
| ZZ | 2 | >128 | 2 | 2 | >128 |
| ZZA | 0.25 | 2 | 0.25 | 0.25 | 0.25 |

| Organism Code | Example 42 | Example 43 | Example 44 | Example 45 | Example 46 |
|---|---|---|---|---|---|
| AA | 0.1 | 0.05 | 0.1 | 0.05 | 0.1 |
| BB | 0.1 | 0.05 | 0.1 | 0.05 | 0.2 |
| CC | >100 | >100 | >100 | >100 | >100 |
| DD | 0.2 | 0.1 | 0.1 | 0.1 | 0.2 |
| BB | 0.2 | 0.2 | 0.2 | 0.2 | 0.2 |
| FF | 0.1 | 0.05 | 0.05 | 0.05 | 0.2 |
| GG | >100 | >100 | >100 | >100 | >100 |
| HH | 0.2 | 0.1 | 0.1 | 0.1 | 0.1 |
| II | 0.05 | 0.05 | 0.05 | 0.05 | 0.05 |
| JJ | 0.02 | 0.02 | 0.01 | <=0.005 | 0.01 |
| KK | 0.02 | 0.05 | 0.05 | <=0.005 | 0.02 |
| LL | 0.02 | 0.02 | 0.01 | <=0.005 | 0.02 |
| MM | 50 | 25 | 6.2 | 25 | 12.5 |
| NN | 0.2 | 0.2 | 0.1 | 0.39 | 0.2 |
| OO | 0.02 | 0.02 | 0.01 | 0.01 | 0.05 |
| PP | 0.2 | 0.2 | 0.1 | 0.1 | 0.2 |
| QQ | 100 | 50 | 100 | 50 | 50 |
| RR | 0.78 | 0.39 | 0.2 | 0.39 | 0.39 |
| SS | 50 | 25 | 50 | 25 | 100 |
| TT | >100 | >100 | >100 | >100 | >100 |
| UU | 0.39 | 0.78 | 0.39 | 1.56 | 6.2 |
| VV | 0.2 | 0.05 | 0.1 | 0.05 | 0.05 |
| WW | 4 | 2 | 2 | 2 | 4 |
| XX | 0.03 | <=0.004 | <=0.004 | 0.008 | 0.03 |
| YY | 0.03 | <=0.004 | <=0.004 | <=0.004 | 0.03 |
| ZZ | 32 | 64 | 8 | >128 | 128 |
| ZZA | | | | | 0.5 |

| Organism Code | Example 47 | Example 48 | Example 49 | Example 50 | Example 51 |
|---|---|---|---|---|---|
| AA | 0.05 | 0.2 | 0.1 | 0.05 | 0.1 |
| BB | 0.05 | 0.2 | 0.05 | 0.02 | 0.05 |
| CC | >100 | >100 | >100 | >100 | >100 |
| DD | 0.05 | 0.2 | 0.1 | 0.05 | 0.1 |
| EE | 0.1 | 0.2 | 0.1 | 0.1 | 0.1 |
| FF | 0.05 | 0.2 | 0.05 | 0.02 | 0.1 |
| GG | >100 | >100 | >100 | >100 | >100 |
| HH | 0.1 | 0.2 | 0.1 | 0.05 | 0.1 |
| II | 0.05 | 0.05 | 0.05 | 0.05 | 0.05 |
| JJ | 0.01 | 0.02 | 0.02 | 0.01 | 0.01 |
| KK | 0.01 | 0.02 | 0.02 | 0.01 | 0.01 |
| LL | 0.02 | 0.05 | 0.02 | 0.02 | 0.02 |
| MM | 50 | 100 | 25 | 12.5 | 6.2 |
| NN | 0.2 | 0.2 | 0.2 | 0.1 | 0.2 |
| OO | 0.01 | 0.05 | 0.02 | 0.01 | 0.01 |
| PP | 0.2 | 0.1 | 0.05 | 0.1 | 0.2 |
| QQ | 50 | >100 | 50 | 25 | 100 |
| RR | 0.39 | 0.78 | 0.39 | 0.39 | 0.2 |
| SS | 25 | >100 | 50 | 50 | 25 |
| TT | >100 | >100 | >100 | >100 | >100 |
| UU | 0.78 | 0.78 | 0.39 | 0.39 | 0.39 |
| VV | 0.05 | 0.05 | 0.05 | 0.05 | 0.05 |
| WW | | | | 2 | 2 |
| XX | 0.008 | <=0.004 | <=0.004 | <=0.004 | <=0.004 |
| YY | 0.008 | <=0.004 | <=0.004 | <=0.004 | <=0.004 |
| ZZ | >128 | 16 | 32 | 128 | >128 |
| ZZA | 0.5 | 0.25 | 0.03 | 0.12 | 0.25 |

| Organism Code | Example 52 | Example 53 | Example 54 | Example 55 | Example 56 |
|---|---|---|---|---|---|
| AA | 0.05 | 0.1 | 0.05 | 0.1 | 0.2 |
| BB | 0.05 | 0.1 | 0.05 | 0.05 | 0.2 |
| CC | >100 | >100 | >100 | >100 | 100 |
| DD | 0.05 | 0.1 | 0.05 | 0.05 | 0.2 |
| EE | 0.05 | 0.1 | 0.1 | 0.1 | 0.39 |
| FF | 0.05 | 0.1 | 0.05 | 0.05 | 0.2 |
| GG | >100 | >100 | >100 | >100 | 50 |
| HH | 0.05 | 0.1 | 0.05 | 0.1 | 0.2 |
| II | 0.01 | 0.05 | 0.02 | 0.05 | 0.05 |
| JJ | 0.01 | 0.01 | <=0.005 | <=0.005 | 0.05 |
| KK | <=0.005 | 0.01 | <=0.005 | 0.05 | 0.05 |
| LL | 0.02 | <=0.005 | <=0.005 | 0.05 | 0.05 |
| MM | 100 | 12.5 | 100 | 25 | 5o |
| NN | 0.1 | 0.1 | 0.1 | 0.2 | 0.39 |
| OO | 0.01 | 0.01 | 0.01 | 0.02 | 0.05 |
| PP | 0.2 | 0.1 | 0.05 | 0.2 | 0.39 |
| QQ | 100 | 50 | 1.56 | 50 | >10.0 |
| RR | 0.39 | 0.2 | 0.2 | 0.39 | 0.78 |
| SS | 25 | 25 | 25 | 50 | >100 |
| TT | >100 | >100 | >100 | >100 | >100 |
| UU | 1.56 | 3.1 | 3.1 | 0.39 | 0.39 |
| VV | 0.02 | 0.1 | 0.01 | 0.02 | 0.39 |
| WW | 2 | 8 | 2 | 4 | 8 |
| XX | <=0.004 | 0.03 | 0.03 | 0.03 | 0.015 |
| YY | <=0.004 | 0.03 | 0.03 | 0.03 | 0.015 |
| ZZ | >128 | 16 | 4 | 2 | 4 |
| ZZA | 0.25 | 1 | 0.25 | 0.25 | 0.25 |

| Organism Code | Example 57 | Example 58 | Example 59 | Example 60 | Example 61 |
|---|---|---|---|---|---|
| AA | 0.1 | 0.1 | 0.1 | 0.1 | 0.05 |
| BB | 0.05 | 0.05 | 0.1 | 0.05 | 0.1 |
| CC | >100 | >100 | >100 | >100 | >100 |
| DD | 0.05 | 0.1 | 0.1 | 0.05 | 0.1 |
| EE | 0.2 | 0.1 | 0.1 | 0.1 | 0.1 |
| FF | 0.1 | 0.05 | 0.1 | 0.05 | 0.1 |
| GG | 100 | >100 | >100 | >100 | >100 |
| HH | 0.05 | 0.1 | 0.1 | 0.1 | 0.1 |
| II | 0.05 | 0.02 | 0.02 | 0.02 | 0.05 |
| JJ | 0.02 | 0.01 | <=0.005 | <=0.005 | 0.01 |
| KK | 0.01 | 0.02 | 0.01 | 0.01 | 0.01 |
| LL | 0.01 | 0.02 | 0.01 | 0.01 | 0.01 |

TABLE 1-continued

MIC's of Selected Compounds

| Organism Code | Example 62 | Example 63 | Example 64 | Example 65 | Example 66 |
|---|---|---|---|---|---|
| MM | 25 | 3.1 | 6.2 | 3.1 | 50 |
| NN | 0.1 | 0.1 | 0.2 | 0.2 | 0.1 |
| OO | 0.02 | 0.01 | 0.01 | <=0.005 | 0.01 |
| PP | 0.05 | 0.05 | 0.1 | 0.02 | 0.05 |
| QQ | 100 | 50 | 50 | 50 | 25 |
| RR | 0.39 | 0.2 | 0.2 | 0.2 | 0.39 |
| SS | 100 | 100 | 50 | 100 | 50 |
| TT | >100 | >100 | >100 | >100 | >100 |
| UU | 0.2 | 1.56 | 3.1 | 1.56 | 0.39 |
| VV | 0.05 | 0.02 | 0.02 | 0.01 | 0.05 |
| WW | 4 | 4 | 4 | 4 | 8 |
| XX | <=0.004 | <=0.004 | <=0.004 | <=0.004 | 0.015 |
| YY | <=0.004 | <=0.004 | <=0.004 | <=0.004 | 0.015 |
| ZZ | 0.5 | 4 | 4 | 1 | 8 |
| ZZA | 0.25 | 0.25 | 0.5 | 0.25 | 0.25 |

| Organism Code | Example 62 | Example 63 | Example 64 | Example 65 | Example 66 |
|---|---|---|---|---|---|
| AA | 0.05 | 0.1 | 0.05 | 0.1 | 0.1 |
| BB | 0.05 | 0.1 | 0.05 | 0.1 | 0.1 |
| CC | >100 | >100 | >100 | >100 | >100 |
| DD | 0.05 | 0.1 |  | 0.1 | 0.1 |
| EE | 0.02 | 0.1 | 0.05 | 0.1 | 0.1 |
| FF | 0.02 | 0.1 |  | 0.1 | 0.1 |
| GG | >100 | >100 | >100 | >100 | >100 |
| HH | 0.05 | 0.2 | 0.05 | 0.1 | 0.1 |
| II | 0.02 | 0.05 |  | 0.02 | 0.05 |
| JJ | <=0.005 | 0.05 | <=0.005 | <=0.005 | 0.01 |
| KK | <=0.005 | 0.05 | 0.02 | 0.01 | 0.01 |
| LL | <=0.005 | 0.05 | 0.01 | 0.01 | 0.01 |
| MM | 3.1 | 6.2 | 3.1 | 50 | >100 |
| NN | 0.1 | 0.2 | 0.1 | 0.1 | 0.2 |
| OO | <=0.005 | 0.05 |  | 0.02 | 0.01 |
| PP | 0.05 | 0.1 | 0.2 | 0.1 | 0.1 |
| QQ | 50 | 100 | 50 | 100 | 50 |
| RR | 0.2 | 0.1 | 0.39 | 0.2 | 0.2 |
| SS | 25 | 100 |  | 25 | 25 |
| TT | >100 | >100 | >100 | >100 | >100 |
| UU | 0.78 | 0.39 | 0.78 | 0.78 | 0.78 |
| VV | <=0.005 | 0.05 | 0.01 | 0.02 |  |
| WW | 2 | 4 | 2 | 2 | 8 |
| XX | <=0.004 | 0.008 | <=0.004 | 0.008 | 0.008 |
| YY | <=0.004 | 0.008 | <=0.004 | <=0.004 | 0.008 |
| ZZ | 2 | 8 | 2 | >128 | >64 |
| ZZA | 0.03 | 0.25 | 0.25 | 0.25 | 0.25 |

| Organism Code | Example 67 | Example 68 | Example 70 | Example 71 | Example 72 |
|---|---|---|---|---|---|
| AA | 0.1 | 0.2 | 0.1 | 0.39 | 0.2 |
| BB | 0.1 | 6.2 | 0.2 | 0.39 | 0.2 |
| CC | >100 | >100 | >100 | 12.5 | 25 |
| DD | 0.1 | 0.39 | 0.1 | 0.39 | 0.2 |
| EE | 0.1 | 0.39 | 0.2 | 0.39 | 0.2 |
| FF | 0.1 | 0.39 | 0.1 | 0.39 | 0.2 |
| GG | >100 | >100 | >100 | 12.5 | 25 |
| HH | 0.1 | 0.39 | 0.1 | 0.39 | 0.2 |
| II | 0.05 | 0.05 | 0.05 | 0.39 | 0.05 |
| JJ | 0.01 | 0.02 | 0.01 | 0.05 | <=0.005 |
| KK | 0.01 | 0.02 | 0.02 | 0.1 | 0.01 |
| LL | 0.01 | 0.05 | 0.01 | 0.1 |  |
| MM | 12.5 | >100 | 12.5 | 3.1 | 12.5 |
| NN | 0.1 | 6.2 | 0.1 | 0.39 | 0.39 |
| OO | 0.02 | 0.02 | 0.02 | 0.39 | 0.02 |
| PP | 0.1 | 0.39 | 0.1 | 0.39 | 0.05 |
| QQ | >100 | 100 | 100 | >100 | >100 |
| RR | 0.78 | 0.39 | 0.78 | 3.1 | 1.56 |
| SS | >100 | >100 | 100 | >100 | >100 |
| TT | >100 | >100 | >100 | >100 | >100 |
| UU | 0.39 | 3.1 | 0.39 | 0.39 | 1.56 |
| VV | 0.1 | 0.05 | 0.02 | 0.39 | 0.39 |
| WW | 8 | 2 | 4 | 16 | 8 |
| XX | 0.03 | <=0.004 | 0.015 | 0.125 | 0.125 |
| YY | 0.03 | <=0.004 | 0.015 | 0.125 | 0.125 |
| ZZ | 32 | 0.125 | 4 | 4 | 4 |
| ZZA | 0.25 | 0.125 | 0.25 | 1 | 1 |

| Organism Code | Example 73 | Example 74 | Example 75 | Example 76 | Example 77 |
|---|---|---|---|---|---|
| AA | 0.05 | 0.1 | 0.05 | 0.1 | 0.1 |
| BB | 0.05 | 0.1 | 0.05 | 0.1 | 0.1 |
| CC | >100 | 50 | >100 | 100 | 100 |
| DD | 0.05 | 0.1 | 0.05 | 0.1 | 0.1 |
| EE | 0.1 | 0.2 | 0.05 | 0.05 | 0.1 |
| FF | 0.02 | 0.1 | 0.05 | 0.1 | 0.1 |
| GG | >100 | 25 | >100 | 100 | 100 |
| HH | 0.1 | 0.1 | 0.05 | 0.1 | 0.1 |
| II | 0.02 | 0.02 | 0.05 | 0.02 | 0.05 |
| JJ | <=0.005 | 0.02 | 0.01 | <=0.005 | 0.01 |
| KK | 0.01 | <=0.005 | 0.02 | 0.01 | 0.02 |
| LL | 0.02 | 0.01 | 0.02 | 0.01 | 0.05 |
| MM | 12.5 | >100 | 12.5 | 3.1 | 12.5 |
| NN | 0.1 | 0.1 | 0.1 | 0.1 | 0.2 |
| OO | <=0.005 | 0.02 | 0.02 | 0.05 | 0.02 |
| PP | 0.1 | 0.1 | 0.1 | 0.2 | 0.2 |
| QQ | 50 | 100 | 50 | 100 | 50 |
| RR | 0.1 | 0.39 | 0.39 | 0.2 | 0.39 |
| SS | 100 | >100 | 25 | 100 | 50 |
| TT | >100 | >100 | >100 | >100 | >100 |
| UU | 0.39 | 0.39 | 1.56 | 0.78 | 0.78 |
| VV | 0.02 | 0.1 | 0.02 | 0.1 | 0.2 |
| WW | 2 | 4 | 2 | 8 | 8 |
| XX | 0.03 | <=0.004 | <=0.004 | <=0.004 | <=0.004 |
| YY | 0.015 | <=0.004 | <=0.004 | <=0.004 | <=0.004 |
| ZZ | 2 | 2 | 1 | 16 | 16 |
| ZZA | 0.25 | 0.25 | 0.125 | 0.125 | 0.25 |

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eyd ns are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

Abbreviations used in the Schemes and Examples include the following: Ac for acetate; dba for dibenzylidine acetone; THF for tetrahydrofuran; DME for dimethoxy ethane; DMF for N,N-dimethylformamide; TFA for trifluoroacetic acid; DMSO for dimethylsulfoxide; and TMS for trimethylsilyl. Starting materials, reagents and solvents were purchased from Aldrich Chemical Company (Milwaukee, Wis.).

The compounds and processes of the present invention will be better understood in connection with the following synthetic Schemes, which illustrate the methods by which the compounds of the invention may be prepared. The compounds of formulae I, II, and III may be prepared by a variety of synthetic routes. Representative procedures are shown below in Schemes 1–12. The groups R, $R^b$, L, and T, are as previously defined unless otherwise noted. It will be readily apparent to one of ordinary skill in the art that other compounds within formulae I, II, and III can be synthesized by substitution of the appropriate reactants and agents in the syntheses shown below. It will also be apparent to one skilled in the art that the selective protection and deprotection steps, as well as the order of the steps themselves, can be carried out in varying order, depending on the nature of groups R, $R^p$, L, and T, in order to successfully complete the syntheses of compounds of formulae I, II, and III.

The conversion of erythromycin A to 1 is described in U.S. Pat. Nos. 4,990,602; 4,331,803; 4,680,368, and 4,670,549 and European Patent Application EP 260,938, the disclosures of each of which are herein incorporated by reference. Briefly, the C-9-carbonyl of erythromycin A can be protected as an oxime. Preferred protecting groups at the C-9-carbonyl are $=\!N\!\!-\!\!O\!\!-\!\!R^x$ or $=\!N\!\!-\!\!O\!\!-\!\!C(R^y)(R^z)(\!\!-\!\!O\!\!-\!\!R^x)$, wherein $R^x$ is (a) $C_1$–$C_{12}$-alkyl, (b) $C_1$–$C_{12}$-alkyl substituted with aryl, (c) $C_1$–$C_{12}$-alkyl substituted with substituted aryl, (d) $C_1$–$C_{12}$-alkyl substituted with heteroaryl, (e) $C_1$–$C_{12}$-alkyl substituted with substituted heteroaryl, (f) $C_3$–$C_{12}$-cycloalkyl, or (g) $-\!\!Si\!\!-\!\!(R^d)(R^e)(R^f)$, wherein $R^d$, $R^e$ and $R^f$ are $C_1$–$C_{12}$-alkyl or $-\!\!Si(aryl)_3$, and wherein $R^y$ and $R^z$ are independently (a) hydrogen, (b) $C_1$–$C_{12}$-alkyl, (c) $C_1$–$C_{12}$-alkyl substituted with aryl, or (d) $C_1$–$C_{12}$-alkyl substituted with substituted aryl, or $R^y$ and $R^z$ taken together with the carbon to which they are attached form a $C_3$–$C_{12}$-cycloalkyl ring. A preferred carbonyl protecting group is O-(1-isopropoxycyclohexyl) oxime.

The 2'- and 4"-hydroxy groups of the C-9 protected erythromycin A can be treated with a hydroxy protecting group precursor in an aprotic solvent. Hydroxy protecting group precursors include, acetic anhydride, benzoic anhydride, benzyl chloroformate, hexamethyldisilazane, or a trialkylsilyl halide. Examples of aprotic solvents include dichloromethane, chloroform, THF, N-methyl pyrrolidinone, DMSO, diethylsulfoxide, DMF, N,N-dimethylacetamide, hexamethylphosphoric triamide, mixtures thereof, and mixtures of one of these solvents with ether, tetrahydrofuran, 1,2-dimethoxyethane, acetonitrile, ethyl acetate, or acetone. Aprotic solvents do not adversely affect the reaction and are preferably dichloromethane, chloroform, DMF, tetrahydrofuran (THF), N-methyl pyrrolidinone, or mixtures thereof. Protection of the 2'- and 4"-hydroxy groups of the C-9 protected erythromycin A may be accomplished sequentially or simultaneously. Preferred protecting groups include acetyl, benzoyl, and trimethylsilyl. An especially preferred protecting group is trimethylsilyl. A thorough discussion of protecting groups and the solvents in which they are most effective is provided in Greene and Wuts in *Protective Groups in Orqanic Synthesis*, 2nd ed., John Wiley & Son, Inc., 1991.

Scheme 1

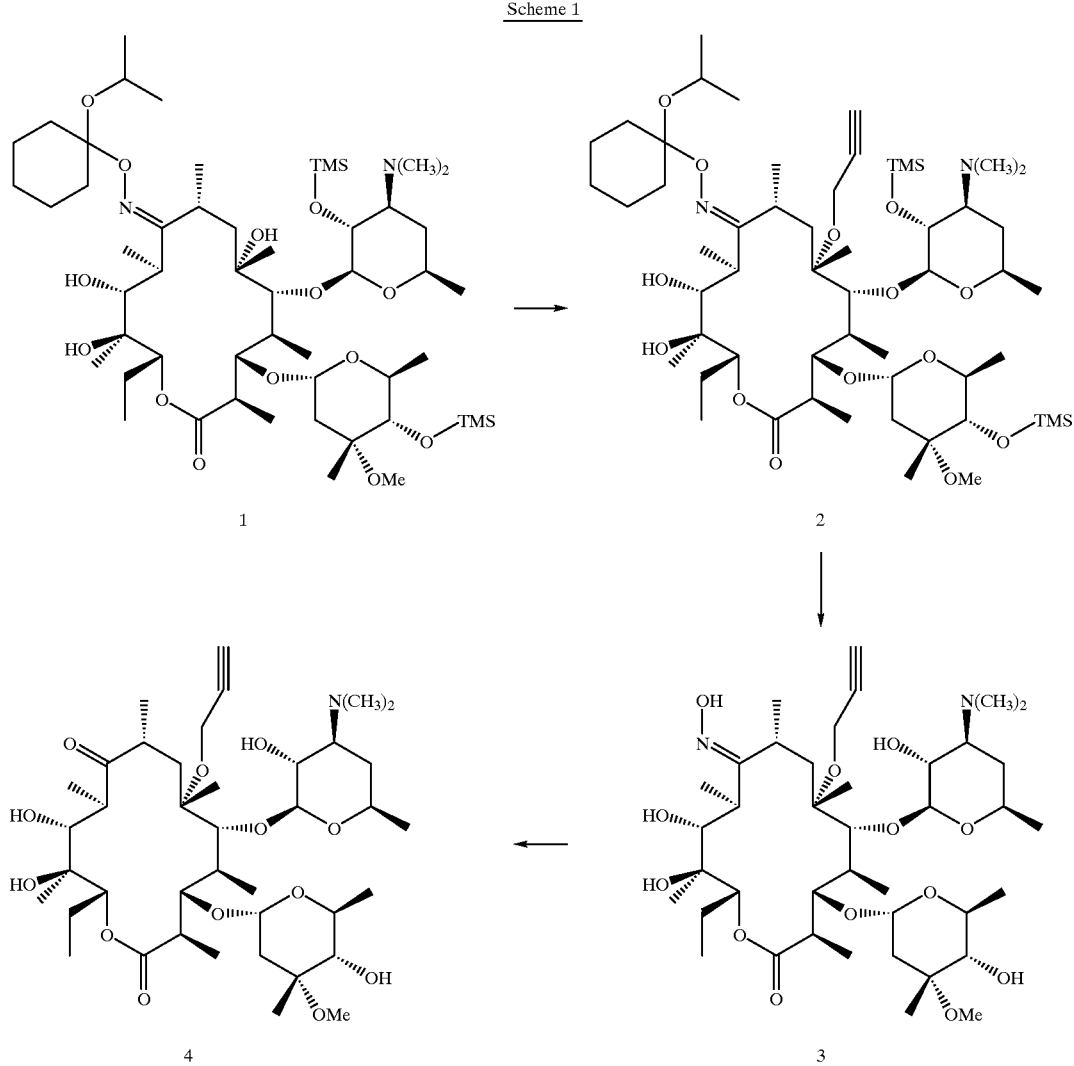

As shown in Scheme 1, conversion of alcohol 1 to ether 2 can be accomplished with an alkylating agent in the presence of base. Alkylating agents include alkyl chlorides, bromides, iodides or alkyl sulfonates. Specific examples of other alkylating agents are allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, and 1,3-dibromo-1-propene. Examples of alkyl sulfonates are allyl tosylate, 3-phenylpropyl trifluoromethane sulfonate, and n-butylmethanesulfonate. Examples of the solvents used are aprotic solvents such as (DMSO), diethylsulfoxide, N,N-dimethylformamide, N,N-dimethylacetamide, N-methyl-2-pyrrolidone, hexamethylphosphoric triamide, mixtures thereof or mixtures of one of these solvents with ether, tetrahydrofuran, 1,2-dimethoxyethane, acetonitrile, ethyl acetate, or acetone. Examples of the base which can be used are potassium hydroxide, cesium hydroxide, tetraalkylammonium hydroxide, sodium hydride, potassium hydride, and alkali metal alkoxides such as potassium isopropoxide, potassium tert-butoxide, and potassium iso-butoxide. An especially preferred method of preparing 2 was treatment of alcohol 1 with propargyl bromide in a DMSO/THF mixture with potassium hydroxide as the base. The conversion of 2 to 3 can be accomplished as described in Greene. The preferred conditions for the deprotection of the 2'- and 4"-hydroxyl groups (acetic acid in acetonitrile and water) can result in concomitant removal of the 1-isopropoxycyclohexyl group provide an unalkylated oxime (=N—OH) at C-9. If not, then the conversion can be accomplished in a separate step. The deoximation of 3 to provide Intermediate 4 can be accomplished as described in Greene. Examples of deoximating agents are nitrous acid (formed in situ by the reaction of sodium nitrite with acids such as HCl, $H_2SO_4$, and TFA) and inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, and potassium metabisulfite in an protic solvent. Examples of protic solvents are water, methanol, ethanol, propanol, isopropanol, trimethylsilanol, or mixtures thereof. The deoximation reaction can also be accomplished with an organic acid such as formic acid, acetic acid and TFA. The amount of acid used is from about 1 to about 10 equivalents per equivalent of 3. In a preferred embodiment, the deoximation was carried out using sodium nitrite and an inorganic acid such as HCl in ethanol and water to provide the desired 6-O-substituted erythromycin Intermediate 4, wherein R is propargyl.

bonyldiimidazole in an aprotic solvent for about 8 to about 24 hours at temperatures of about −30° C. to about room temperature to provide 6. The alkali metal may be sodium potassium or lithium and the aprotic solvent can be one defined previously. The reaction may require cooling or heating from about −20° C. to about 70° C., depending on the conditions used, and preferably from about 0° C. to about room temperature. The reaction requires about 0.5 hours to about 10 days, and preferably about 10 hours to 2 days to complete. Portions of this reaction sequence follow the

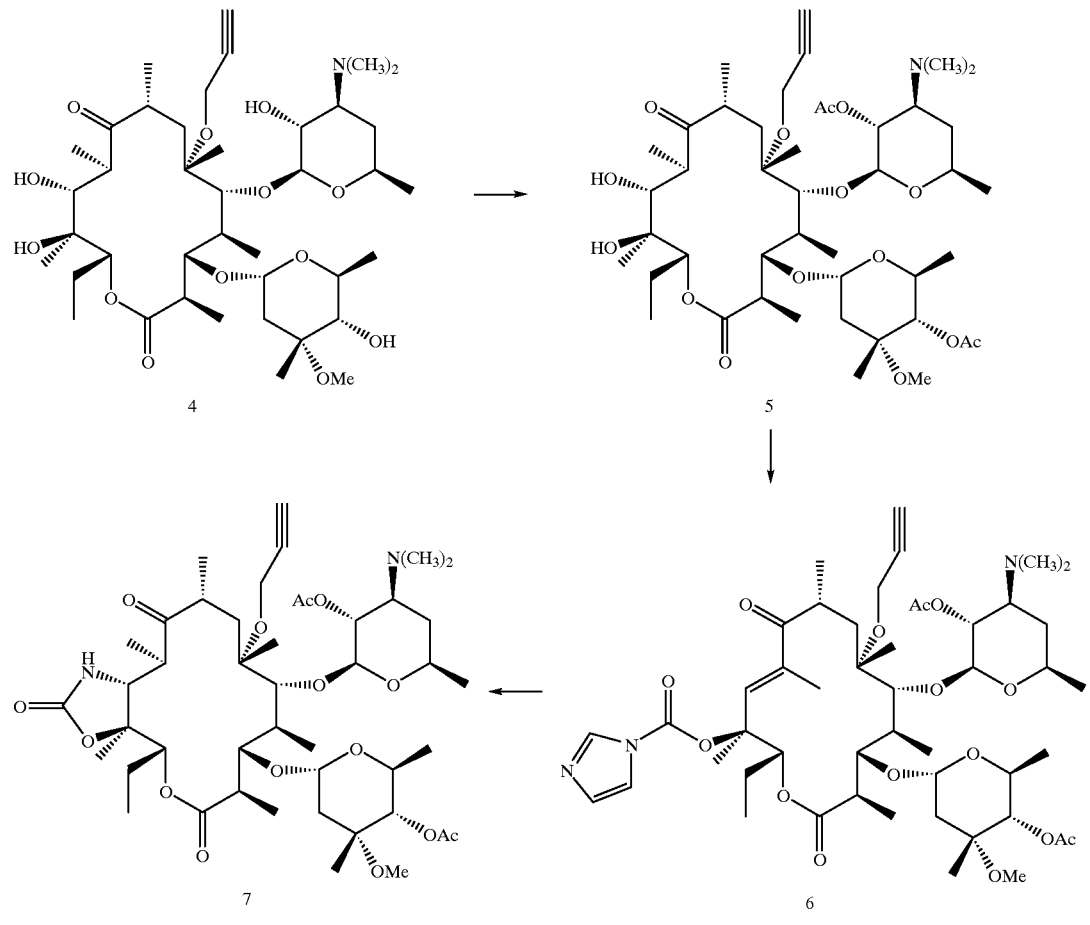

As shown in Scheme 2, conversion of 4 to Intermediate 5 can be accomplished by the 2′- and 4″-hydroxy group protection procedures described previously. Conversion of 5 to 6 can be accomplished with an excess of an alkali metal hydride or bis(trimethylsilyl)amide in the presence of carprocedure described by Baker et al., *J. Org. Chem.*, 1988, 53, 2340 the disclosure of which is herein incorporated by reference. Conversion of 6 to cyclic carbamate 7, a precursor of compounds of formula I, was accomplished by treatment of 6 with liquid ammonia at room temperature for 20 hours.

Scheme 3

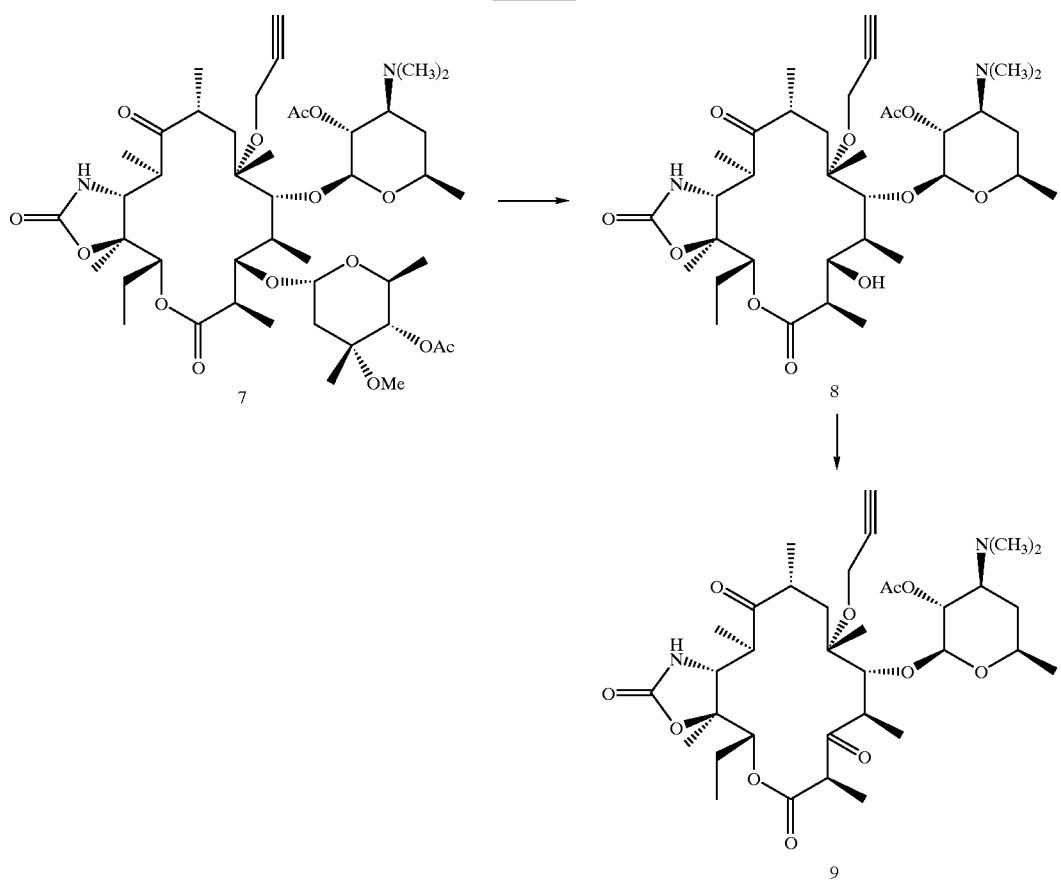

As shown in Scheme 3, 7 can be converted to 8 by hydrolysis of the former with mild aqueous acid or by enzymatic hydrolysis to remove the cladinose moiety from the 3-hydroxy group. Representative acids include dilute hydrochloric acid, sulfuric acid, perchloric acid, chloroacetic acid, dichloroacetic acid, or TFA. Suitable solvents for the reaction include methanol, ethanol, isopropanol, butanol, acetone, and mixtures thereof. Reaction times are typically about 0.5 to about 24 hours. The preferred reaction temperature is about −10° C. to about 60° C., depending on the method chosen. Alternately, 5 can be treated with acid to remove the protected cladinose group from the 3-hydroxy group as described for the conversion of 7 to 8 and treated with base and carbonyldiimidazole then ammonia as described for the conversion of 5 to 6 and the conversion of 6 to 7, respectively, to provide 8. The conversion of 8 to 2 can be accomplished by oxidation of the 3-hydroxy group to a 3-oxo group using a Corey-Kim reaction with N-chlorosuccinimide-dimethyl sulfide or with a modified Swern oxidation procedure using a carbodiimide-DMSO complex. In a preferred method, 8 is added to a preformed N-chlorosuccinimide-dimethyl sulfide complex in a chlorinated solvent such as dichloromethane or chloroform at about −10 to about 25° C. After stirring for about 0.5 to about 4 hours, a tertiary amine such as triethylamine or diisopropylethylamine is added to produce 9, a precursor to compounds of formula I.

Scheme 4

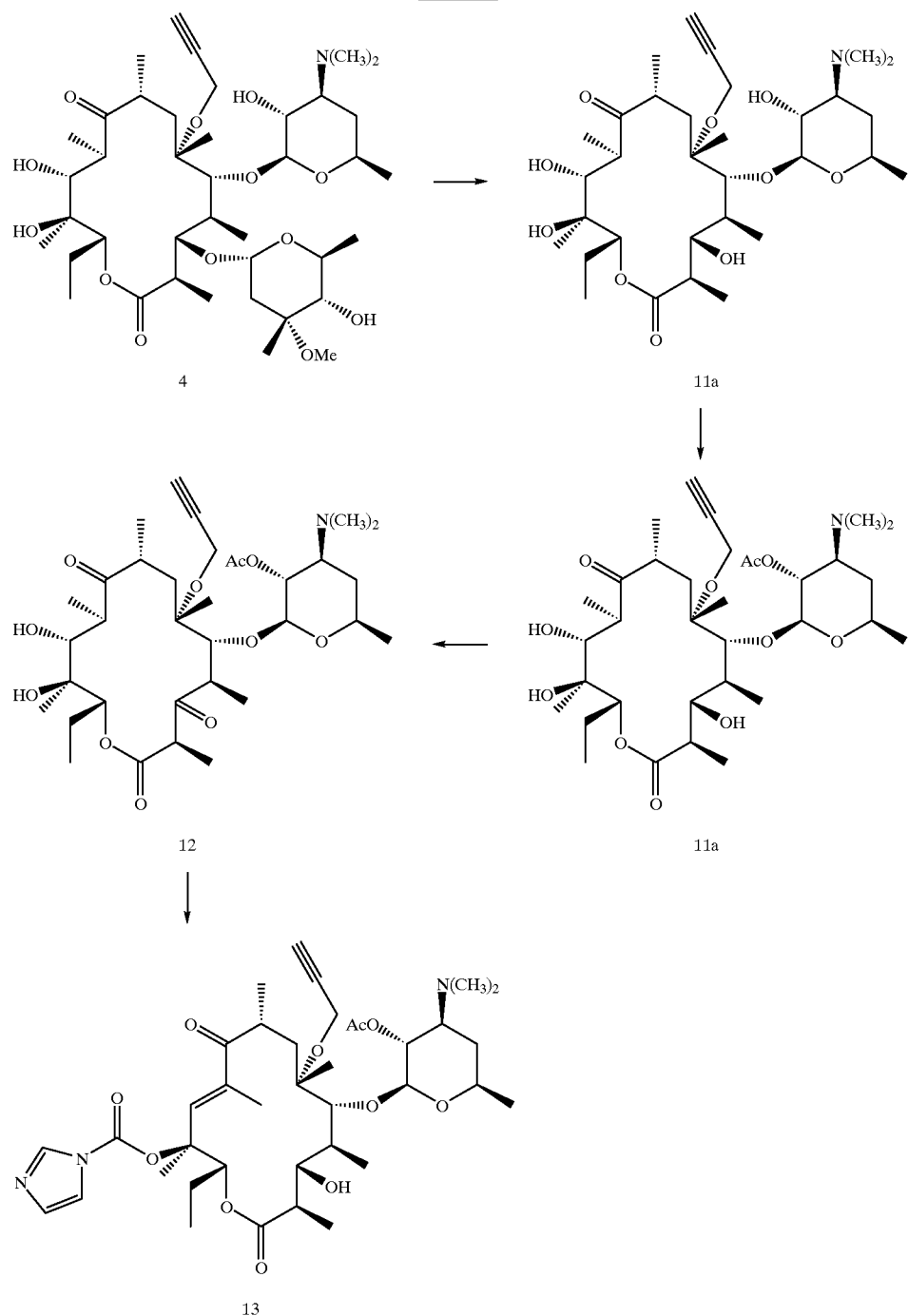

As shown in Scheme 4, 4 (from Scheme 2) can alternatively be (a) treated with acid to remove the cladinose group from the 3-hydroxy group (as described for the conversion of 7 to 8) to provide 11a, (b) protected (as described for the conversion of 4 to 5), to provide 11b, (c) oxidized (as described for the conversion of 8 to 9) to provide 12, and (d) treated with sodium hydride and carbonyldiimidazole (as described for the conversion of 5 to 6) to provide 13.

Scheme 5

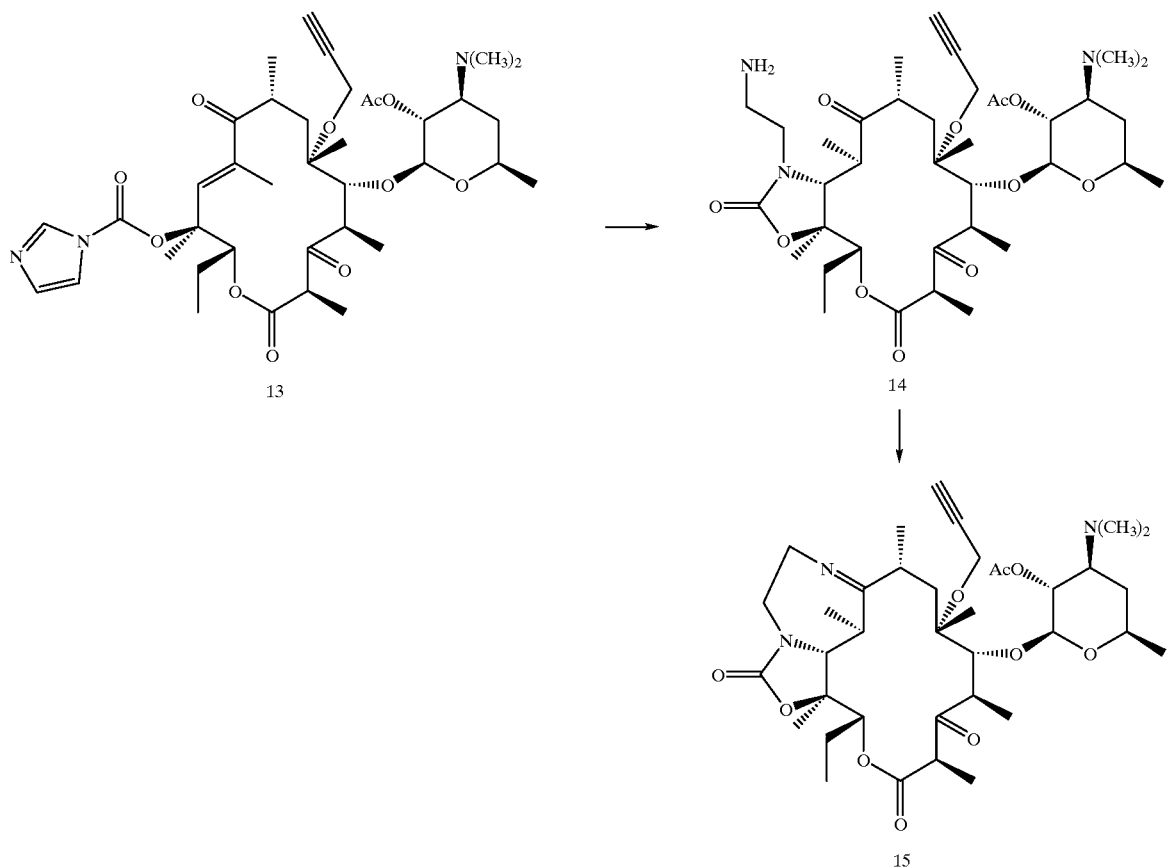

As shown in Scheme 5, 15, a precursor to compounds of formula II was prepared by treatment of 13 with ethylenediamine in a suitable solvent such as aqueous acetonitrile, DMF, or aqueous DMF to provide 14 which further cyclized by intramolecular condensation with the nearby C-9 carbonyl to form 15. Preferred conditions for the formation of 15 from 14 are dilute acetic acid or hydrochloric acid in a suitable organic solvent such as ethanol or iso-propanol.

Scheme 6

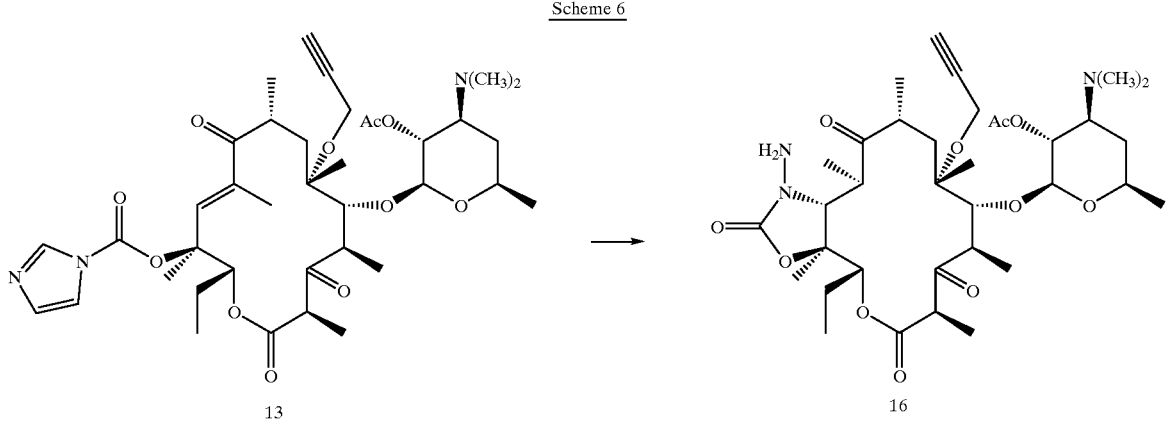

As shown in Scheme 6, 16, a precursor to compounds of formula III was prepared by treatment of Intermediate 13 with hydrazine in a suitable solvent such as acetonitrile, DMSO, DMF, or mixtures thereof at temperatutes from about room temperature to about 100° C. In a preferred embodiment, 13 was treated with hydrazine in DMF at a temperature of about 58° C.

Scheme 7 general route 1:

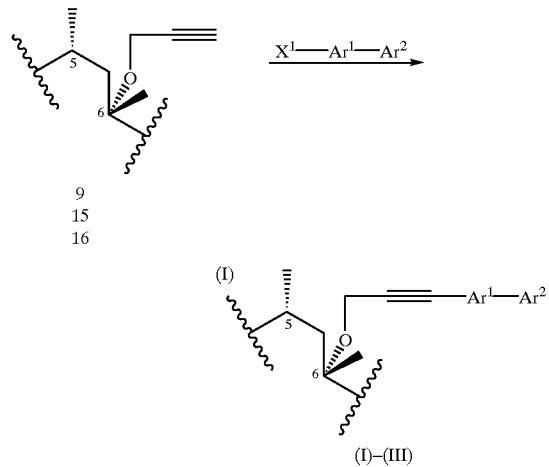

general route 2:

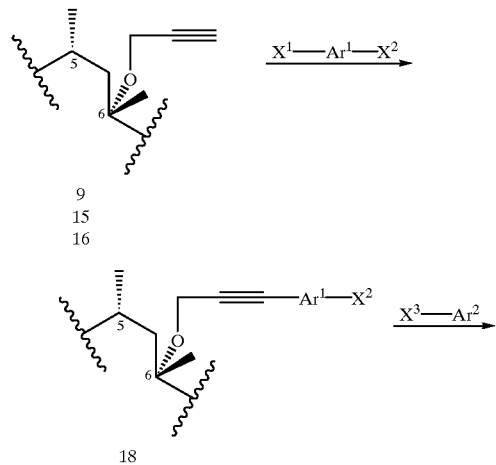

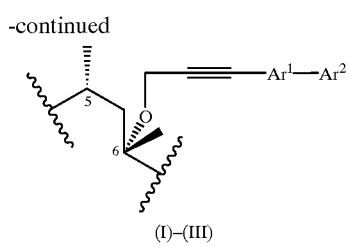

Intermediates 9, 15, and 16 can be converted to compounds of formulae I, II, and III, respectively, by a number of general routes. Two preferred general routes are shown in Scheme 7. In general route 1, the 6-O propargyl group of 9, 15, or 16 is reacted with R precursor groups such as $X^1$—$Ar^1$—$Ar^2$, wherein $Ar^1$ and $Ar^2$ are the same or different and are unsubstituted or substituted aryl groups, or unsubstituted or substituted heteroaryl groups, and $X^1$ is one of any number of covalent bond precursors such as a halide (preferably bromide and iodide) or a sulfonate, to form compounds of formulae I, II, and III. In general route 2, the 6-O propargyl group is reacted with a bifunctionalized aryl or heteroaryl group R precursor, $X^1$—$Ar^1$—$X^2$, to provide prefunctionalized coupling precursor 18, wherein $X^2$ is halide of sulfonate, which is subsequently coupled to R precursor group $X^3$—$Ar^2$, wherein $X^3$ is a covalent bond precursor such as halide (preferably bromide and iodide), sulfonate, trialkylstannane, boronic acid, or borate ester, to provide compounds of formulae I, II, and III. The coupling reactions are performed in the presence of PdII or Pd(0) catalysts with promoters such as phosphines (preferably triphenylphosphine), arsines (preferably triphenylarsine), amines (preferably pyridine and triethylamine), and inorganic bases (preferably potassium carbonate or cesium fluoride) in polar, aprotic solvents such as DMF, DMSO, DME, acetonitrile, THF, or mixtures thereof, at temperatures from about room temperature to about 150° C., depending on the coupling method chosen and the nature of $X^1$, $X^2$, and $X^3$. A thorough survey of coupling procedures, reagents, and solvents for transition metal-catalyzed couplings is provided in Larock, *Comprehensive Organic Transformations. A Guide to Functional Group Preparations*, VCH Publishers, New York (1989).

Scheme 8

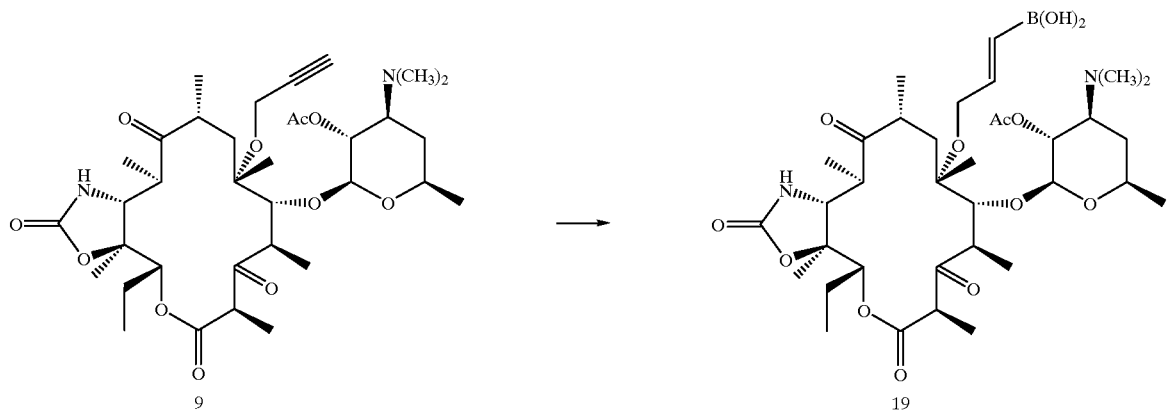

As shown in Scheme 8, the 6-O-propargyl groups of 9 can be derivatized with borane-THF in aprotic solvents at temperatures from about −20° C. to about room temperature to provide vinyl boronic acid derivatives. This chemistry is exemplified by the conversion of 9 to 19. The vinyl boronic acid can then be reacted under Suzuki conditions with the $X^1$—$Ar^1$—$Ar^2$ or $X^1$—$Ar^3$—$X^2$ reagents, catalysts, and promoters described in the description for Scheme 7 to provide additional compounds of the invention. A thorough discussion of Suzuki conditions is provided in *Chemical Reviews*, 1995, Vol. 95, No.7, 2457–2483.

Scheme 9

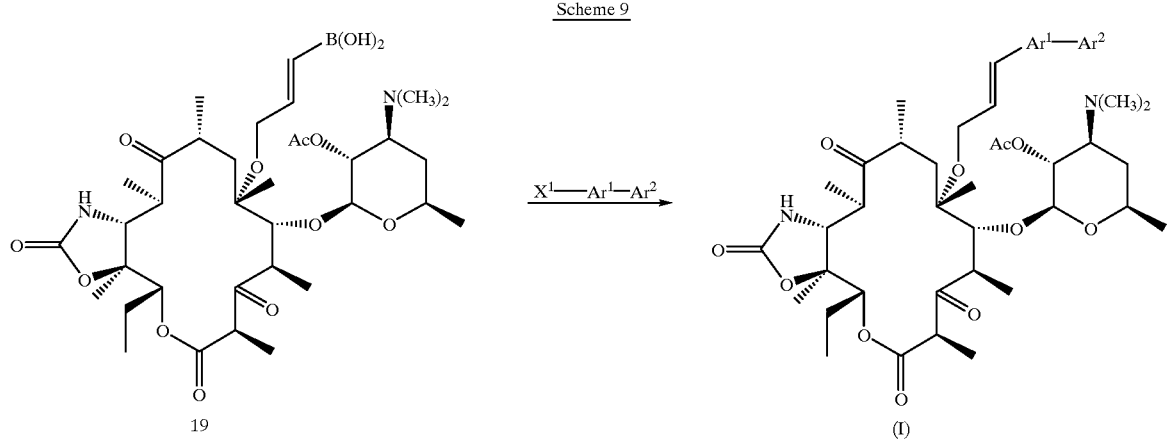

As shown in Scheme 9, the one-step conversion of 19 to compounds of formula I can be accomplished using the chemistry described for general route 1 (Scheme 7).
As shown in Scheme 10, the two-step conversion of 19 to compounds of formula I can be accomplished using the chemistry described for general route 2 (Scheme 7) via intermediate 20.
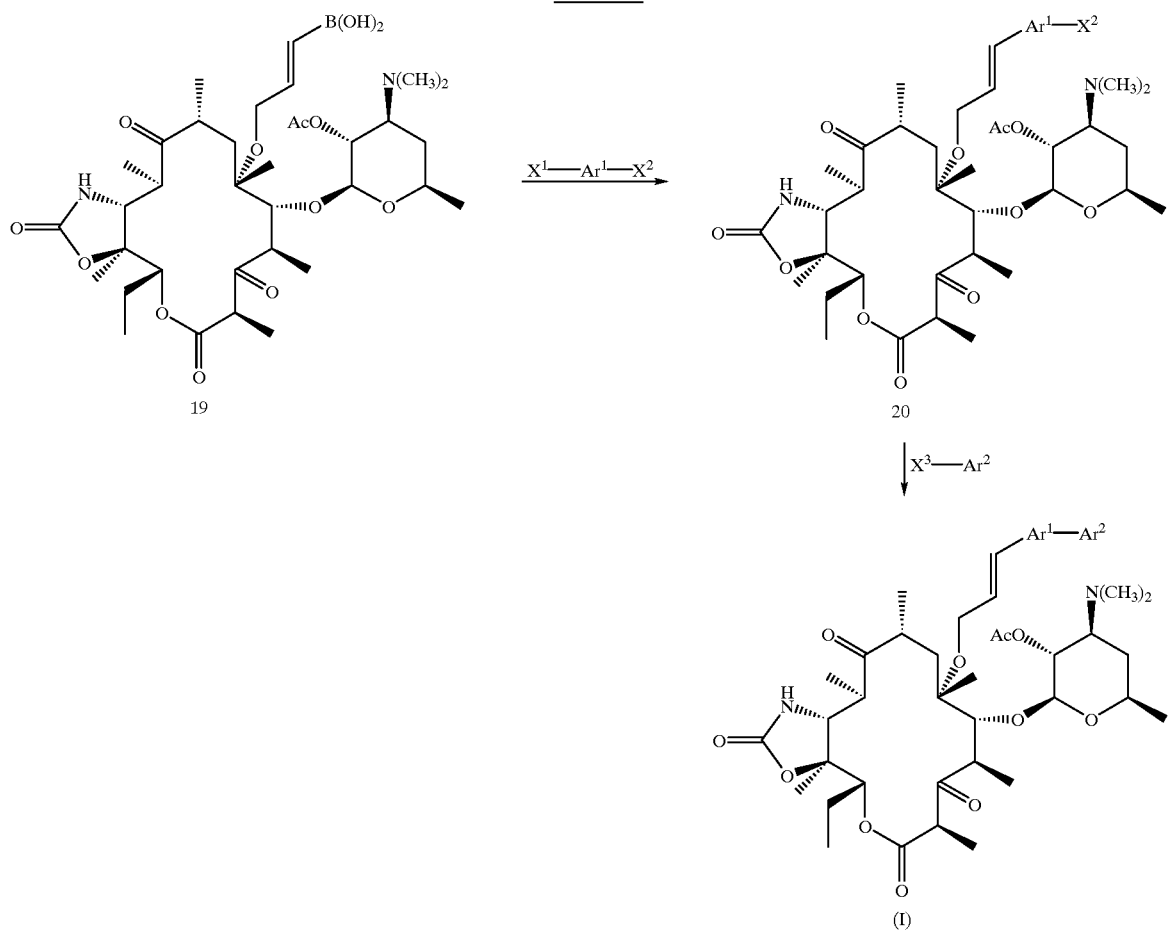
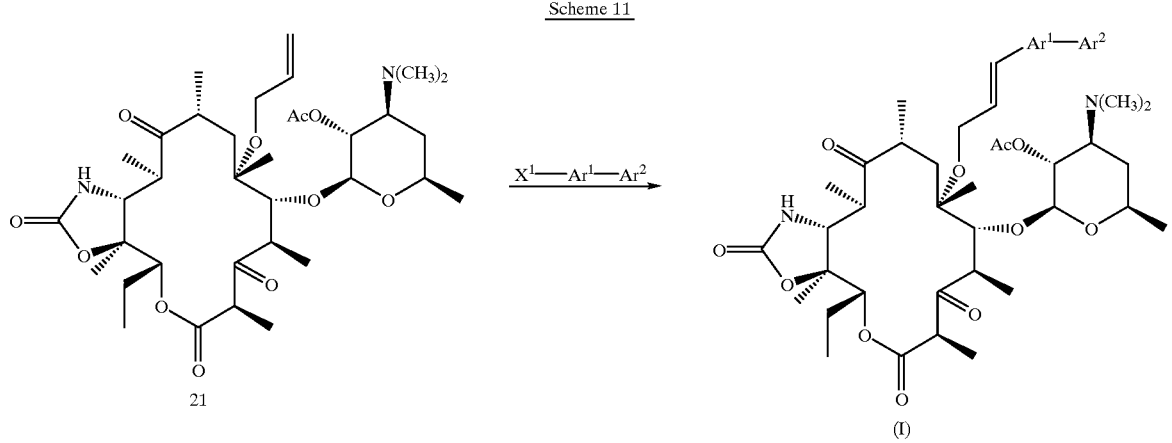

As shown in Scheme 11, general route 1 can also be used with the 6-O-allyl derivative 21 to prepare compounds of formula I. The synthesis of 21 is described in U.S. Pat. No. 5,866,549, Example 1, steps 1a–g and Example 102, steps 120a–c, the disclosure of which is herein incorporated by reference.

dropwise addition over 25 minutes of a solution/slurry of powdered KOH (13.6 g , 0.24 mol) in DMSO (300 mL), stirred vigorously at 0° C. for 1 hour, treated sequentially with powdered KOH (10.9 g, 0.19 mol) and propargyl bromide (80 wt. % in toluene, 0.19 mol), and stirred at 0° C. for 1.5 hours. The addition sequence of KOH (10.9 g) and

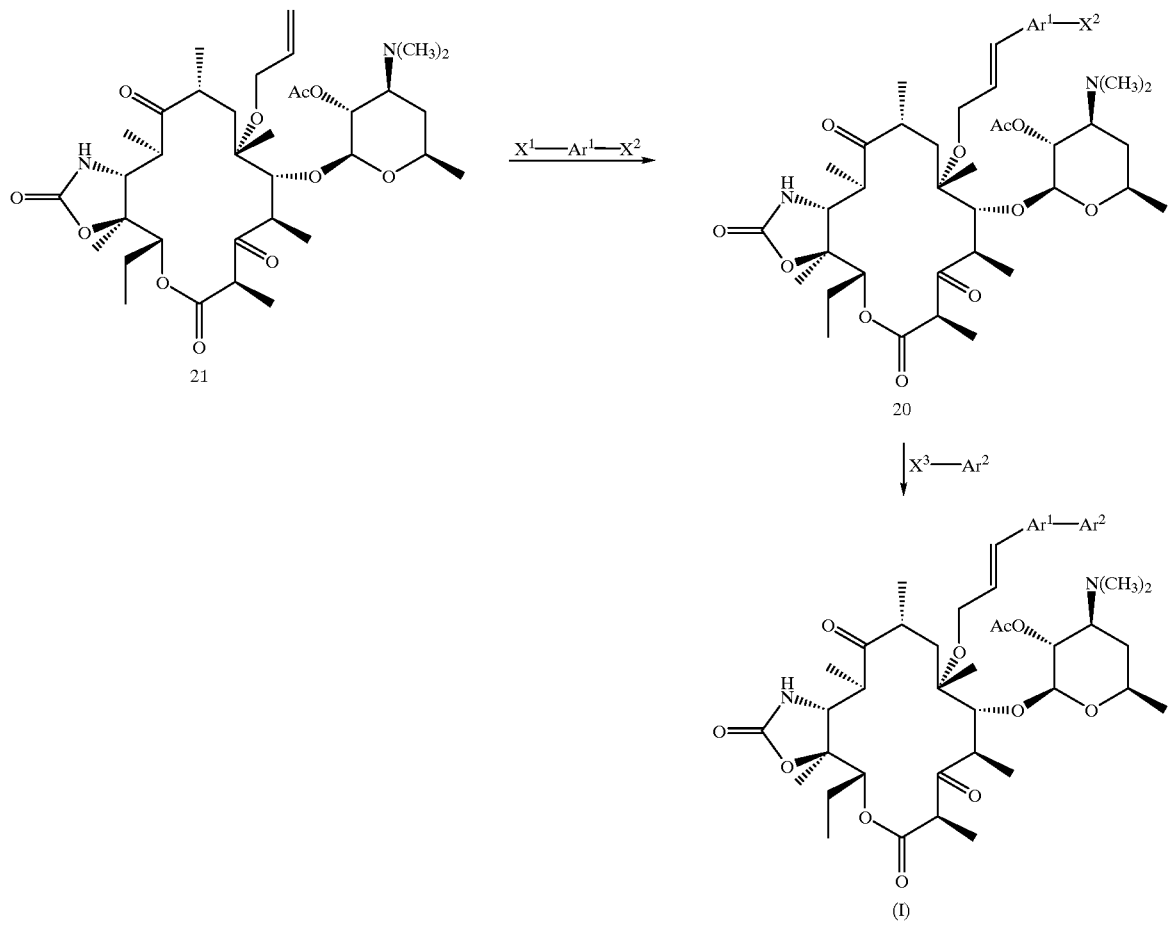

Scheme 12

As shown in Scheme 12, general route 2 can also be used with the 6-O-allyl derivative 21 to prepare compounds of formula I.

EXAMPLES

The compounds and processes of the present invention will be better understood in connection with the following examples, which are intended as an illustration of and not a limitation upon the scope of the invention as defined in the appended claims.

Example 1

Compound of Formula I: $R^b$ is H, L is —C(O)—. T is —NH—, R is —(CH$_2$)—C≡C—(5-(2-pyridyl)-2-thienyl)

Step 1a: Compound 2 from Scheme 1

A stirred solution of compound 1 from Scheme 1 (100 g, 0.0969 mol) in freshly distilled THF (500 mL) and anhydrous DMSO (200 mL) at 0° C., was treated with propargyl bromide (80 wt. % in toluene, 27 mL, 0.24 mol) followed by propargyl bromide solution (21 mL) followed by 1.5 hours of stirring at 0° C. was repeated three times until the reaction was judged to be 60–65% complete by TLC (98:1:1 dichloromethane:methanol:ammonium hydroxide). The cold reaction mixture was diluted with ethyl acetate (1.5 L) and water (1 L), stirred at 0° C. for 5 minutes, and agitated in a separatory funnel. The resulting organic layer was separated, washed sequentially with water (1L) and brine (2×500 mL), dried (MgSO$_4$), filtered, and concentrated to provide 108 g of a dark brown foam which was used in step 1b without further purification.

MS (FAB) m/z 1071 (M+H)$^+$.

Step 1b: Compound 3 from Scheme 1

A suspension of the product from step 1a (108 g) in acetonitrile (300 mL) was treated sequentially with water (150 mL) and glacial acetic acid (200 mL), stirred at room temperature for 20 hours, and concentrated at 40° C. to provide a brown foam. The foam was dissolved in ethyl acetate (750 mL), washed sequentially with 5% aqueous sodium carbonate (2×250 mL) and brine (2×250 mL), dried (MgSO$_4$), filtered, and concentrated to provide 74 g of the crude oxime as a brown foam which was used in step 1c without further purification.

Step 1c: Compound 4 from Scheme 1

A solution of the product from step 1b (74 g) in ethanol (50 mL) was treated sequentially with water (550 mL) and sodium nitrite (33 g, 0.48 mol), stirred at room temperature for 15 minute, treated with 4M HCl (125 mL, 0.48 moles) over 15 minutes, heated to 70° C. for two hours, cooled to room temperature, diluted with ethyl acetate (1.3 L), washed sequentially with 5% aqueous sodium carbonate (2×350 mL) and brine (2×300 mL), dried (MgSO$_4$), filtered, and concentrated. Purification of the residue by flash chromatography on silica gel with 98:1:1 dichloromethane:methanol:ammonium hydroxide provided 45 g of a yellow foam. Crystallization of the foam from hot acetonitrile provided 27 g of desired product as off-white crystals.

MS (APCI) m/z 772 (M+H)$^+$.

Step 1d: Compound 5 from Scheme 2

A solution of the product from step 1c (18.9 g, 24.5 mmol) in anhydrous methylene chloride (100 mL) was treated sequentially with 4-(dimethylamino)pyridine (105 mg, 0.86 mmol) and triethylamine (7.16 ml, 51 mmol), cooled to 15–20° C. in a cold water bath, treated with acetic anhydride (5.5 mL, 58 mmol) over 5 minutes, stirred at room temperature for 4.5 hours, diluted with ethyl acetate (300 mL), washed sequentially with 5% aqueous sodium carbonate (2×100 mL), water (2×100 mL) and brine (2×100 mL), dried (MgSO$_4$), filtered, and concentrated to provide 21 g of the desired product as a white foam which was used without further purification in step 1e.

Step 1e: Compound 6 from Scheme 2

A solution of the product from step 1d (92.38 g, 0.108 mol) in THF (350 mL) and DMF (175 mL) at room temperature was treated with 1,1'-carbonyldiimidazole (61.26 g, 0.378 mol), cooled to 0° C., treated with sodium hydride (60% dispersion in mineral oil, 5.4 g, 0.135 mol) over 1 hour, stirred an additional 30 minutes at 0° C. and at room temperature for 3 hours, recooled to 0° C., diluted with ethyl acetate (800 mL), washed sequentially with 5% aqueous sodium bicarbonate (200 mL), water (2×500 mL) and brine (2×300 mL), dried (Na$_2$SO$_4$), filtered, and concentrated to provide 104 g of the desired product as a dark yellow foam which was used without further purification in step if.

MS (ESI) m/z 932 (M+H)$^+$.

Step 1f: Compound 7 from Scheme 2

A solution of the product from step 1e (52 g, 55.8 mmol) in acetonitrile (500 mL) at −78° C. was treated with liquid ammonia (500–600 mL) in a sealed reaction vessel, stirred at room temperature for 24 hours, concentrated first by evaporation of the ammonia at room temperature and atmospheric pressure, and concentrated finally to remove the acetonitrile. The crude product (52 g) was purified by flash chromatography on silica gel with a gradient of from 3:7 acetone/hexanes to 1:1 acetone/hexanes to provide 32 g of the title compound as a yellow foam.

Step 1g: Compound 8 from Scheme 3

A suspension of the product from step 1f (63.92 g, 72.55 mmol) in 1:1 ethanol/water (600 AL) at 0° C. was treated with 4N HCl (393 mL, 1860 mmol) over 20 minutes, stirred at room temperature for 24 hours, recooled to 0° C., diluted with water (200 mL), adjusted to pH 9–10 with 4N sodium hydroxide solution, diluted with ethyl acetate, washed with brine, dried (Na$_2$SO$_4$), filtered, and concentrated to provide 62.1 g of yellow foam. Crystallization of the foam from 1.5:1 ethyl acetate/hexanes (115 mL) provided 34 g of the desired product as a white solid.

MS (ESI) m/z 681 (M+H)$^+$.

Step 1h: Compound 9 from Scheme 3

A solution of N-chlorosuccinimide (10.86g, 81.66 mmol) in anhydrous dichloromethane (450 mL) at −10° C. was treated with methyl sulfide (6.98 ml, 95.27 mmol) over 10 minutes, stirred for an additional 10 minutes, treated with a solution of the product from step ig (37.02 g, 54.44 mmol) in anhydrous dichloromethane (450 mL) over 35 minutes, stirred an additional 25 minutes at −10° C., treated with triethylamine (7.57 mL, 54.44 mmol) over 10 minutes, stirred at −10° C. for an additional 50 minutes, washed sequentially with saturated. sodium bicarbonate solution. and brine, dried (Na$_2$SO$_4$), filtered, and concentrated. Purification of the residue by flash chromatography on silica gel with from 3:7 to 1:1 acetone/hexanes provided 31.9 g of the desired product as a pale yellow foam.

MS (ESI) m/z 679 (M+H)$^+$.

Step 1i: Option 1: Compound of Formula I: $R^b$ is CH$_3$C(O)—, L is —C(O)—, T is —NH—, R is —(CH$_2$)—C≡C—(5-iodo-2-thienyl)

A slurry of the product from step 1h (5.02 g, 7.40 mmol), 2,5-diiodothiophene (5.47 g, 16.29 mmol), dichlorobis(triphenylphosphine)palladium(II) (0.103 g, 0.148 mmol), and copper I iodide (0.014 g, 0.074 mmol) in triethylamine (18 mL) and acetonitrile (6 mL) was heated at 60° C. for 3 hours, stirred at room temperature for 48 hours, and concentrated. Purification of the residue by flash chromatography on silica gel with from 40:60 to 1:1 acetone-hexanes provided 4.54 g (69.4%) of the desired product as a yellow foam.

MS (APCI) m/z 887 (M+H)$^+$.

Step 1i: Option 2: Compound of Formula I: $R^b$ is CH$_3$C(O)—. L is —C(O)—. T is —NH—, R is —(CH)—C≡C—(5-bromo-2-thienyl)

The product from Example 1h (10.8 g) was processed as described in step 1i, option 1, (substituting 2,5-dibromothiophene for 2,5-diiodothiophene) to provide 8.81 g of the desired product.

MS (APCI) m/z 841 (M+H)$^+$.

Step 1j: Compound of Formula I: $R^b$ is CH$_3$C(O)—. L is —C(O)—, T is —NH—, R is —(CH$_2$)—C≡C—(5-(2-pyridyl)-2-thienyl)

A solution of the product from step 1i, option 2 (300 mg, 0.34 mmol), 2-tri-n-butylstannylpyridine (312 mg, 0.85 mmol), tetrakis(triphenylphosphine)palladium(0) (38 mg, 0.034 mmol) and copperI bromide (2.4 mg, 0.017 mmol) in degassed 1,4-dioxane (2.5 mL) was heated at 90 ° C. for 21 hours and concentrated. Purification of the residue by flash chromatography on silica gel with from 35:65 to 1:1 acetone-hexanes provided 170 mg of a yellow foam.

Step 1k: Compound of Formula I: $R^b$ is H, L is —C(O)—, T is —NH—, R is —(CH$_2$)—C≡C—(5-(2-pyridyl)-2-thienyl)

A solution of the product from step 1j was dissolved in methanol (10 mL), stirred for 6 hours at room temperature, and concentrated. Purification of the residue by flash chromatography on silica gel with 98:1:1 dichloromethane:methanol:ammonium hydroxide provided 136 mg of the desired product as a yellow foam.

MS (APCI) m/z 796 (M+H)$^+$; $^{13}$C NMR (100 MHz, CDCl$_3$) 216.6, 205.1, 169.3, 157.7, 152.1,149.5, 145.8, 136.5, 133.4, 124.5, 124.3, 122.0, 118.9, 103.1, 90.6, 83.5, 79.4, 79.4, 77.3, 77.3, 70.2, 69.5, 65.8, 58.2, 51.7, 51.0, 46.6, 44.7, 40.2, 38.7, 37.3, 28.3, 22.5, 21.1, 19.7, 18.0, 14.7, 14.5, 13.6, 13.6, 10.5; High Resolution MS (FAB) calcd (M+H)$^+$ for C$_{42}$H$_{58}$N$_3$O$_{10}$S: 796.3843. Found: 796.3826.

Example 2

Compound of Formula I: $R^b$ is H, L is —C(O)—, T is —NH—, R is —(CH$_2$)—C≡C—(5-(3-pyridyl)-2-thienyl)

The product from step 1i, option 2 (250 mg), was processed as described in steps 1j and 1k (substituting 3-tri-n- butylstannylpyridine for 2-tri-n-butylstannylpyridine) to provide 61 mg of the desired product.

High Resolution MS (FAB) calcd (M+H)$^+$ for $C_{42}H_{58}N_3O_{10}S$: 796.3843. Found: 796.3826.

Example 3

Compound of Formula I: $R^b$ is H, L is —C(O)—, T is —NH—, R is —(CH$_2$)—C≡C—(5-(4-pyridyl)-2-thienyl)

The product from step 1i, option 2 (350 mg), was processed as described in steps 1j and 1k (substituting 4-tri-n-butylstannylpyridine for 2-tri-n-butylstannylpyridine) to provide 105 mg of the desired product.

High Resolution MS (ESI) calcd (M+H)$^+$ for $C_{42}H_{58}N_3O_{10}S$: 796.3843. Found: 796.3833.

Example 4

Compound of Formula I: $R^b$ is H, L is —C(O)—, T is —NH—, R is —(CH$_2$)—C≡C—(5-(5-pyrimidinyl)-2-thienyl)

step 4a: Compound of Formula I: $R^b$ is —C(O)CH$_3$, L is —C(O)—, T is —NH—, R is —(CH$_2$)—C≡C—(5-(5-pyrimidinyl)-2-thienyl)

A solution of the product from step 1i, option 1 (250 mg), hexamethylditin (100 mg), dichlorobis(triphenylphosphine)palladium(II) (16 mg) and 5-bromopyrimidine (49 mg), in toluene (4 mL) in a pressure vial was heated to 100° C. for 18 hours, cooled, and concentrated. The residue was purified on silica gel with 98:1:1 dichloromethane:methanol:ammonium hydroxide to provide 80 mg of the desired product.

step 4b: Compound of Formula I: $R^b$ is H, L is —C(O)—, T is —NH—, R is —(CH$_2$)—C≡C—(5-(5-pyrimidinyl)-2-thienyl)

A solution of the product from step 4a (126 mg) was stirred in methanol (5 mL) for 20 hours and concentrated to provide 118 mg the desired product.

High Resolution MS (FAB) calcd (M+H)$^+$ for $C_{41}H_{57}N_4O_{10}S$: 797.3790. Found 797.3793.

Example 5

Compound of Formula I: $R^b$ is H, L is —C(O)—, T is —NH—, R is —(CH$_2$)—C≡C—(5-(2-pyrimidinyl)-2-thienyl)

The product from step 1i, option 2 (250 mg), was processed as described in steps 1j and 1k (substituting 2-tri-n-butylstannylpyridine for 2-tri-n-butylstannylpyridine) to provide 41 mg of the desired product.

High Resolution MS (FAB) calcd (M+H)$^+$ for $C_{41}H_{57}N_4O_{10}S$: 797.3790. Found 797.3795.

Example 6

Compound of Formula I: $R^b$ is H, L is —C(O)—, T is —NH—, R is —(CH$_2$)—C≡C—(5-(2-pyrazinyl)-2-thienyl)

The product from step 1i, option 2 (252 mg), was processed as described in steps 1j and 1k (substituting 2-tri-n-butylstannylpyridine for 2-tri-n-butylstannylpyridine) to provide 93 mg of the desired product.

High Resolution MS (FAB) calcd (M+H)$^+$ for $C_4,H_{57}N_4O_{10}S$: 797.3790. Found 797.3784.

Example 7

Compound of Formula I: $R^b$ is H, L is —C(O)—, T is —NH—, R is —(CH$_2$)—C≡C—(5-(5-pyrimidinyl)-2-thienyl)

step 7a: Compound of Formula I: $R^b$ is CH$_3$C(O)—, L is —C(O)—, T is —NH—, R is —(CH$_2$)—C≡C—(5-(5-pyrimidinyl)-2-thienyl)

A solution of Pd$_2$(dba)$_3$ (96 mg, 0.105 mmol) and triphenylarsine (128 mg, 0.42 mmol) in degassed acetonitrile (6 mL) was stirred for 30 minutes, treated sequentially with the product from step 1h (1.04 g, 1.4 mol), 2-bromo-5-(4-pyrimidinyl)thiophene (0.607 g, 2.5 mmol) and copperI iodide (2.7 mg, 0.014 mmol), stirred at 80° C. for 2 hours, cooled, treated with ethyl acetate (50 mL) and water (10 mL), filtered through powdered seashells (Celite®). The water was removed, and the organic layer was washed with brine, dried (Na$_2$SO$_4$), filtered, and concentrated. The residue was chromatographed on silica gel with 98:1:1 dichloromethane:methanol:ammonium hydroxide to provide 724 mg of the desired product.

step 7b: Compound of Formula I: $R^b$ is H, L is —C(O)—, T is —NH—, R is —(CH$_2$)—C≡C—(5-(5-pyrimidinyl)-2-thienyl)

A solution of the product from step 7a (724 mg) was stirred in methanol (15 mL) for 48 hours and concentrated. Purification of the residue on silica gel with 98:1:1 dichloromethane:methanol:ammonium hydroxide provided 413 mg of the desired product.

High Resolution MS (FAB) calcd (M+H)$^+$ for $C_{41}H_{57}N_4O_{10}S$: 797.3790. Found 797.3787.

Example 8

Compound of Formula I: $R^b$ is H, L is —C(O)—, T is —NH—, R is —(CH$_2$)—C≡C—(5-(5-cyano-3-pyridyl)-2-thienyl)

The product from step 1i, option 2 (250 mg), was processed as described in steps 4a and 4b (substituting 5-bromonicotinonitrile for 5-bromopyrimidine) to provide 115 mg the desired product.

High Resolution MS (FAB) calcd (M+H)$^+$ for $C_{43}H_{57}N_4O_{10}S$: 821.3795. Found 821.3766.

Example 9

Compound of Formula I: $R^b$ is H, L is —C(O)—, T is —NH—, R is —(CH$_2$)—C≡C—(5-(5-carboxamido-3-pyridyl)-2-thienyl)

The product from step 1i, option 2 (250 mg), was processed as described in steps 4a and 4b (substituting 5-bromonicotinamide for 5-bromopyrimidine) to provide 115 mg the desired product.

High Resolution MS (FAB) calcd (M+H)$^+$ for $C_{43}H_{59}N_4O_{11}S$: 839.3896. Found 839.3895.

Example 10

Compound of Formula I: $R^b$ is H, L is —C(O)—, T is —NH—, R is —(CH$_2$)—C≡C—(5-(5-ethoxycarbonyl-3-pyridyl)-2-thienyl)

The product from step 1i, option 2 (250 mg), was processed as described in steps 4a and 4b (substituting ethyl 5-bromonicotinate for 5-bromopyrimidine) to provide 44 mg the desired product.

High Resolution MS (FAB) calcd (M+H)$^+$ for $C_{45}H_{62}N_3O_{12}S$: 868.4049. Found 868.4037.

Example 11

Compound of Formula I: $R^b$ is H, L is —C(O)—, T is —NH—, R is —(CH$_2$)—C≡C—(5-(5-N,N-dimethylcarboxamido-3-pyridyl)-2-thienyl)

The product from step 1i, option 1 (250 mg), was processed as described in steps 4a and 4b (substituting 5-bromo-N,N-dimethylnicotinamide for 5-bromopyrimidine) to provide 130 mg the desired product.

MS (ESI) m/z 867 (M+H)$^+$.

Example 12

Compound of Formula I: $R^b$ is H, L is —C(O)—, T is —NH—, R is —(CH$_2$)—C≡C—(5-(5-N', N'-dimethylhydrazidocarbonyl-3-pyridyl)-2-thienyl)

The product from step 1i, option 1 (250 mg), was processed as described in steps 4a and 4b (substituting 5-bromo-N',N'-dimethylnicotinohydrazide for 5-bromopyrimidine) to provide 56 mg the desired product.

MS (ESI) m/z 882 (M+H)$^+$.

Example 13

Compound of Formula I: $R^b$ is L is —C(O)—, T is —NH—, H, R is —(CH)—C≡C—(5-(phenyl)-2-thienyl)

step 13a:

A solution of the product from step 1i, option 1 (195 mg, 0.22 mmol), phenylboronic acid (40.2 mg, 0.33 mmol), potassium carbonate (76 mg, 0.55 mmol), and Pd(OAc)$_2$ (0.25 mg, 0.001 mmol) in acetone (2 mL) and water (1 mL) was heated to 60° C. for 18 hours, cooled to room temperature, treated with ethyl acetate, washed sequentially with 5% sodium bicarbonate and brine, dried (Na$_2$SO$_4$), filtered and concentrated. The residue was chromatographed on silica gel with 98:1:1 dichloromethane:methanol:ammonium hydroxide to provide 95 mg (32%) of the desired product.

High Resolution MS (FAB) calcd (M+H)$^+$ for C$_{43}$H$_{59}$N$_2$O$_{12}$S: 795.3885. Found 795.3870.

Example 14

Compound of Formula I: $R^b$ is H, L is —C(O)—, T is —NH—, R is —(CH$_2$)—C≡C—(5-(3-methoxyphenyl)-2-thienyl)

The product from step 1i, option 1 (151 mg), was processed as described in Example 13 (substituting 3-methoxyphenylboronic acid for phenylboronic acid) to provide 95 mg the desired product.

High Resolution MS (FAB) calcd (M+H)$^+$ for C$_{44}$H$_{61}$N$_2$O$_{11}$S: 825.3996. Found 825.4023.

Example 15

Compound of Formula I: $R^b$ is H, L is —C(O)—, T is —NH—, R is —(CH$_2$)—C≡C—(5-(3-fluorophenyl)-2-thienyl)

The product from step 1i, option 1 (195 mg), was processed as described in Example 13 (substituting 3-fluorophenylboronic acid for phenylboronic acid) to provide 83 mg the desired product.

High Resolution MS (FAB) calcd (M+H)$^+$ for C$_{43}$H$_{58}$N$_2$O$_{10}$SF: 813.3791. Found 813.3803.

Example 16

Compound of Formula I: $R^b$ is H, L is —C(O)—, T is —NH—, R is —(CH$_2$)—C≡C—(5-(3-chlorophenyl)-2-thienyl)

The product from step 1i, option 1 (252 mg), was processed as described in Example 13 (substituting 3-chlorophenylboronic acid for phenylboronic acid) to provide 43 mg the desired product.

High Resolution MS (FAB) calcd (M+H)$^+$ for C$_{43}$H$_{58}$N$_2$O$_{10}$SCl: 829.3495. Found 829.3496.

Example 17

Compound of Formula I: $R^b$ is H, L is —C(O)—, T is —NH—, R is —(CH$_2$)—C≡C—(5-(3,5-dichlorophenyl)-2-thienyl)

The product from step 1i, option 1 (266 mg), was processed as described in Example 13 (substituting 3,5-dichlorophenylboronic acid for phenylboronic acid) to provide 82 mg the desired product.

High Resolution MS (FAB) calcd (M+H)$^+$ for C$_{43}$H$_{57}$N$_2$O$_{10}$SCl$_2$: 863.3105. Found 863.3108.

Example 18

Compound of Formula I: $R^b$ is H, L is —C(O)—, T is —NH—, R is —(CH$_2$)—C≡C—(5-(3-methylphenyl)-2-thienyl)

The product from step 1i, option 1 (159 mg), was processed as described in Example 13 (substituting 3-methylphenylboronic acid for phenylboronic acid) to provide 93 mg the desired product.

High Resolution MS (FAB) calcd (M+H)$^+$ for C$_{44}$H$_{61}$N$_2$O$_{10}$S: 809.4041. Found 809.4037.

Example 19

Compound of Formula I: $R^b$ is H, L is —C(O)—, T is —NH—, R is —(CH$_2$)—C≡C—(5-(3-trifluoromethylphenyl)-2-thienyl)

The product from step 1i, option 1 (195 mg), was processed as described in Example 13 (substituting 3-trifluoromethylphenylboronic acid for phenylboronic acid) to provide 120 mg the desired product.

High Resolution MS (FAB) calcd (M+H) +for C$_{44}$H$_{58}$N$_2$O$_{10}$SF$_3$: 863.3759. Found 863.3750.

Example 20

Compound of Formula I: $R^b$ is H, L is —C(O)—, T is —NH—, R is —(CH$_2$)—C≡C—(5-(3-acetamidophenyl)-2-thienyl)

The product from step 1i, option 1 (151 mg), was processed as described in Example 13 (substituting 3-acetamidophenylboronic acid for phenylboronic acid) to provide 80 mg the desired product.

High Resolution MS (FAB) calcd (M+H)$^+$ for C$_{45}$H$_{62}$N$_3$O$_{11}$S: 852.4100. Found 852.4096.

Example 21

Compound of Formula I: $R_b$ is H, L is —C(O)—, T is —NH—, R is —(CH$_2$)—C≡C—(5-(3-nitrophenyl)-2-thienyl)

The product from step 1i, option 1 (151 mg), was processed as described in Example 13 (substituting 3-nitrophenylboronic acid for phenylboronic acid) to provide 102 mg the desired product.

High Resolution MS (FAB) calcd (M+H)$^+$ for C$_{43}$H$_{58}$N$_3$O$_{12}$S: 840.3736. Found 840.3722.

Example 22

Compound of Formula I: $R^b$ is H, L is —C(O)—, T is —NH—, R is —(CH$_2$)—C≡C—(5-(4-fluorophenyl)-2-thienyl)

The product from step 1i, option 1 (293.6 mg), was processed as described in Example 13 (substituting 4-fluorophenylboronic acid for phenylboronic acid) to provide 145 mg the desired product.

High Resolution MS (FAB) calcd (M+H)$^+$ for C$_{43}$H$_{58}$N$_2$O$_{10}$SF: 813.3796. Found 813.3803.

Example 23

Compound of Formula I: $R^b$ is H, L is —C(O)—, T is —NH—, R is —(CH$_2$)—C≡C—(5-(2-furanyl)-2-thienyl)

The product from step 1i, option 1 (266 mg, 0.30 mmol), was processed as described in steps 1j and 1k (substituting 2-tri-n-butylstannylfuran for 2-tri-n-butylstannylpyridine) to provide 74 mg of the desired product.

High Resolution MS (FAB) calcd (M+H)$^+$ for C$_{41}$H$_{57}$N$_2$O$_{11}$S: 785.3683. Found 785.3679.

Example 24

Compound of Formula I: $R^b$ is H, L is —C(O)—, T is —NH—, R is —(CH$_2$)—C≡C—(4-(5-formyl-2-furanyl)phenyl)

step 24a: Compound of Formula I: $R^b$ is CH$_3$C (O)—, L is —C(O)—, T is —NH—, R is —(CH$_2$)—C≡C—(4-(5-formyl-2-furanyl)phenyl)

A solution of the product from step 1h (300 mg), dichlorobis(triphenylphosphine)palladium(II) (6.2 mg), copper(I) iodide (0.84 mg), and 5-(4-bromophenyl)-2-furaldehyde (200 mg) in acetonitrile (0.5 mL) and triethylamine (2 mL) was heated to 60 C for 18 hours, cooled to room temperature, treated with ethyl acetate, washed sequentially with 5! sodium bicarbonate and brine, dried (Na$_2$SO$_4$), filtered and concentrated. The residue was chromatographed on silica gel with 98.5:1:0.5 chloroform:methanol:ammonium hydroxide to provide 105 mg of the desired product.

step 24b: Compound of Formula I: $R^b$ is H, L is —C(O)—, T is —NH—, R is —(CH$_2$)—C≡C—(4-(5-formyl-2-furanyl)phenyl)

A solution of the product from step 24a (165 mg) was processed as described in step 7b, filtered through a syringe membrane filter, and concentrated to provide 55 mg of the desired product.

High Resolution MS (FAB) calcd (M+H)$^+$ for C$_{44}$H$_{59}$N$_2$O$_{12}$: 807.4075. Found 807.4075.

Example 25

Compound of Formula I: $R^b$ is H, L is —C(O)—, T is —NH—, R is —(CH)—C≡C—(2,2'-bisthienyl)

The product from step 1i, option 1 (110 mg), was processed as described in steps 1j and 1k (substituting 2-n-tributylstannylthiophene for 2-tri-n-butylstannylpyridine) to provide 43 mg of the desired product.

High Resolution MS (FAB) calcd (M+H)$^+$ for C$_{41}$H$_{57}$N$_2$O$_{10}$ S$_2$: 801.3455. Found 801.3462.

Example 26

Compound of Formula I: $R^b$ is H, L is —C(O)—, T is —NH—, R is —(CH$_2$)—C≡C—(2-(5-chloro-2-thienyl)thienyl)

The product from step 1i, option 2 (250 mg), was processed as described in steps 4a and 4b (substituting 2-bromo-5-chlorothiophene for 5-bromopyrimidine) to provide 80 mg of the desired product.

High Resolution MS (FAB) calcd (M+H)$^+$ for C$_{41}$H$_{56}$N$_2$O$_{10}$S$_2$Cl: 835.3059. Found 835.3059.

Example 27

Compound of Formula I: $R^b$ is H, L is —C(O)—, T is —NH—, R is —(CH$_2$)—C≡C—(2,3'-bis(thienyl))

The product from step 1i, option 1 (151 mg), was processed as described in Example 13 (substituting 3-thiopheneboronic acid for phenylboronic acid) to provide 78 mg of the desired product.

High Resolution MS (FAB) calcd (M+H)$^+$ for C$_{41}$H$_{57}$N$_2$O$_{10}$S$_2$: 801.3455. Found 801.3462.

Example 28

Compound of Formula I: $R^b$ is H, L is —C(O)—, T is —NH—, R is —(CH$_2$)—C≡C—(5-(2-thiazolyl)-2-thienyl)

The product from step 1i, option 1 (250 mg), was processed as described in steps 1j and 1k (substituting 2-tri-n-butylstannylthiazole for 2-tri-n-butylstannylpyridine) to provide 110 mg of the desired product.

High Resolution MS (FAB) calcd (M+H)$^+$ for C$_{40}$H$_{56}$N$_3$O$_{10}$S$_2$: 802.3402. Found 802.3412.

Example 29

Compound of Formula I: $R^b$ is H, L is —C(O)—, T is —NH—, R is —(CH$_2$)—C≡C—(5-(5-thiazolyl)-2-thienyl)

The product from step 1i, option 1 (839 mg), was processed as described in steps 1j and 1k (substituting 5-tri-n-butylstannylthiazole for 2-tri-n-butylstannylpyridine) to provide 281 mg of the desired product.

High Resolution MS (FAB) calcd (M+H)$^+$ for C$_{40}$H$_{56}$N$_3$O$_{10}$S$_2$: 802.3402. Found 802.3400.

Example 30

Compound of Formula I: $R^b$ is H, L is —C(O)—, T is —NH—, R is —(CH)—C≡C—(5-(4-thiazolyl)-2-thienyl)

The product from step 1i, option 1 (1.08 g), was processed as described in steps 1j and 1k (substituting 4-tri-n-butylstannylthiazole for 2-tri-n-butylstannylpyridine) to provide 439 mg of the desired product.

High Resolution MS (FAB) calcd (M+H)$^+$ for C$_{40}$H$_{56}$N$_3$O$_{10}$S$_2$: 802.3402. Found 802.3402.

Example 31

Compound of Formula I: $R^b$ is H, L is —C(O)—, T is —NH—, R is —(CH$_2$)—C≡C—(5-(2-methyl-5-thiazoyl)-2-thienyl)

The product from step 1i, option 1 (100 mg), was processed as described in steps 24a and 24b (substituting 4-(5-bromo-2-thienyl)-2-methylthiazole for 5-(4-bromophenyl)-2-furaldehyde) to provide 65trensferA mg of the desired product.

High Resolution MS (FAB) calcd (M+H)$^+$ for C$_{41}$H$_{58}$N$_3$O$_{10}$S$_2$: 816.3582. Found 816.3564.

Example 32

Compound of Formula I: $R^b$ is H, L is —C(O)—, T is —NH—, R is —(CH$_2$)—C≡C—(5-(1-methyl-2-imidazolyl)-2-thienyl)

The product from step 1i, option 2 (302 mg), was processed as described in steps 1j and 1k (substituting 1-methyl-2-tri-n-butylstannylimidazole for 2-tri-n-butylstannylpyridine and toluene for 1,4-dioxane) to provide 118 mg of the desired product.

High Resolution MS (FAB) calcd (M+H)$^+$ for C$_{41}$H$_{59}$N$_4$O$_{10}$S: 799.3946. Found 799.3943.

Example 33

Compound of Formula I: $R^b$ is H, L is —C(O)—, T is —NH—, R is —(CH$_2$)—C≡C—(5-(2-quinoxalinyl)-2-thienyl)

The product from step 1h (150 mg) and was processed as described in steps 24a and 24b (substituting 2-(5-bromo-2-thienyl)quinoxaline for 5-(4-bromophenyl)-2-furaldehyde) to provide 61 mg of the desired product.

High Resolution MS (FAB) calcd (M+H)$^+$ for C$_{45}$H$_{59}$N$_4$O$_{10}$S: 847.3952. Found 847.3958.

Example 34

Compound of Formula I: $R^b$ is H, L is —C(O)—, T is —NH—, R is —(CH$_2$)—C≡C—(5-(2-benzothiophenyl)-2-thienyl)

The product from step 1i, option 1 (301 mg), was processed as described in Example 13 (substituting 2-benzothiopheneboronic acid acid for phenylboronic acid) to provide 155 mg of the desired product.

Example 35

Compound of Formula II: $R^b$ is H, R is —(CH$_2$)—C≡C—(5-(2-pyridyl)-2-thienyl)

step 35a: Compound 11a from Scheme 4

A suspension of compound 4 from Scheme 4 (56 g) in ethanol (180 mL) and water (540 mL) was slowly treated with 1M HCl (130 mL) over 20 minutes, stirred for 7 hours, cooled to 0° C., treated with 1M NaOH (130 mL), and extracted with ethyl acetate. The extract was washed with brine, dried (MgSO$_4$), filtered, and concentrated. The residue was redissolved in diethyl ether (300 mL) and extracted into 1M HCl (300 mL). The extract was made basic (pH 10) with 1M NaOH and extracted with ethyl acetate. The extract was washed with brine, dried (MgSO$_4$), filtered, and concentrated to provide 38 g of the desired product which was used in the next step without further purification.

step 35b: Compound 11b from Scheme 4

The product from step 35a (37 g) was dissolved in dichloromethane (230 mL) and treated with triethylamine (16.8 mL) followed by dropwise addition of acetic anhydride (11.2 mL) over 10 minutes at room temperature, stirred for 10 hours, diluted with dichloromethane (200 mL), washed sequentially with 5t aqueous NaHCO$_3$ and brine, dried (MgSO$_4$), filtered, and concentrated to provide 40 g of the desired product which was used in the next step without further purification.

step 35c: Compound 12 from Scheme 4

The product from step 35b (35.73 g) was processed as described in step 1h to provide 40.2 of the crude product which was purified by flash chromatography on silica gel with a gradient of from 98:1:1 dichloromethane/methanol/ammonium hydroxide to 94:5:1 dichloromethane/methanol/ammonium hydroxide to provide 20.5 g of the desired product.

step 35d: Compound 13 from Scheme 4

A solution of the product from step 35c (13.57 g, 0.02 mol) in THF (250 mL) 0° C. was treated first with 1, 1'-carbonyldiimidazole (16.8 g, 0.103 mol), then portionwise with sodium hydride (60% dispersion in mineral oil, 831 mg) over 20 minutes, stirred at room temperature for 6 days, recooled to 0° C., diluted with ethyl acetate (500 mL), washed sequentially with 5% aqueous sodium bicarbonate (150 mL), water (2×150 mL) and brine (2×200 mL), dried (Na$_2$SO$_4$), filtered, and concentrated. The residue was purified by flash chromatography on silica gel with a gradient of from 3:7 acetone/hexanes to 4:6 acetone/hexanes provide 5.75 g of the desired product.

step 35e: Compound 14 from Scheme 5

A slurry of the product from step 35d (1.5 g, 0.002 mol) in acetonitrile (15 mL) and water (1 mL) was treated with ethylenediamine (1.4 mL), stirred at room temperature for 2 hours, and concentrated. The residue was treated with ethyl acetate, washed with water, dried (Na$_2$SO$_4$), filtered and concentrated. The residue was purified by flash chromatography on silica gel with 97.5:2:0.5 dichloromethane:methanol:ammonium hydroxide to provide 0.904 g of the desired product.

step 35f: Compound 15 from Scheme 5

A solution of the product from step 35e (0.9 g, 1.25 mmol)in ethanol (25 mL) at room temperature was treated with acetic acid (285 µL), warmed to 78° C. for 18 hours, treated with ethyl acetate (150 mL), washed sequentially with 5% aqueous sodium bicarbonate (75 mL),and brine (2×75 mL), dried (Na$_2$SO$_4$), filtered, and concentrated. The residue was purified by flash chromatography on silica gel with 8:92 methanol/dichloromethane to provide 0.572 g of the desired product.

step 35g: Compound of Formula I: $R^b$ is H, L is —C(O)—, T is —NH—, R is —(CH$_2$)—C≡C—(5-(2-benzothiophenyl)-2-thienyl)

The product from step 35f (380 mg) was processed as described in step 7a (replacing 2-bromo-5-(4-pyrimidinyl)thiophene with 2-(5-bromo-2-thienyl)pyridine) and purified by flash chromatography on silica gel with a gradient of from 5:95 methanol/dichloromethane to 7:93 methanol/dichloromethane to provide 210 mg of the desired product.

High Resolution MS (FAB) calcd (M+H)$^+$ for C$_{44}$H$_{61}$N$_4$O$_9$S: 821.4154. Found 821.4161.

Example 36

Compound of Formula I: $R^b$ is H, L is —C(O)—, T is —N(W-R$^d$)—, W is —NH—, R$^d$ is H, R is —(CH$_2$)—C≡C—(5-(2-pyridyl)-2-thienyl)

step 36a: Compound 16 from Scheme 6

A solution of the product from step 35d (3 g, 4 mmol)in DMF (22 mL) was treated sequentially with 1-hexene (12 mL) and hydrazine (1.29 mL), warmed to 58° C. for 6 hours, treated with saturated aqueous NH4Cl, and extracted with ethyl acetate. The extract was washed sequentially with 5% aqueous sodium bicarbonate, water, and brine, dried (Na$_2$SO$_4$), filtered, and concentrated. The residue (2.2 g) was dissolved in methanol (50 mL), stirred for 20 hours, and concentrated. The residue was purified by flash chromatography on silica gel with 6:3.5:0.5 ethyl acetate/hexanes/ammonium hydroxide to 98.5:2:0.5 dichloromethane/methanol/ammonium hydroxide to provide 1.6 g of the desired product.

step 36b: Compound of Formula I: $R^b$ is H, L is —C(O)—, T is —N(W-$R^d$)—, W is —NH—, $R^d$ is H, R is —(CH$_2$)—C≡C—(5-(2-pyridyl)-2-thienyl)

A solution of the product from step 36a (350 mg) was processed as described in step 35 g to provide the crude product which was purified by flash chromatography on silica gel with 2:97.5:0.5 methanol/dichloromethane/ammonium hydroxide to provide 229 mg of the desired product.

High Resolution MS (FAB) calcd (M+H)$^+$ for $C_{42}H_{59}N_4O_{10}S$: 811.3946. Found 811.3945.

Example 37

Compound of Formula I: $R^b$ is H, L is —C(O)—, T is —NH—, R is —C(H)=CH—(5-(1H-imidazol-1-yl)-3-pyridyl)

step 37a: Compound of Formula I: $R^b$ is CH$_3$C(O)—, L is —C(O)—, T is —NH—, R is —C(H)=CH$_2$ The title compound was prepared as described in U.S. Pat. No. 5,866,549, Example 1, steps 1a–g and Example 102, steps 120a–c.

step 37b: 3-bromo-5-(1H-imidazol-1-yl)pyridine

A solution/slurry of 3,5-dibromopyridine (474 mg, 2.0 mmol) imidazole (136 mg, 2.0 mmol), Cs$_2$CO$_3$ (975 mg, 3.0 mmol, and CuO (50 mg) was heated in a sealed vessel for 18 hours, cooled to room temperature, treated with ethyl acetate, washed with 5% aqueous NaHCO$_3$ and brine, dried (Na$_2$SO$_4$), filtered, and concentrated. The residue was purified by flash chromatography on silica gel with a gradient of from 98:2 to 90:10 methanol/dichloromethane to provide 80 mg of the desired compound.

MS (DCI/NH$_3$) m/z 224 and 226 (M+H)$^+$.

Step 37c: Compound of Formula I: $R^b$ is H, L is —C(O)—, T is —NH—, R is —C(H)=CH—(5-(1H-imidazol-1-yl)-3-Dvridyl)

A solution/slurry of the product from step 37a (136 mg, 0.20 mmol), the product from step 37b (56 mg, 0.250 mmol), Pd(OAc)$_2$ (10 mg, 0.04 mmol), tri-o-tolylphosphine (18 mg, 0.060 mmol), and triethylamine (84 mL, 0.60 mmol) in degassed acetonitrile (2 mL) was heated at 50° C. in a sealed vessel for 14 hours, treated with additional Pd(OAc)$_2$ (10 mg), tri-o-tolylphosphine (18 mg), treated with ethyl acetate, washed with 5% aqueous NaHCO$_3$ and brine, dried (Na$_2$SO$_4$), filtered, and concentrated. The residue was stirred in methanol for 18 hours, concentrated, and purified by flash column chromatography on silica gel with 90:10:0.5 dichloromethane/methanol/ammonium hydroxide to provide 48 mg of the desired compound.

MS (ESI) 782 (M+H)$^+$.

Example 38

Compound of Formula I: $R^b$ is H, L is —C(O)—, T is —NH—, R is —C(H)=CH—(3-bromo-6-quinolinyl)

step 38a: Compound of Formula I: $R^b$ is CH$_3$C(O)—, R is —C(H)=CH—(3-bromo-6-quinolinyl)

Compound 21 from Scheme 12 (136 mg) was processed as described in step 37c (substituting 3-bromo-6-iodoquinoline for the product from step 37b) and purified by flash column chromatography on silica gel with 1:1:0.5 acetone/hexane/triethylamine to provide 170 mg of the desired product.

step 38b: Compound of Formula I: $R^b$ is H, L is —C(O)—, T is —NH—, R is —C(H)=CH—(3-bromo-6-quinolinyl)

The the product from step 38a (150 mg) was stirred in methanol (10 mL) at room temperature for 48 hours, concentrated, and purified by flash column chromatography on silica gel with 50:50:0.5 methanol/dichloromethane/ammonium hydroxide to provide 130 mg of the desired product.

MS (ESI) 844, 846 (M+H)$^+$.

Example 39

Compound of Formula I: $R^b$ is H, L is —C(O)—, T is —NH—, R is —C(H)=CH—(3-(2-furanyl)-6-quinolinyl)

step 39a: Compound of Formula I: $R^b$ is CH$_3$C(O)—, R is —C(H)=CH—(3-(2-furanyl)-6-quinolinyl)

A solution of the product from step 38a, (177 mg, 0.20 mmol), 2-tri-n-butylstannylfuran (78 mg, 0.25 mmol), tetrakis(triphenylphosphine)palladium(0) (23 mg, 0.020 mmol) in dry toluene (2 mL) was heated at 60° C. for 2, 80° C. for 2 hours, and 90° C. for 16 hours, cooled, treated with ethyl acetate, washed with 5% aqueous NaHCO$_3$ and brine, dried (Na$_2$SO$_4$), filtered, and concentrated. The residue was purified by flash column chromatography on silica gel with 1:1:0.5 acetone/hexane/triethylamine to provide the desired product.

step 39b: Compound of Formula I: $R^b$ is H, L is —C(O)—, T is —NH—, R is —C(H)=CH—(3-(2-furanyl)-6-quinolinyl)

The product from step 39a was processed as described in step 38b to provide 102 mg of the desired product.

MS (ESI) 832 (M+H)$^+$.

Example 40

Compound of Formula I: $R^b$ is H, L is —C(O)—, T is —NH—, R is —C(H)=CH—(5-bromo-3-pyridyl)

step 40a: Compound of Formula I: $R^b$ is CH$_3$C(O)—, L is —C(O)—, T is —NH—, R is —C(H)=CH—(5-bromo-3-pyridyl)

A solution/slurry of the product from step 37a (136 mg, 0.20 mmol), 3,5-dibromopyridine (125 mg, 0.527 mmol), Pd(C$_2$H$_3$O$_2$)$_2$ (10 mg, 0.04 mmol), tri-o-tolylphosphine (18 mg, 0.060 mmol), and triethylamine (84 mL, 0.60 mmol) in degassed acetonitrile (2 mL) was heated at 50° C. in a sealed vessel for 14 hours, treated with additional Pd(C$_2$H$_3$O$_2$)$_2$ (10 mg), tri-o-tolylphosphine (18 mg), treated with ethyl acetate, washed with 5% aqueous NaHCO$_3$ and brine, dried (Na$_2$SO$_4$), filtered, and concentrated. The residue was purified by flash column chromatography on silica gel with 1:1:0.5 acetone/hexane/triethylamine to provide 95 mg of the desired product.

step 40b: Compound of Formula I: $R^b$ is H, L is —C(O)—, T is —NH—, R is —C(H)=CH—(5-bromo-3-pyridyl)

The the product from step 38a (75 mg) was stirred in methanol (5 mL) at room temperature for 48 hours, concentrated, and purified by flash column chromatography on silica gel with 5:94.5:0.5 methanol/dichloromethane/ammonium hydroxide to provide 130 mg of the desired product.

MS (ESI) 794, 796 (M+H)$^+$.

Example 41

Compound of Formula I: $R^b$ is H, L is —C(O)—,
T is —NH—, R is —C(H)=CH—(5-(2-thienyl)-3-pyridyl)

step 41a: Compound of Formula I: $R^b$ is CH$_3$C(O)—, L is —C(O)—, T is —NH—, R is —C(H)=CH—(5-(2-thienyl)-3-pyridyl)

A solution of the product from step 40a, (167 mg, 0.20 mmol), tributyl(2-thienyl)stannane (79 μL, 0.25 mmol), tetrakis(triphenylphosphine)palladium(0) (23 mg, 0.020 mmol) in dry toluene (2 mL) was heated at 90° C. for 20 hours, cooled, treated with ethyl acetate, washed with 50% aqueous NaHCO$_3$ and brine, dried (Na$_2$SO$_4$), filtered, and concentrated. The residue was purified by flash column chromatography on silica gel with 50:50:0.5 acetone/hexane/triethylamine to provide the desired product.

step 41b: Compound of Formula I: $R^b$ is H, L is —C(O)—, T is —NH—, R is —C(H)=CH—(5-(2-thienyl)-3-pyridyl)

The product from step 41a was stirred in methanol at room temperature for 18 hours, concentrated, and purified by flash column chromatography on silica gel with 5:94.5:0.5 methanol/dichloromethane/ammonium hydroxide to provide 81.1 mg of the desired product.

MS (ESI) 798 (M+H)$^+$.

Example 42

Compound of Formula I: $R^b$ is H, L is —C(O)—,
T is —NH—, R is —C(H)=CH—(5-phenyl-3-pyridyl)

The product from step 40a, (167 mg) was processed as described in Example 41, steps 41a–b (substituting tributyl(phenyl)stannane for tributyl(2-thienyl)stannane) to provide 91.8 mg of the desired product.

MS (ESI) 792 (M+H)$^+$.

Example 43

Compound of Formula I: $R^b$ is H, L is —C(O)—,
T is —NH—, R is —C(H)=CH—(5-(2-pyridyl)-3-pyridyl)

The product from step 40a, (167 mg) was processed as described in Example 41, steps 41a–b (substituting 2-(tributylstannyl)pyridine for tributyl(2-thienyl)stannane) to provide 71.4 mg of the desired product.

MS (ESI) 793 (M+H)$^+$.

Example 44

Compound of Formula I: $R^b$ is H, L is —C(O)—T is —NH—, R is —C(H)=CH—(5-(3-quinolinyl)-3-pyridyl)

step 44a: Compound of Formula I: $R^b$ is CH$^3$C(O)—, L is —C(O)—, T is —NH—, R is —C(H)=CH—(5-(3-quinolinyl)-3-pyridyl)

A solution of the product from step 40a (167 mg, 0.2 mmol), hexamethylditin (78 mg, 0.24 mmol), tetrakis(triphenylphosphine)palladium(0) (23 mg, 0.02 mmol) and 3-bromoquinoline (27 mg, 0.2 mmol), in toluene (2 mL) was heated to 90° C. for 18 hours, cooled, treated with ethyl acetate, washed with 5% aqueous NaHCO$_3$ and brine, dried (Na$_2$SO$_4$), filtered, and concentrated. The residue was purified by flash column chromatography on silica gel with 50:50:0.5 acetone/hexane/triethylamine to provide the desired product.

step 44b: Compound of Formula I: $R^b$ is H, L is —C(O)—, T is —NH—, R is —C(H)=CH—(5-(3-quinolinyl)-3-pyridyl)

The product from step 44a was stirred in methanol at room temperature for 18 hours, concentrated, and purified by flash column chromatography on silica gel with 5:94.5:0.5 methanol/dichloromethane/ammonium hydroxide to provide 62.1 mg of the desired product.

MS (ESI) 843 (M+H)$^+$.

Example 45

Compound of Formula I: $R^b$ is H, L is —C(O)—,
T is —NH—, R is —C(H)=CH—(5-(5-pyrimidinyl)-3-pyridyl)

The product from step 40a, (167 mg) was processed as described in Example 44, steps 44a–b (substituting 5-bromopyrimidine for 3-bromoquinoline to provide 71.4 mg of the desired product.

MS (ESI) 794 (M+H)$^+$.

Example 46

Compound of Formula I: $R^b$ is H, L is —C(O)—,
T is —NH—, R is —C(H)=CH—(5-(2-pyrimidinyl)-3-pyridyl)

The product from step 40a, (167 mg) was processed as described in Example 44, steps 44a–b (substituting 2-bromopyrimidine for 3-bromoquinoline to provide 24.2 mg of the desired product.

MS (ESI) 794 (M+H)$^+$.

Example 47

Compound of Formula I: $R^b$ is H, L is —C(O)—,
T is —NH—, R is —C(H)=CH—(5-(3-pyridyl)-3-pyridyl)

The product from step 40a, (417 mg) was processed as described in Example 41, steps 41a–b (substituting 3-(tributylstannyl)pyridine for tributyl(2-thienyl)stannane) to provide 202 mg of the desired product.

MS (ESI) 793 (M+H)$^+$.

Example 48

Compound of Formula I: $R^b$ is H, L is —C(O)—,
T is —NH—, R is —C(H)=CH—(5-(4-isoquinolinyl)-3-pyridyl)

The product from step 40a, (167 mg) was processed as described in Example 44, steps 44a–b (substituting 4-bromoisoquinoline for 3-bromoquinoline to provide 24.2 mg of the desired product.

MS (ESI) 843 (M+H)$^+$.

Example 49

Compound of Formula I: $R^b$ is H, L is —C(O)—,
T is —NH—, R is —C(H)=CH—(5-(3-thienyl)-3-pyridyl)

The product from step 40a, (167 mg) was processed as described in Example 44, steps 44a–b (substituting 3-bromothiophene for 3-bromoquinoline to provide 24.2 mg of the desired product.

MS (ESI) 798 (M+H)$^+$.

Example 50

Compound of Formula I: $R^b$ is H, L is —C(O)—,
T is —NH—, R is —C(H)=CH—(5-(2-furyl)-3-pyridyl)

The product from step 40a, (167 mg) was processed as described in Example 41, steps 41a–b (substituting tributyl (2-furyl)stannane for tributyl(2-thienyl)stannane) to provide 202 mg of the desired product.

MS (ESI) 782 (M+H)$^+$.

Example 51

Compound of Formula I: R$^b$ is H, L is —C(O)—, T is —NH—, R is —C(H)=CH—(5-(2-(1,3-thiazolyl))-3-pyridyl)

The product from step 40a, (167 mg) was processed as described in Example 41, steps 41a–b (substituting 2-(tributylstannyl)-1,3-thiazole for tributyl(2-thienyl) stannane) to provide 67.2 mg of the desired product.

MS (ESI) 799 (M+H)$^+$.

Example 52

Compound of Formula I: R$^b$ is H, L is —C(O)—, T is —NH—, R is —C(H)=CH—(5-(5-(1,3-thiazolyl))-3-pyridyl)

step 52a: Compound of Formula I: R$^b$ is H, L is —C(O)—, T is —NH—, R is —C(H)=CH—(5-(2-(trimethylsilyl)-1,3-thiazol-5-yl)-3-pyridyl)

The product from step 40a, (167 mg) was processed as described in step 41a (substituting 5-(tributylstannyl)-2-(trimethylsilyl)-1,3-thiazole for tributyl(2-thienyl)stannane) to provide the desired product.

step 52b: Compound of Formula I: R$^b$ is CH$_3$C(O)—, L is —C(O)—, T is —NH—, R is —C(H)=CH—(5-(1,3-thiazolyl)-3-pyridyl)

A solution of the product from step 52a in THF at room temperature was treated with 5% HCl. stirred for 1 hour, treated with ethyl acetate, washed with 5% aqueous NaHCO$_3$ and brine, dried (Na$_2$SO$_4$), filtered, and concentrated. The residue was purified by flash column chromatography on silica gel with 1:1:0.5 acetone/hexane/triethylamine to provide the desired product.

step 52c: Compound of Formula I: R$^b$ is H, L is —C(O)—, T is —NH—, R is —C(H)=CH—(5-(5-(1,3-thiazolyl))-3-pyridyl)

The product from step 52b was stirred in methanol at room temperature for 18 hours, concentrated, and purified by flash column chromatography on silica gel with 50:50:0.5 methanol/dichloromethane/ammonium hydroxide to provide 85.3 mg of the desired product.

MS (ESI) 799 (M+H)$^+$.

Example 53

Compound of Formula I: R$^b$ is H, L is —C(O)—, T is —NH—, R is —C(H)=CH—(5-(2-amino-(1,3-thiazol-5-yl))-2-thienyl)

step 53a: Compound of Formula I: R$^b$ is CH$_3$C(O)—, L is —C(O)—, T is —NH—, R is —C(H)=CH—B(OH)$_2$ A solution of borane-THF complex (1M in THF, 11.8 mL 11.8 mmol) at –10° C. was treated with 2-methyl-2-butene (2.7 mL, 24 mmol), stirred at 0° C. for 2 hours, treated in one portion with a solution of the product from Step 1h (2 g, 2.95 mmol) in THF (10 mL), stirred at 0° C. for 1 hour and at room temperature for 3 hours, recooled to 0° C., treated with and 5% aqueous sodium carbonate, and extracted with ethyl acetate. The extracts were washed with brine, dried (MgSO$_4$), filtered, and concentrated. The residue was purified by flash chromatography on silica gel with 1:1 acetone/hexanes to provide 3.6 g of the desired compound.

step 53b: Compound of Formula I: R$^b$ is H, L is —C(O)—, T is —NH—, R is C(H)=CH—(5-(2-amino-(1,3-thiazol-5-yl))-2-thienyl)

A solution/slurry of the product from step 53a, (72 mg, 0.10 mmol), sodium carbonate (31 mg, 0.30 mmol), tetrakis (triphenylphosphine)palladium(0) (12 mg, 0.010 mmol), and 5-(5-bromo-2-thienyl)-1,3-thiazol-2-amine (52 mg, 0.20 mmol) in 1:1 acetone/water (2 mL) in a sealed vessel was heated at 60° C. for 2 hours and at 80° C. for 2 hours, cooled, treated with ethyl acetate, washed with 5% aqueous NaHCO$_3$ and brine, dried (Na$_2$SO$_4$), filtered, and concentrated. The residue was dissolved in methanol (5 mL), stirred for 24 hours, and concentrated. The residue was purified by flash chromatography on silica gel with 5:94.5:0.5 methanol/dichloromethane/ammonium hydroxide then purified again by flash chromatography on silica gel with 95:5:0.5 acetone/hexane/triethylamine to provide to provide 26.7 mg of the desired product.

MS (ESI) 819 (M+H)$^+$.

Example 54

Compound of Formula I: R$^b$ is H, L is —C(O)—, T is —NH—, R is —C(H)=CH—(5-(3-pyridyl)-2-(1,3-thiazolyl))

A solution/slurry of the product from step 53a, (144 mg, 0.10 mmol), sodium carbonate (62 mg, 0.60 mmol), tetrakis (triphenylphosphine)palladium(0) (23 mg, 0.020 mmol), and 3-(2-bromo-1,3-thiazol-5-yl)pyridine (72 mg, 0.30 mmol) in 2:1 toluene/water (3 mL) in a sealed vessel was heated at 80° C. for 16 hours, cooled, treated with ethyl acetate, washed with 5% aqueous NaHCO$_3$ and brine, dried (Na$_2$SO$_4$), filtered, and concentrated. The residue was dissolved in methanol (5 mL), stirred at room temperature for 16 hours, and concentrated. The residue was purified by flash chromatography on silica gel with 75:24.5:0.5 acetone/hexane/triethylamine to provide to provide 126.5 mg of the desired product.

MS (ESI) 799 (M+H)$^+$.

Example 55

Compound of Formula I: R$^b$ is H, L is —C(O)—, T is —NH—, R is —C(H)=CH—(2-(3-pyridyl)-5-(1,3-thiazolyl))

A solution/slurry of the product from step 53a, (144 mg, 0.10 mmol), sodium carbonate (62 mg, 0.60 mmol), tetrakis (triphenylphosphine)palladium(0) (23 mg, 0.020 mmol), and 3-(5-bromo-1,3-thiazol-2-yl)pyridine (72 mg, 0.30 mmol) in 2:1 toluene/water (3 mL) in a sealed vessel was heated at 80° C. for 24 hours, cooled, treated with ethyl acetate, washed with 5% aqueous NaHCO$_3$ and brine, dried (Na$_2$SO$_4$), filtered, and concentrated. The residue was dissolved in methanol (5 mL), stirred at room temperature for 16 hours, and concentrated. The residue was purified by flash chromatography on silica gel with 75:24.5:0.5 acetone/hexane/triethylamine to provide to provide 72 mg of the desired product.

MS (ESI) 799 (M+H)$^+$.

Example 56

Compound of Formula I: R$^b$ is H, L is —C(O)—, T is —NH—, R is —C(H)=CH—(2-(5-bromo-113-thiazol-2-yl)-5-(1,3-thiazolyl))

step 56a: Compound of Formula I: R$^b$ is CH$_3$C(O)—, L is —C(O)—, T is —NH—, R is —C(H)=CH—(2-(5-bromo-(1,3-thiazol-2-yl))-5-(1,3-thiazolyl))

A solution/slurry of the product from step 53a, (400 mg, 0.80 mmol), sodium carbonate (168 mg, 1.6 mmol), tetrakis (triphenylphosphine)palladium(0) (23 mg, 0.020 mmol), and 2-(5-bromo-1,3-thiazol-2-yl)-5-bromo-1,3-thiazole (52 mg, 0.20 mmol) in 2:1 toluene/water (6 mL) in a sealed vessel was heated at 50° C. for 1 hour and at 80° C. for 16 hours, cooled, treated with ethyl acetate, washed with 5% aqueous NaHCO$_3$ and brine, dried (Na$_2$SO$_4$), filtered, and concentrated. The residue was purified by flash chromatography on silica gel with 50:50:0.5 acetone/hexane/triethylamine to provide to provide 187 mg of the desired product.

step 56b: Compound of Formula I: $R^b$ is H, L is —C(O)—, T is —NH—, R is —C(H)=CH—(2-(5-bromo-1,3-thiazol-2-yl)-5-(1,3-thiazolyl)) A solution of the product from step 56a (50 mg) was stirred in methanol at room temperature for 16 hours and concentrated. The residue was purified by flash chromatography on silica gel with 75:24.5:0.5 acetone/hexane/triethylamine to provide to provide 50 mg of the desired product.

MS (ESI) 883 (M+H)$^+$.

Example 57

Compound of Formula I: $R^b$ is H, L is —C(O)—, T is —NH—, R is —C(H)=CH—(2-(2-thienyl)-5-thiazolyl)

step 57a: Compound of Formula I: $R^b$ is CH$_3$C(O)—, L is —C(O)—, T is —NH—, R is —C(H)=CH—(2-(2-thienyl)-5-thiazolyl)

A solution/slurry of the product from step 53a, (470 mg, 0.650 mmol), sodium carbonate (172 mg, 1.64 mmol), tetrakis(triphenylphosphine)palladium(0) (58 mg, 0.050 mmol), and 5-bromo-2-(2-thienyl)-1,3-thiazole (200 mg, 0.820 mmol) in 25:1 toluene/water (52 mL) in a sealed vessel was heated at 50° C. for 1 hour and at 80° C. for 16 hours, cooled, treated with ethyl acetate, washed with 5% aqueous NaHCO$_3$ and brine, dried (Na$_2$SO$_4$), filtered, and concentrated. The residue was purified by flash chromatography on silica gel with 50:50:0.5 acetone/hexane/triethylamine to provide to provide 400 mg of the desired product.

step 57b: Compound of Formula I: $R^b$ is H, L is —C(O)—, T is —NH—, R is —C(H)=CH—(2-(2-thienyl)-5-thiazolyl)

A solution of the product from step 56a (400 mg) was stirred in methanol (20 mL) at room temperature for 16 hours and concentrated. The residue was purified by flash chromatography on silica gel with 95:4.5:0.5 dichloromethane/methanol/ammonium hydroxide to provide to provide 344 mg of the desired product.

MS (ESI) 804 (M+H)$^+$.

Example 58 step 58a: Compound of Formula I: $R^b$ is CH$_3$C(O)—, L is —C(O)—, T is —NH—, R is —C(H)=CH—(2-(2-pyrazinyl)-5-(1,3-thiazolyl))

A solution/slurry of the product from step 53a, (158 mg, 0.332 mmol), sodium carbonate (3 equivalents), tetrakis (triphenylphosphine)palladium(0) (0.1 equivalents), and 2-(5-bromo-1,3-thiazol-2-yl)pyrazine (1.5 equivalents) in 2:1 toluene/water (6 mL) in a sealed vessel was heated at 80° C. for 20 hours, cooled, treated with ethyl acetate, washed with 5% aqueous NaHCO$_3$ and brine, dried (Na$_2$SO$_4$), filtered, and concentrated. The residue was purified by flash chromatography on silica gel with 50:50:0.5 acetone/hexane/triethylamine to provide to provide 103 mg of the desired product.

step 58b: Compound of Formula I: $R^b$ is H, L is —C(O)—, T is —NH—, R is —C(H)=CH—(2-(2-pyrazinyl)-5-(1,3-thiazolyl))

The residue was dissolved in methanol (5 mL), stirred at room temperature for 20 hours, and concentrated. The residue was purified by flash chromatography on silica gel with 95:4.5:0.5 dichloromethane/methanol/ammonium hydroxide to provide to provide 344 mg of the desired product.

MS (ESI) 800 (M+H)$^+$.

Example 59

Compound of Formula I: $R^b$ is H, L is —C(O)—, T is —NH—, R is —C(H)=CH—(2-(5-pyrimidinyl)-5-(1,3-thiazolyl))

The product from step 53a (180 mg) was processed as described in Example 58, steps 58a–b, (substituting 5-(5-bromo-1,3-thiazol-2-yl)pyrimidine for 2-(5-bromo-1,3-thiazol-2-yl)pyrazine) to provide 43 mg of the desired product.

MS (ESI) 800 (M+H)$^+$.

Example 60

Compound of Formula I: $R^b$ is H, L is —C(O)—, T is —NH—, R is —C(H)=CH—(2-(5-(1,3-thiazol-5-yl)-5-(1,3-thiazolyl))

The product from step 53a (247 mg) was processed as described in Example 58, steps 58a–b, (substituting 2-(1,3-thiazol-5-yl)-5-bromo-1,3-thiazole for 2-(5-bromo-1,3-thiazol-2-yl)pyrazine) to provide 131 mg of the desired product.

MS (ESI) 805 (M+H)$^+$.

Example 61

Compound of Formula I: $R^b$ is H, L is —C(O)—, T is —NH—, R is —C(H)=CH—(5-(2-pyrimidinyl)-2-thienyl)

The product from step 53a (250 mg) was processed as described in Example 58, steps 58a–b, (substituting 2-(5-bromo-2-thienyl)pyrimidine for 2-(5-bromo-1,3-thiazol-2-yl)pyrazine and heating at 100° C. for 48 hours) to provide 92 mg of the desired product. MS (ESI) 799 (M+H)$^+$.

Example 62

Compound of Formula I: $R^b$ is H, L is —C(O)—, T is —NH—, R is —C(H)=CH—(5-(2-pyrazinyl)-2-thienyl)

The product from step 53a (880 mg) was processed as described in Example 58, steps 58a–b, (substituting 2-(5-bromo-2-thienyl)pyrazine for 2-(5-bromo-1,3-thiazol-2-yl)pyrazine and heating at 100° C. for 24 hours) to provide 350 mg of the desired product.

MS (ESI) 799 (M+H)$^+$.

Example 63

Compound of Formula I: $R^b$ is H, L is —C(O)—, T is —NH—, R is —C(H)=CH—(5-(2-(1,3-thiazolyl)-2-thienyl)

The product from step 53a (220 mg) was processed as described in Example 58, steps 58a–b, (substituting 2-(5- bromo-2-thienyl)-1,3-thiazole for 2-(5-bromo-1,3-thiazol-2-yl)pyrazine and heating at 100° C. for 24 hours) to provide 86 mg of the desired product.

MS (ESI) 805 (M+H)$^+$.

Example 64

Compound of Formula I: $R^b$ is H, L is —C(O)—, T is —NH—, R is —C(H)=CH—(5-(4-pyrimidinyl)-2-thienyl)

The product from step 53a (250 mg) was processed as described in Example 58, steps 58a–b, (substituting 4-(5-bromo-2-thienyl)pyrimidine for 2-(5-bromo-1,3-thiazol-2-yl)pyrazine and heating at 100° C. for 24 hours) to provide 64 mg of the desired product.

MS (ESI) 799 (M+H)$^+$.

Example 65

Compound of Formula I: $R^b$ is H, L is —C(O)—, T is —NH—, R is —C(H)=CH—(4-(3-pyridyl)-2-(1,3-thiazolyl))

step 65a: Compound of Formula I: $R^b$ is $CH_3C(O)$—, L is —C(O)—, T is —NH—, R is —C(H)=CH—(4-bromo-2-(1,3-thiazolyl))

The product from step 53a (362 mg) was processed as described in Example 55 (substituting 1,4-dibromo-1,3-thioazole for 3-(5-bromo-1, 3-thiazol-2-yl)pyridine) to provide 384 mg of the desired compound.

step 65b: Compound of Formula I: $R^b$ is H, L is —C(O)—, T is —NH—, R is —C(H)=CH—(4-(3-pyridyl)-2-(1,3-thiazolyl))

The product from step 65a (170) was processed as described in Example 41, steps 41a–b, (substituting 3-(tributylstannyl)pyridine for tributyl(2-thienyl)stannane) to provide 25.6 mg of the desired product.

MS (ESI) 799 (M+H)$^+$.

Example 66

Compound of Formula I: $R^b$ is H, L is —C(O)—, T is —NH—, R is —C(H)=CH—(4-(3-pyridyl)-2-(1,3-thiazolyl))

The product from step 65a (100 mg) was processed as described in Example 41, steps 41a–b, (substituting 2-(tributylstannyl)-1,3-thiazole for tributyl(2-(1,3-thiazolyl) stannane) to provide 80 mg of the desired product.

MS (ESI) 805 (M+H)$^+$.

Example 67

Compound of Formula I: $R^b$ is H, L is —C(O)—, T is —NH—, R is —C(H)=CH—(4-(2-thienyl)-2-(1,3-thiazolyl))

The product from step 65a (100 mg) was processed as described in Example 41, steps 41a–b, (substituting 2-(tributylstannyl)-1,3-thiazole for tributyl(2-(1,3-thiazolyl) stannane and heating at 60° C. for 2 hours and at 90° C. for 20 hours) to provide 42.7 mg of the desired product.

MS (ESI) 804 (M+H)$^+$.

Example 68

Compound of Formula I: $R^b$ is H, R is —C(H)=CH—(5-(3-pyridyl)-2-thienyl)

step 68a: Compound of Formula I: $R^b$ is $CH^3C(O)$—, L is —C(O)—, T is —NH—, R is —C(H)=CH—(5-iodo-2-thienyl)

A solution/slurry of the product from step 53a (724 mg, 1.0 mmol), 2,5-diiodothiophene (672 g, 2.0 mmol), sodium carbonate (315 g, 3.0 mol), and tetrakis(triphenylphosphine)palladium(0) (58 g, 0.05 mmol) was heated at 90° C. for 44 hours, cooled, treated with ethyl acetate, washed with 5% aqueous $NaHCO_3$ and brine, dried ($Na_2SO_4$), filtered, and concentrated. The residue was purified by flash column chromatography on silica gel with 50:50:0.5 acetone/hexane/triethylamine to provide 340 mg of the desired product.

step 68b: Compound of Formula I: $R^b$ is H, L is —C(O)—, T is —NH—, R is —C(H)=CH—(5-(3-pyridyl)-2-thienyl)

The product from step 65a (100 mg) was processed as described in Example 41, steps 41a–b, (substituting 3-(tributylstannyl)pyridine for tributyl(2-(1,3-thiazolyl) stannane and heating at 80° C. for 2 hours and at 100° C. for 6 hours) to provide 40.9 mg of the desired product.

MS (ESI) 798 (M+H)$^+$.

Example 69

Compound of Formula I: $R^b$ is L is —C(O)—, T is —NH—, R is H, —C(H)=CH—(5-(2-pyrazinyl)-2-thienyl)

steep 69a: Compound of Formula I: $R^b$ is $CH_3C(O)$—, L is —C(O)—, T is —NH—, R is —C(H)=CH—(5-bromo-2-thienyl)

The product from step 53a was processed as described in step 68a (substituting 2,5-dibromothiophene for 2,5-diiodothiophene to provide 127 mg of the desired product.

step 69b: Compound of Formula I: $R^b$ is H, L is —C(O)—, T is —NH—, R is —C(H)=CH—(5-(2-pyrazinyl)-2-thienyl)

The product from step 69a (420 mg) was processed as described in Example 41, steps 41a–b, (substituting 2-(tributylstannyl)pyrazine for tributyl(2-(1,3-thiazolyl) stannane) to provide 127 mg of the desired product.

MS (ESI) 799 (M+H)$^+$.

Example 70

Compound of Formula I: $R^b$ is H, L is —C(O)—, T is —NH—, R is —C(H)=CH—(5-(5-pyrimidinyl)-2-thienyl)

The product from step 69a (250 mg) was processed as described in Example 41, steps 41a–b, (substituting 5-(tributylstannyl)pyrimidine for tributyl(2-(1,3-thiazolyl) stannane) to provide 377 mg of the desired product.

MS (ESI) 799 (M+H)$^+$.

Example 71

Compound of Formula I: $R^b$ is H, L is —C(O)—, T is —NH—, R is —C(H)=CH—(5-(3,4-dichlorophenyl)-2-thienyl)

The product from step 69a (120 mg) was processed as described in Example 44, steps 44a–b, (substituting 4-bromo-1,2-dichlorobenzene for 3-bromoquinoline) to provide 20 mg of the desired product.

MS (ESI) 866 (M+H)$^+$.

Example 72

Compound of Formula I: $R^b$ is H, L is —C(O)—, T is —NH—, R is —C(H)=CH—(5-(3-fluoroihenyl)-2-thienyl)

The product from step 69a (120 mg) was processed as described in Example 44, steps 44a–b, (substituting 1-bromo-3-fluorobenzene for 3-bromoquinoline) to provide 26 mg of the desired product.

Example 73

Compound of Formula I: $R^b$ is H, L is —C(O)—, T is —NH—, R is —C(H)=CH—(5-(5-(1,3-thiazoyl))-2-thienyl)

The product from step 69a (175 mg) was processed as described in Example 52, steps 52a–c, (substituting 5-(tributylstannyl)-2-(trimethylsilyl)-1,3-thiazole for tributylstannyl)-2-(trimethylsilyl)-1,3-thiazole) to provide 25 mg of the desired product.

MS (ESI) 816 (M+H)$^+$.

Example 74

Compound of Formula I: $R^b$ is H, L is —C(O)—, T is —NH—, R is —C(H)=CH—(2.2'-bisthienyl)

The product from step 69a (175 mg) was processed as described in Example 41, steps 41a–b, to provide 9 mg of the desired product.

MS (ESI) 804 (M+H)$^+$.

Example 75

Compound of Formula I: $R^b$ is H, L is —C(O)—, T is —NH—, R is —C(H)=CH—(5-(2-pyridyl)-2-thienyl)

The product from step 69a (120 mg) was processed as described in Example 41, steps 41a–b, (substituting 2-(tributylstannyl)pyridine for tributyl(2-(1,3-thiazolyl)stannane) to provide 71 mg of the desired product.

MS (ESI) 799 (M+H)$^+$.

Example 76

Compound of Formula I: $R^b$ is H, L is —C(O)—, T is —NH—, R is —C(H)=CH—(5-(3-thienyl)-2-thienyl)

The product from step 69a (150 mg) and 3-thienylboronic acid (30 mg) were processed as described in Example 41, steps 41a–b to provide 79 mg of the desired product.

MS (ESI) 804 (M+H)$^+$.

Example 77

Compound of Formula I: $R^b$ is H, L is —C(O)—, T is —NH—, R is —C(H)=CH—(5-(2-furanyl)-2-thienyl)

The product from step 69a (120 mg) and 2-(tributylstannyl)furan (66 mg) were processed as described in Example 41, steps 41a–b, to provide 74 mg of the desired product. MS (ESI) 787 (M+H)$^+$.

We claim:

1. A compound selected from the group consisting of a compound of formula I

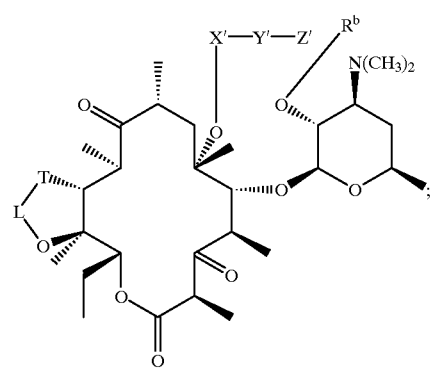

a compound of formula II

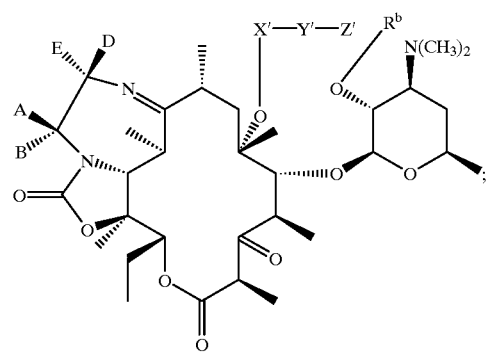

and a compound of formula III

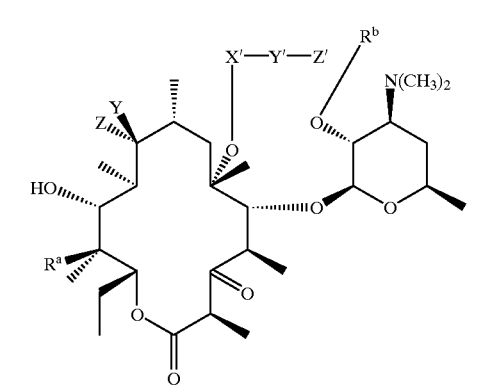

or a pharmaceutically acceptable salt, solvate, ester or prodrug thereof, wherein either:
  (a) Y and Z taken together define a group X,
    and X is selected from the group consisting of
      (1) =O,
      (2) =N—OH,
      (3) =N—O—R$^1$ where R$^1$ is selected from the group consisting of
        (a) unsubstituted $C_1$–$C_{12}$ alkyl,
        (b) $C_1$–$C_{12}$ alkyl substituted with aryl,
        (c) $C_1$–$C_{12}$ alkyl substituted with substituted aryl, (d) $C_1$–$C_{12}$ alkyl substituted with heteroaryl,
(e) $C_1$–$C_{12}$ alkyl substituted with substituted heteroaryl,
(f) $C_3$–$C_{12}$ cycloalkyl, and
(g) —Si—($R^2$)($R^3$)($R^4$) wherein $R^2$, $R^3$ and $R^4$ are each independently selected from the group consisting of $C_1$–$C_{12}$ alkyl and aryl; and
(4) =N—O—C($R^5$)($R^6$)—O—$R^1$ where $R^1$ is as previously defined and $R^5$ and $R^6$ are each independently selected from the group consisting of
(a) hydrogen,
(b) unsubstituted $C_1$–$C_{12}$ alkyl,
(c) $C_1$–$C_{12}$ alkyl substituted with aryl,
(d) $C_1$–$C_{12}$ alkyl substituted with substituted aryl,
(e) $C^1$–$C_{12}$ alkyl substituted with heteroaryl, and
(f) $C^1$–$C_{12}$ alkyl substituted with substituted heteroaryl,
or $R^5$ and $R^6$ taken together with the atom to which they are attached form a $C_3$–$C_{12}$ cycloalkyl ring; or
(b) one of Y and Z is hydrogen and the other is selected from the group consisting of
(1) hydrogen,
(2) hydroxy,
(3) protected hydroxy, and
(4) $NR^7R^8$ wherein $R^7$ and $R^8$ are independently selected from the group consisting of hydrogen and $C_1$–$C_6$ alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)-, —N(heteroaryl-$C_1$–$C_6$-alkyl-)—, —N(substituted-heteroaryl-$C_1$–$C_6$-alkyl-)—, and —S— or —S(O)$_n$—, wherein n is 1 or 2;
$R^a$ is hydrogen or hydroxy;
$R^b$ is hydrogen or a hydroxy protecting group;
L is methylene or carbonyl, provided that when L is methylene, T is —O—;
T is selected from the group consisting of —O—, —NH—, and —N(W-$R^d$)—, wherein W is absent or is selected from the group consisting of —O—, —NH—CO—, —N=CH— and —NH—, and $R^d$ is selected from the group consisting of
(1) hydrogen,
(2) $C_1$–$C_6$ alkyl optionally substituted with one or more substituents selected from the group consisting of
(a) aryl,
(b) substituted aryl,
(c) heteroaryl,
(d) substituted heteroaryl,
(e) hydroxy,
(f) $C_1$–$C^6$ alkoxy,
(g) $NR^7R^8$, wherein $R^7$ and $R^8$ are as defined previously, and
(h) —$CH_2$—M—$R^9$,
wherein M is selected from the group consisting of
(i) —C(O)—NH—,
(ii) —NH—C(O)—,
(iii) —NH—,
(iv) —N=,
(v) —N($CH_3$)—,
(vi) —NH—C(O)—O—

(vii) —NH—C(O)—NH—
(viii) —O—C(O)—NH—
(ix) —O—C(O)—O—
(x) —O—,
(xi) —S(O)$_n$—, wherein n is 0, 1 or 2,
(xii) —C (O)—O—,
(xiii) —O—C(O)—, and
(xiv)—C(O)—; and
wherein $R^9$ is selected from the group consisting of:
(i) $C_1$–$C_6$ alkyl, optionally substituted with a substituent selected from the group consisting of
(aa) aryl,
(bb) substituted aryl,
(cc) heteroaryl, and
(dd) substituted heteroaryl;
(ii) aryl,
(iii) substituted aryl,
(iv) heteroaryl,
(v) substituted heteroaryl, and
(vi) heterocycloalkyl;
(3) $C_3$–$C_7$ cycloalkyl,
(4) aryl,
(5) substituted aryl,
(6) heteroaryl, and
(7) substituted heteroaryl;
X' is selected from the group consisting of $C_1$–$C_{10}$ alkyl, $C_3$–$C_{10}$ alkenyl, and $C_3$–$C_{10}$ alkynyl;
Y' and Z' are independently selected from the group consisting of:
(c) optionally substituted aryl, and
(d) optionally substituted heteroaryl,
with the proviso that both Y' and Z' are not both phenyl, and with the further proviso that Y' is not isoxazole when Z' is thiophenyl;
and A, B, D and E are independently selected from the group consisting of:
(a) hydrogen;
(b) $C_1$–$C_6$ alkyl, optionally substituted with one or more substituents selected from the group consisting of:
(i) aryl;
(ii) substituted aryl;
(iii) heteroaryl;
(iv) substituted heteroaryl;
(v) heterocycloalkyl;
(vi) hydroxy;
(vii) $C_1$–$C_6$ alkoxy;
(viii) halogen consisting of Br, Cl, F or I; and
(ix) $NR^7R^8$, wherein $R^7$ and $R^8$ are as previously defined;
(c) $C_3$–$C_7$ cycloalkyl;
(d) aryl;
(e) substituted aryl;
(f) heteroaryl;
(g) substituted heteroaryl;
(h) heterocycloalkyl; and
(i) a group selected from option (b) as above defined A, B, D and E further substituted with —M—$R^9$, wherein M and $R^9$ are as previously defined, with the proviso that at least two of A, B, D and E are hydrogen;
or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$alkyl-)—, —N(aryl-$C_1$–$C_6$ alkyl-)—, —N(substituted aryl-$C_1$–$C_6$ alkyl-)—, —N(heteroaryl-$C_1$–$C_6$ alkyl-)—, —N(substituted heteroaryl- $C_1$–$C_6$ alkyl-)—, —S— or —S(O)$_n$—, wherein n is 1 or 2, —C(O)—NH, —C(O)—NR$^{12}$—, wherein R$^{12}$ is selected from the group consisting of hydrogen, $C_1$–$C_3$ alkyl, $C_1$–$C_3$ alkyl substituted with aryl, substituted aryl, heteroaryl, or substituted heteroaryl, —NH—C(O)—, and —NR$^{12}$—C(O)—.

2. A compound according to claim 1 wherein L is carbonyl.

3. A compound according to claim 1 wherein T is —NH—.

4. A compound according to claim 1 wherein R$^b$ is a hydroxy protecting group.

5. A compound according to claim 1 wherein R$^b$ is hydrogen.

6. A compound according to claim 1 wherein X' is $C_3$ alkenyl.

7. A compound according to claim 1 wherein X' is $C_3$ alkynyl.

8. A compound according to claim 1 wherein Y' and Z' are independently selected from the group consisting of thienyl, furanyl, pyridyl, pyrimidinyl, piperidinyl, phenyl, naphthyl, benzothiophenyl, benzofuranyl, thiazolyl, pyrazinyl, quinoxalinyl, imidazolyl, triazolyl, tetrazolyl, benzimidazolyl, quinolinyl, and isoquinolinyl, all of which may be optionally substituted.

9. A compound according to claim 8 wherein Y' is thienyl.

10. A compound according to claim 8 wherein Z' is pyridyl.

11. A compound according to claim 1, wherein —X', Y', and Z' combine to form a group R, and R is selected from the group consisting of
—(CH$_2$)—C≡C—(5-(2-pyridyl)-2-thienyl),
—(CH$_2$)—C≡C—(5-(3-pyridyl)-2-thienyl),
—(CH$_2$)—C≡C—(5-(4-pyridyl)-2-thienyl),
—(CH$_2$)—C≡C—(5-(5-pyrimidinyl)-2-thienyl),
—(CH$_2$)—C≡C—(5-(2-pyrimidinyl)-2-thienyl),
—(CH$_2$)—C≡C—(5-(2-pyrazinyl)-2-thienyl),
—(CH$_2$)—C≡C—(5-(5-cyano-3-pyridyl)-2-thienyl),
—(CH$_2$)—C≡C—(5-(5-carboxamido-3-pyridyl)-2-thienyl),
—(CH$_2$)—C≡C—(5-(5-ethoxycarbonyl-3-pyridyl)-2-thienyl),
—(CH$_2$)—C≡C—(5-(5-N,N-dimethylcarboxamido-3-pyridyl)-2-thienyl),
—(CH$_2$)—C≡C—(5-(5-N',N'-dimethylhydrazidocarbonyl-3-pyridyl)-2-thienyl),
—(CH$_2$)—C≡C—(5-(phenyl)-2-thienyl),
—(CH$_2$)—C≡C—(5-(3-methoxyphenyl)-2-thienyl),
—(CH$_2$)—C≡C—(5-(3-fluorophenyl)-2-thienyl),
—(CH$_2$)—C≡C—(5-(3-chlorophenyl)-2-thienyl),
—(CH$_2$)—C≡C—(5-(3,5-dichlorophenyl)-2-thienyl)
—(CH$_2$)—C≡C—(5-(3-methylphenyl)-2-thienyl),
—(CH$_2$)—C≡C—(5-(3-trifluoromethylphenyl)-2-thienyl),
—(CH$_2$)—C≡C—(5-(3-acetamidophenyl)-2-thienyl),
—(CH$_2$)—C≡C—(5-(3-nitrophenyl)-2-thienyl),
—(CH$_2$)—C≡C—(5-(4-fluorophenyl)-2-thienyl),
—(CH$_2$)—C≡C—(5-(2-furanyl)-2-thienyl),
—(CH$_2$)—C≡C—(4-(5-formyl-2-furanyl)phenyl),
—(CH$_2$)—C≡C—C4-(5-formyl-2-furanyl)phenyl),
—(CH$_2$)—C≡C—(4-(5-formyl-2-furanyl)phenyl),
—(CH$_2$)—C≡C—(2,2'-bisthienyl),
—(CH$_2$)—C≡C—(2-(5-chloro-2-thienyl) thienyl),
—(CH$_2$)—C≡C—(2,3'-bis(thienyl)),
—(CH$_2$)—C≡C—(5-(2-thiazolyl)-2-thienyl),
—(CH$_2$)—C≡C—(5-(5-thiazolyl)-2-thienyl),
—(CH$_2$)—C≡C—(5-(4-thiazolyl)-2-thienyl),
—(CH$_2$)—C≡C—(5-(2-methyl-5-thiazoyl)-2-thienyl),
—(CH$_2$)—C≡C—(5-(1-methyl-2-imidazolyl)-2-thienyl),
—(CH$_2$)—C≡C—(5-(2-quinoxalinyl)-2-thienyl),
—(CH$_2$)—C≡C—(5-(2-benzothiophenyl)-2-thienyl),
—(CH$_2$)—C≡C—(5-(2-pyridyl)-2-thienyl),
—(CH$_2$)—C≡C—(5-(2-benzothiophenyl)-2-thienyl),
—C(H)=CH—(5-(1H-imidazol-1-yl)-3-pyridyl),
—C(H)=CH—(3-(2-furanyl)-6-quinolinyl),
—C(H)=CH—(5-(2-thienyl)-3-pyridyl),
—C(H)=CH—(5-phenyl-3-pyridyl),
—C(H)=CH—(5-(2-pyridyl)-3-pyridyl),
—C(H)=CH—(5-(3-quinolinyl)-3-pyridyl),
—C(H)=CH—(5-(5-pyrimidinyl)-3-pyridyl),
—C(H)=CH—(5-(3-pyridyl)-3-pyridyl),
—C(H)=CH—(5-(4-isoquinolinyl)-3-pyridyl),
—C(H)=CH—(5-(3-thienyl)-3-pyridyl),
—C(H)=CH—(5-(2-furyl)-3-pyridyl),
—C(H)=CH—(5-(2-(1,3-thiazolyl))-3-pyridyl),
—C(H)=CH—(5-(2-(trimethylsilyl)-1,3-thiazol-5-yl)-3-pyridyl),
—C(H)=CH—(5-(1,3-thiazolyl)-3-pyridyl),
—C(H)=CH—(5-(2-amino-(1,3-thiazol-5-yl))-2-thienyl),
—C(H)=CH—(5-(2-amino-(1,3-thiazol-5-yl))-2-thienyl),
—C(H)=CH—(5-(3-pyridyl)-2-(1,3-thiazolyl)),
—C(H)=CH—(2-(3-pyridyl)-5-(1,3-thiazolyl)),
—C(H)=CH—(2-(5-bromo-1,3-thiazol-2-yl)-5-(1,3-thiazolyl)),
—C(H)=CH—(2-(5-bromo-(1,3-thiazol-2-yl))-5-(1,3-thiazolyl)),
—C(H)=CH—(2-(5-bromo-1,3-thiazol-2-yl)-5-(1,3-thiazolyl)),
—C(H)=CH—(2-(2-thienyl)-5-thiazolyl),
—C(H)=CH—(2-(2-pyrazinyl)-5-(1,3-thiazolyl)),
—C(H)=CH—(2-(5-pyrimidinyl)-5-(1,3-thiazolyl)),
—C(H)=CH—(2-(5-(1,3-thiazol-5-yl)-5-(1,3-thiazolyl)),
—C(H)=CH—(5-(2-pyrimidinyl)-2-thienyl),
—C(H)=CH—(5-(2-pyrazinyl)-2-thienyl),
—C(H)=CH—(5-(2-(1,3-thiazolyl)-2-thienyl),
—C(H)=CH—(5-(4-pyrimidinyl)-2-thienyl),
—C(H)=CH—(4-(3-pyridyl)-2-(1,3-thiazolyl)),
—C(H)=CH—(4-(3-pyridyl)-2-(1,3-thiazolyl)),
—C(H)=CH—(4-(3-pyridyl)-2-(1,3-thiazolyl)),
—C(H)=CH—(4-(2-thienyl)-2-(1,3-thiazolyl)),
—C(H)=CH—(5-(3-pyridyl)-2-thienyl),
—C(H)=CH—(5-(2-pyrazinyl)-2-thienyl),
—C(H)=CH—(5-(5-pyrimidinyl)-2-thienyl),
—C(H)=CH—(5-(3,4-dichlorophenyl)-2-thienyl),
—C(H)=CH—(5-(3-fluorophenyl)-2-thienyl), —C(H)=CH—(5-(5-(1,3-thiazoyl))-2-thienyl), —C(H)=CH—(2,2'-bisthienyl), —C(H)=CH—(5-(2-pyridyl)-2-thienyl), —C(H)=CH—(5-(3-thienyl)-2-thienyl), and —C(H)=CH—(5-(2-furanyl)-2-thienyl).

12. A pharmaceutical composition comprising a pharmaceutically effective amount of a compound of claim 1 in combination with a pharmaceutically acceptable carrier.

13. A method of treating a bacterial infection in a mammal in need of such treatment which comprises administering to said mammal a therapeutically effective amount of a compound of claim 1.

14. A process for preparing a compound selected from the group consisting of a compound of formula I

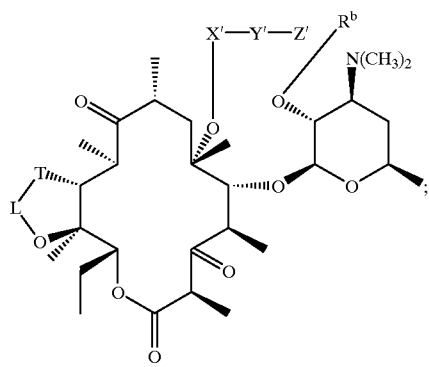

compound of formula II

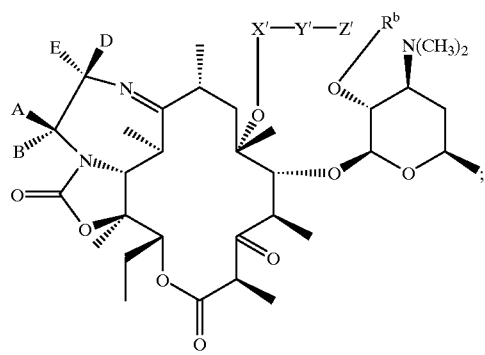

and a compound of formula III

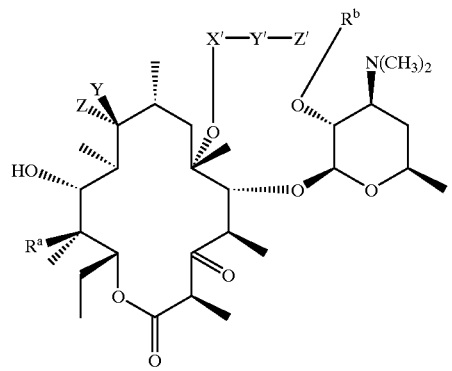

or a pharmaceutically acceptable salt, solvate, ester or prodrug thereof, wherein either:

(a) Y and Z taken together define a group X, and X is selected from the group consisting of
  (1) =O,
  (2) =N—OH,
  (3) =N—O—$R^1$ where $R^1$ is selected from the group consisting of
    (a) unsubstituted $C_1$–$C_{12}$ alkyl,
    (b) $C_1$–$C_{12}$ alkyl substituted with aryl,
    (c) $C_1$–$C_{12}$ alkyl substituted with substituted aryl,
    (d) $C_1$–$C_{12}$ alkyl substituted with heteroaryl,
    (e) $C_1$–$C_{12}$ alkyl substituted with substituted heteroaryl,
    (f) $C_3$–$C_{12}$ cycloalkyl, and
    (g) —Si—$(R^2)(R^3)(R^4)$ wherein $R^2$, $R^3$ and $R^4$ are each independently selected from the group consisting of $C_1$–$C_{12}$ alkyl and aryl; and
  (4) =N—O—$C(R^5)(R^6)$—O—$R^1$ where $R^1$ is as previously defined and $R^5$ and $R^6$ are each independently selected from the group consisting of
    (a) hydrogen,
    (b) unsubstituted $C_1$–$C_{12}$ alkyl,
    (c) $C_1$–$C_{12}$ alkyl substituted with aryl,
    (d) $C_{1-C12}$ alkyl substituted with substituted aryl,
    (e) $C_1$–$C_{12}$ alkyl substituted with heteroaryl, and
    (f) $C_1$–$C_{12}$ alkyl substituted with substituted heteroaryl,
    or $R^5$ and $R^6$ taken together with the atom to which they are attached form a $C_3$–$C_{12}$ cycloalkyl ring; or (b) one of Y and Z is hydrogen and the other is selected from the group consisting of
  (1) hydrogen,
  (2) hydroxy,
  (3) protected hydroxy, and
  (4) $NR^7R^8$ wherein $R^7$ and $R^8$ are independently selected from the group consisting of hydrogen and $C_1$–$C_6$ alkyl, or $R^7$ and $R^8$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$-$C_6$-alkyl-)—, —N(aryl)—, —N(aryl-$C_1$-$C_6$-alkyl-)—, —N(substituted-aryl-$C_1$-$C_6$-alkyl-)—, —N(heteroaryl)—, —N(heteroaryl-$C_1$-$C_6$-alkyl-)—, —N(substituted-heteroaryl-$C_1$-$C_6$-alkyl-)—, and —S— or —S(O)$_n$—, wherein n is 1 or 2;

$R^a$ is hydrogen or hydroxy;

$R^b$ is hydrogen or a hydroxy protecting group;

L is methylene or carbonyl, provided that when L is methylene, T is —O—;

T is selected from the group consisting of —O—, —NH—, and —N(W-$R^d$)—, wherein W is absent or is selected from the group consisting of —O—, —NH—CO—, —N=CH— and —NH—, and $R^d$ is selected from the group consisting of (1) hydrogen, (2) $C_1$–$C_6$ alkyl optionally substituted with one or more substituents selected from the group consisting of
 (a) aryl,
 (b) substituted aryl,
 (c) heteroaryl,
 (d) substituted heteroaryl,
 (e) hydroxy,
 (f) $C_1$–$C_6$ alkoxy,
 (g) $NR^7R^8$, wherein $R^7$ and $R^8$ are as defined previously, and
 (h) —$CH_2$—M—$R^9$,
 wherein M is selected from the group consisting of
  (i) —C(O)—NH—,
  (ii) —NH—C(O)—,
  (iii) —NH—,
  (iv) —N=,
  (v) —N($CH_3$)—,
  (vi) —NH—C(O)—O—
  (vii) —NH—C(O)—NH—
  (viii) —O—C(O)—NH—
  (ix) —O—C(O)—O—
  (x) —O—,
  (xi) —S(O)$_n$—, wherein n is 0, 1 or 2,
  (xii) —C(O)—O—,
  (xiii) —O—C(O)—, and
  (xiv) —C(O)—; and
 wherein $R^9$ is selected from the group consisting of:
  (i) $C_1$–$C_6$ alkyl, optionally substituted with a substituent selected from the group consisting of
   (aa) aryl,
   (bb) substituted aryl,
   (cc) heteroaryl, and
   (dd) substituted heteroaryl;
  (ii) aryl,
  (iii) substituted aryl,
  (iv) heteroaryl,
  (v) substituted heteroaryl, and
  (vi) heterocycloalkyl;
(3) $C_3$–$C_7$ cycloalkyl,
(4) aryl,
(5) substituted aryl,
(6) heteroaryl, and
(7) substituted heteroaryl;

X' is selected from the group consisting of $C_1$–$C_{10}$ alkyl, $C_3$–$C_{10}$ alkenyl, and $C_3$–$C_{10}$ alkynyl;

Y' and Z' are independently selected from the group consisting of:

(e) optionally substituted aryl, and
(f) optionally substituted heteroaryl, with the proviso that both Y' and Z' are not both phenyl, and with the further proviso that Y' is not isoxazole when Z, is thiophenyl;

and A, B, D and E are independently selected from the group consisting of:

(a) hydrogen;
(b) $C_1$–$C_6$ alkyl, optionally substituted with one or more substituents selected from the group consisting of:
 (i) aryl;
 (ii) substituted aryl;
 (iii) heteroaryl;
 (iv) substituted heteroaryl;
 (v) heterocycloalkyl;
 (vi) hydroxy;
 (vii) $C_1$–$C_6$ alkoxy;
 (viii) halogen consisting of Br, Cl, F or I; and
 (ix) $NR^7R^8$, wherein $R^7$ and $R^8$ are as previously defined;
(c) $C_3$–$C_7$ cycloalkyl;
(d) aryl;
(e) substituted aryl;
(f) heteroaryl;
(g) substituted heteroaryl;
(h) heterocycloalkyl; and
(i) a group selected from option (b) as defined above A, B, D and E further substituted with —M—$R^9$, wherein M and $R^9$ are as previously defined, with the proviso that at least two of A, B, D and E are hydrogen,;

or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$ alkyl-)—, —N(aryl-$C_1$–$C_6$alkyl-)—, —N(substituted aryl-$C_1$–$C_6$ alkyl-)—, —N(heteroaryl-$C_1$–$C_6$ alkyl-)—, —N(substituted heteroaryl- $C_1$–$C_6$alkyl-)—, —S— or —S(O)$_n$—, wherein n is 1 or 2, —C(O)—NH, —C(O)—$NR^{12}$—, wherein $R^{12}$ is selected from the group consisting of hydrogen, $C_1$–$C_3$ alkyl, $C_1$–$C_3$ alkyl substituted with aryl, substituted aryl, heteroaryl, or substituted heteroaryl, —NH—C(O)—, and —$NR^{12}$—C(O)—;

wherein said process comprises:
coupling a compound selected from the group consisting of a compound of formula I$^a$

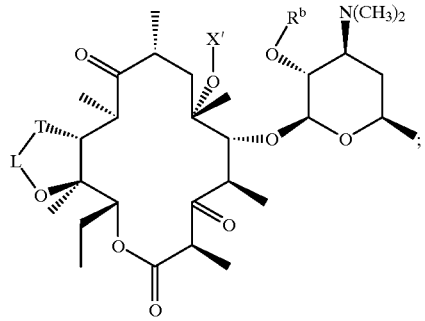

a compound of formula II$^a$

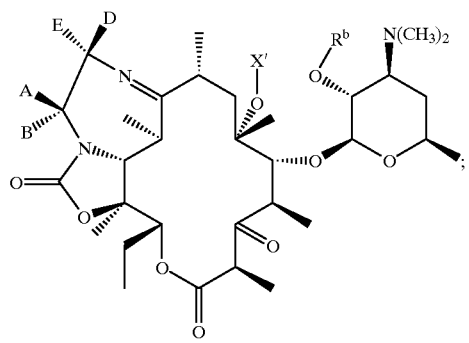

and a compound of formula III$^a$

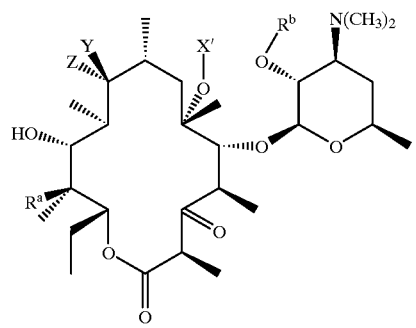

wherein
R$^b$ is a hydroxy protecting group, and
Y, Z, X, R$^1$, R$^2$, R$^3$, R$^4$, R$^5$, R$^6$, R$^7$, R$^8$, n, R$^a$, L, T, R$^d$, W, M, R$^9$, X', Y', Z', A, B, D, E, R$^{12}$ are as previously defined;
with a compound selected from the group consisting of X$^1$—Y'—Z' and X$^1$—Y'—X$^2$, wherein X$^1$ and X$^2$ are independently selected from the group consisting of bromide, iodide, sulfonate, trialkylstannane, boronic acid, and borate, and Y' and Z' are as previously defined;
in the presence of a palladium catalyst, with the proviso that when X$^1$—Y'—X$^2$ is employed, a subsequent coupling reaction is performed with X$^3$—Z', wherein X$^3$ is selected from the group consisting of bromide, iodide, sulfonate, trialkylstannane, boronic acid, and borate, and Z' is as previously defined;
(b) optionally deprotecting; and
(c) optionally isolating the compound.

* * * * *

UNITED STATES PATENT AND TRADEMARK OFFICE
CERTIFICATE OF CORRECTION

PATENT NO : 6,054,435
DATED : April 25, 2000
INVENTOR(S) : Yan Sun Or et al.

It is certified that error appears in the above-identified patent and that said Letters Patent are hereby corrected as shown below:

Col. 62, line 12
 replace ";"
 with -- --.
Col. 62, line 30
 replace ";"
 with -- --.
Col. 67, line 29
 replace ";"
 with -- --.
Col. 67, line 48
 replace ";"
 with -- --.
Col. 71, line 11
 replace ";"
 with -- --.
Col. 71, line 30
 replace ";"
 with -- --.

Signed and Sealed this

First Day of May, 2001

NICHOLAS P. GODICI

Attest:

Attesting Officer

Acting Director of the United States Patent and Trademark Office